United States Patent
Bathurst et al.

(10) Patent No.: US 6,949,529 B2
(45) Date of Patent: *Sep. 27, 2005

(54) COMPOSITIONS CONTAINING LYSOPHOTIDIC ACIDS WHICH INHIBIT APOPTOSIS AND USES THEREOF

(75) Inventors: Ian C. Bathurst, Kensington, CA (US); Matthew W. Foehr, San Francisco, CA (US); J. Graham Goddard, San Francisco, CA (US); Samiul R. Umansky, Richmond, CA (US); John D. Bradley, Brookoline, MA (US); Donald H. Picker, Warren, NJ (US)

(73) Assignee: Sky High, LLC, Evanston, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 10/267,568

(22) Filed: Oct. 8, 2002

(65) Prior Publication Data

US 2003/0149002 A1 Aug. 7, 2003

Related U.S. Application Data

(63) Continuation of application No. 09/381,489, filed as application No. PCT/US98/05325 on Mar. 18, 1998, now Pat. No. 6,495,532.
(60) Provisional application No. 60/039,379, filed on Mar. 19, 1997, provisional application No. 60/039,380, filed on Mar. 19, 1997, provisional application No. 60/039,376, filed on Mar. 19, 1997, provisional application No. 60/056,120, filed on Aug. 20, 1997, and provisional application No. 60/056,744, filed on Aug. 20, 1997.

(51) Int. Cl.[7] .................. A61K 31/66; A61K 31/07; A61K 38/00; A61K 47/00
(52) U.S. Cl. .................. 514/110; 514/2; 514/120; 514/725; 514/784; 514/785
(58) Field of Search .................. 514/110, 2, 120, 514/725, 784, 785

(56) References Cited

U.S. PATENT DOCUMENTS

| | | | |
|---|---|---|---|
| 4,263,286 A | 4/1981 | Nakajima et al. | |
| 4,340,586 A | 7/1982 | Bekierkunst et al. | |
| 4,695,590 A | 9/1987 | Lippman | |
| 4,746,652 A | 5/1988 | Buckalew, Jr. et al. | |
| 4,793,996 A | 12/1988 | Kennedy et al. | |
| 4,818,540 A | 4/1989 | Chien et al. | |
| 4,938,961 A | 7/1990 | Collins et al. | |
| 4,959,310 A | 9/1990 | Brandon et al. | |
| 4,959,353 A | 9/1990 | Brown et al. | |
| 5,053,327 A | 10/1991 | Brandon et al. | |
| 5,093,505 A | 3/1992 | Nishino et al. | |
| 5,130,298 A | 7/1992 | Cini et al. | |
| 5,140,043 A | 8/1992 | Darr et al. | |
| 5,217,717 A | 6/1993 | Kennedy et al. | |
| 5,238,965 A | 8/1993 | Piazza et al. | |
| 5,326,690 A | 7/1994 | Xu et al. | |
| 5,330,972 A | 7/1994 | Cope | |
| 5,340,568 A | 8/1994 | Piazza et al. | |
| 5,521,223 A | 5/1996 | Piazza et al. | |
| 5,624,672 A | 4/1997 | Bathurst et al. | |
| 5,635,187 A | 6/1997 | Bathurst et al. | |
| 5,636,187 A | 6/1997 | Fujii et al. | |
| 5,693,626 A | 12/1997 | Saksena et al. | 514/85 |
| 5,759,548 A | 6/1998 | Bathurst et al. | |
| 6,004,579 A | 12/1999 | Bathurst et al. | |
| 6,306,398 B1 | 10/2001 | Bathurst et al. | |
| 6,495,532 B1 * | 12/2002 | Bathurst et al. | 514/110 |

FOREIGN PATENT DOCUMENTS

| | | |
|---|---|---|
| EP | 0626177 | 11/1994 |
| JP | 63-51335 | 3/1988 |
| WO | WO 90/03574 | 4/1990 |
| WO | WO 94/20121 | 9/1994 |
| WO | WO 94/25621 | 11/1994 |
| WO | WO 99/47101 | 9/1999 |

OTHER PUBLICATIONS

Russel, ed., Specialized nutrition for persons with human immunodeficiency virus (HIV) infection or acquired immunodeficiency syndrome (AIDS) Ross Products Division, Abbott Laboratories (1993), Advera pamphlet, pp. 1–69.
Wu et al., *American Society of Transplant Physicians*, Dallas, Texas, May 26–29, 1996, Abstract No. 310.
Wu et al., 22nd *Annual Scientific Meeting of the American Society of Transplant Surgeons*, Dallas, texas, May 29–31, 1996, Abstract No. P–41.
Avaeva et al., "Hydrolysis of the methyl ester of O–phosphoserine," *Chem Abstracts* 1972, 76:46490, p. 402.
Earle et al., "Large Scale Synthesis of Cyclodiphospho–D–glycerate," *J. Org. Chem.* 1996, 61:5697–5700.
Neumann, "Phosphoryl Transfer from S–Substituted Monoesters of Phosphorothioic Acid to Various Acceptors Catalyzed by Alkaline Phosphatase from *Eschericia coli*," *European Journal of Biochemistry*, 1969, 8:164–173.
Svyato et al., "Inactivation of Inorganic Pyrophosphatase from Yeasts by O–phosphoserine and its methyl ester," *Chemical Abstracts* 1980, 92:17901, p. 289–290.
Black et al., "Enzymatic Formation of Glyceryl and Phosphoglyceryl Methylthiol Esters," *J. Biol. Chem.* 221:171–180, 1956.
Cherbuliez et al., "Recherches sur la formation et al transformation des esters XII,"*Helvetica Chimica Acta* 41:1163–68, 1958.

* cited by examiner

Primary Examiner—Kevin E. Weddington
(74) Attorney, Agent, or Firm—Sheridan Ross P.C.

(57) ABSTRACT

The present invention provides therapeutic compositions containing lysophosphatidic acids, methods for making the compositions, and methods of use thereof.

29 Claims, 17 Drawing Sheets

FIGURE 15
CONTROL +S, +G
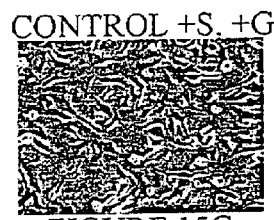
FIGURE 15G
CERAMIDE
10 µM
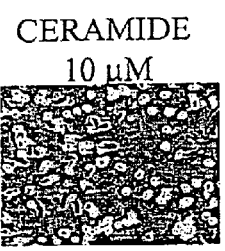
FIGURE 15A
CERAMIDE
15 µM
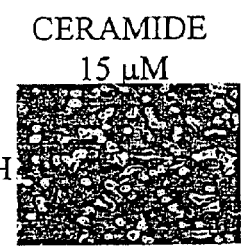
FIGURE 15H
0.3%PEG
FIGURE 15B
0.3%PEG
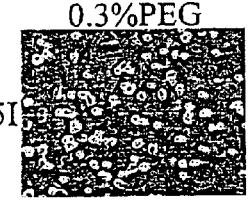
FIGURE 15I
2%PEG
FIGURE 15C
2%PEG
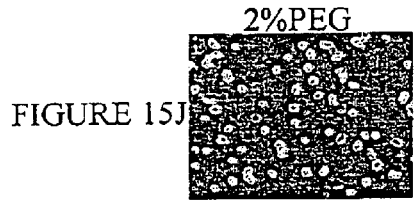
FIGURE 15J
5µM ELIREX
FIGURE 15D
5µM ELIREX
FIGURE 15K
5µM ELIREX+0.3%PEG
FIGURE 15E
5µM ELIREX+0.3%PEG
FIGURE 15L
5µM ELIREX+2%PEG
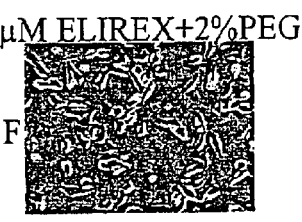
FIGURE 15F
5µM ELIREX+2%PEG
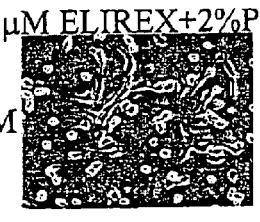
FIGURE 15M

COMPOSITIONS CONTAINING LYSOPHOTIDIC ACIDS WHICH INHIBIT APOPTOSIS AND USES THEREOF

CROSS-REFERENCE TO RELATED APPLICATIONS

The present application is a continuation of U.S. patent application Ser. No. 09/381,489, filed Feb. 28, 2000, now U.S. Pat. No. 6,495,532 which claims priority from PCT/US98/05325, filed Mar. 18, 1998, which claims priority from U.S. Provisional Application Nos. 60/039,379, filed Mar. 19, 1997, 60/039,380, filed Mar. 19, 1997, 60/039,376, filed Mar. 19, 1997, 60/056,120, filed Aug. 20, 1997, and 60/056,744, filed Aug. 20, 1997.

STATEMENT OF RIGHTS TO INVENTIONS MADE UNDER FEDERALLY SPONSORED RESEARCH (Not Applicable)

TECHNICAL FIELD

This invention relates to therapeutically effective compositions of matter. More specifically, it encompasses compositions containing lysophosphotidic acid or analogs and derivatives thereof, (collectively "LPA") which have been found to exhibit anti-apoptotic activity and/or to preserve or restore cell, tissue or organ function. The invention also relates to compositions containing LPA and a potentiating component, as described below. Additionally, this invention relates to methods of use of these therapeutically effective compositions.

BACKGROUND OF THE INVENTION

Phospholipids

Phospholipids are a class of amphipathic phosphorous-containing lipids which are essential constituents of biological membranes. Various phospholipid preparations have been used for cooking, drug delivery (liposomes), slow release delivery systems, carrier media for hydrophobic drugs, gene transfer and replacement therapy, sunscreens, emulsions, anti-foaming agents, replacement of damaged or absent pulmonary surfactants, detergents and membrane stabilization. Phosphatidic acid (PA), phosphatidylinositol (PI), lysophosphatidic acid, lysophosphatidylinositol (LPI), and lysophosphatidylcholine (LPC) are found in a variety of plant and animal products. Lysophosphatidic acid analogs have been reported to have a variety of physiological activities including mitogenesis (i.e. prevention of hyperproliferative diseases), vasodilation, growth factor, wound healing and to be an anti-wrinkle agent. U.S. Pat. Nos. 4,263,286; 4,746,652; 5,326,690; 5,480,877; 5,565,439; and 5,340,568. Lysophosphatidic acid is reviewed in detail by Moolenaar (1994) *TICB* 4:213–219; Eichholtz et al. (1990) *Biochem. J.* 291:677–680; and Moolenaar (1995) *J. Biol. Chem.* 270:12949–12952.

Previous studies have shown that lysophosphatidic acid, when bound to serum albumin, can activate membrane currents in *Xenopus* oocytes and induce neurite retraction in PC12 pheochromocytoma cells.

Apoptosis

A wide variety of physiologic damage is due to cell death. Two forms of cell death, necrosis and apoptosis, have been described and are being intensively and widely investigated. Kerr et al. (1972) *Br. J. Cancer* 26:239–257; Umansky (1996) *Molekulyarnaya Biologiya* 30:285–295; and Vaux and Strasser (1996) *Proc. Natl. Acad. Sci.* 93:2239–2244. Necrosis is generally considered to be a result of severe irreversible cell damage. It is characterized by early swelling of the cell and its cytoplasmic organelles with subsequent rupture of the cellular membrane.

Apoptosis is a normal physiologic process that leads to individual cell death. This process of programmed cell death is involved in a variety of normal and pathogenic biological events and can be induced by a number of unrelated stimuli. Changes in the biological regulation of apoptosis also occur during aging and are responsible for many of the conditions and diseases related to aging.

Studies of apoptosis have implied that a common metabolic pathway leading to apoptosis can be initiated by a wide variety of signals, including hormones, serum growth factor deprivation, chemotherapeutic agents, ionizing radiation, and infection by human immunodeficiency virus (HIV). Wyllie (1980) *Nature* 284:555–556; Kanter et al. (1984) *Biochem. Biophys. Res. Commun.* 118:392–399; Duke and Cohen (1986) *Lymphokine Res.* 5:289–299; Tomei et al. (1988) *Biochem. Biophys. Res. Commun.* 155:324–331; Kruman et al. (1991) *J. Cell. Physiol.* 148:267–273; Ameisen and Capron (1991) *Immunol. Today* 12:102–105; and Sheppard and Ascher (1992) *J. AIDS* 5:143–147. Apoptosis can also be induced by mild, non-catastrophic cell injury and can be concomitant with adjacent necrosis. Agents that affect the biological control of apoptosis thus have therapeutic utility in numerous clinical indications.

Apoptotic cell death is characterized by morphologic changes such as cellular shrinkage, chromatin condensation and margination, cytoplasmic blebbing, and increased membrane permeability. Gerschenson et al. (1992) *FASEB J.* 6:2450–2455; and Cohen and Duke (1992) *Ann. Rev. Immunol.* 10:267–293. Specific internucleosomal DNA fragmentation is a hallmark for many, but notably not all, instances of apoptosis.

Several genes and gene families involved in signal transduction and modulation of apoptosis have been described. Apoptosis, however, is an active cellular response to a physiologic or external signal and can be modulated by interfering with the apoptotic pathway. Conversely, by definition, necrosis can be prevented only by decreasing cell injury. Prevention of apoptosis by upregulation of bcl-2 and bcl-x expression, or by inhibitors of ICE-like proteases are typical examples of modulation of cell death. Umansky (1996); Vaux and Strasser (1996); Nunez et al. (1994) *Immunol. Today* 15:582–588; and Whyte (1996) *Trends in Cell Biol.* 6:245–148.

Apoptotic cell death appears to play a significant role in the tissue damage that occurs in association with, e.g., ischemia, organ transplantation, and various gastrointestinal disorders.

Ischemia and Reperfusion

Ischemia is the result of decreased blood flow to a particular area or organ of the body. Ischemia is responsible for several important types of physiologic damage such as brain damage, spinal cord trauma and myocardial ischemia. The most important consequence of acute myocardial ischemia is the death of individual heart cells which leads to organ dysfunction. Early reperfusion decreases heart damage; however, massive cell death by apoptosis can occur with the restoration of blood flow. In this instance, the cells that die are those that remained viable at the end of ischemia. Karmazyn (1991) *Can. J. Physiol.* 69:719–730; and Fox (1992) *Cardiovasc. Res.* 26:656–659.

Support for the role of apoptosis in heart injury induced by ischemia and subsequent reperfusion has been provided by numerous laboratories. Gottlieb et al. (1994) *J. Clin. Invest.* 94:1621–1628; Umansky et al. (1995) *Cell Death and Differentiation* 2:235–241; Umansky et al. (1996) *Basic and Applied Myology* 6:227–235; and Itoh et al. (1995) *Am. J. Pathol.* 146:1325–1331. Severe cell damage during prolonged ischemia appears to result in necrotic death of myocardial cells. However, if the ischemia is relatively limited in extent and duration, the apoptotic pathway is initiated. Restoration of blood flow (reperfusion) allows apoptosis to proceed. Insulin-like growth factors (IGF) and calpain inhibitors, which are capable of preventing apoptosis in different systems, also inhibited apoptosis of cardiomyocytes following ischemia and reperfusion both in vivo and in vitro. Umansky et al. (1995); and Buerke et al. (1995) *Proc. Natl. Acad. Sci. USA* 92:8031–8035.

Organ Preservation

Transplantation of vital organs such as the heart, liver, kidney, pancreas, and lung has become increasingly successful and sophisticated in recent years. Because mammalian organs progressively lose their ability to function during storage, even at freezing temperatures, transplant operations need to be performed expeditiously after organ procurement so as to minimize the period of time that the organ is without supportive blood flow. This diminishes the availability of organs to patients in need of transplants.

In clinical practice, the two major situations in which cardiac preservation is required are heart transplantation and cardioplegia for open heart surgery. In heart transplantation, the donor heart is exposed through a midline sternotomy. After opening the pericardium, the superior and inferior vena cavae and the ascending aorta are isolated. The venous inflow is then occluded, the aorta is cross clamped, and approximately 1 liter of cold organ preservation solution (OPS) is flushed into the aortic root under pressure through a needle; as a result, the heart is immediately arrested. Cooling is supplemented by surrounding the heart with iced saline. The chilled, arrested heart is then surgically excised, immersed in cold OPS, packed in ice and rushed to the recipient center.

The recipient's chest is opened through a midline sternotomy, and after placing the patient on cardiopulmonary bypass, the diseased heart is excised. The preserved donor heart is then removed from the OPS, trimmed appropriately and sewn to the stumps of the great vessels and the two atria in the recipient chest. After completion of the vascular anastomoses, blood is allowed to return to the heart. The transplanted heart will then either resume beating spontaneously or will require chemical and electrical treatment to restore normal rhythm. When the heart is ready to take over the circulation, the cardiopulmonary bypass is discontinued and the recipient's chest closed.

Most non-transplant surgical procedures on the heart, such as coronary artery bypass grafting, require that the heart's action be arrested for a period ranging from 1 to 4 hours. During this time, the heart is kept cool by external cooling as well as by periodically reflushing an OPS through the coronary arteries. The OPS composition is designed to rapidly arrest the heart and to keep it in good condition during the period of standstill so that it will resume normal function when the procedure is finished.

In cardioplegic procedures, the heart is exposed in the chest and, at a minimum, the aortic root is isolated. A vascular clamp is applied across the aorta and approximately 1 liter of cold OPS is flushed into the aortic root through a needle. Venting is provided through the left ventricle, pulmonary artery or the right atrium and the effluent, which can contain high levels of potassium, is sucked out of the chest. This, together with external cooling, produces rapid cessation of contractions. During the period of arrest, the patient's circulation is maintained artificially using cardiopulmonary bypass.

After completion of the surgical procedure, blood flow is restored to the coronary circulation and heartbeat returns either spontaneously or after chemical and electric treatment. The ease with which stable function is restored depends to a large extent on the effectiveness of preservation by the OPS. Once the heart is beating satisfactorily, cardiopulmonary bypass is discontinued and the chest closed. General methods for organ transplant and heart surgery are disclosed in D. K. C. Cooper (editor), *The Transplantation and Replacement of Thoracic Organs*, Boston, Kluwer Academic Publishers (1997); and Collins et al. (1992) *Kidney International* 42:S-197–S-202 and the art cited therein, and are commonly known in the art.

It is generally understood that "living" organs, including the heart, continue the process of metabolism after removal from the donor so that cell constituents are continuously metabolized to waste products. If the storage technique is inadequate, the accumulation of these metabolic waste products, depletion of cell nutrients and consequent derangement of cell composition lead to progressive loss of function and ultimately to cell death. That is, the organ will lose its ability to function adequately after transplantation into the recipient. Several procedures have been explored to successfully enable organ preservation ex vivo for useful time periods. In one method, the donor organ is cooled rapidly by flushing cold solutions through the organ's vascular system and maintaining the organ at temperatures near 0° C. for the purpose of greatly slowing the metabolic rate. In the case of the mammalian heart, the flush solution composition is designed to cause the heart to rapidly stop beating as well as to preserve it.

In 1988, University of Wisconsin (UW) solution was introduced. Belzer et al. (1988) *Transplantation* 45:673–676. This solution, capable of preserving the pancreas and kidney for 72 hours, and the liver for 30 hours, subsequently became the standard organ preservation solution (OPS) for transplant surgery and the benchmark against which other OPS compositions were measured. However, the heart is more recalcitrant to long-term storage than other organs, and UW solution is unreliable for storage of hearts for as short a period as 24 hours. Wicomb et al. (1989) *Transplantation* 47:733–734.

Improvements in the design of OPS compositions, as reviewed in Collins et al. (1992) *Kidney International* 42:S-197–S-202 and others described in the art, have proceeded along several paths, including: (1) modification and simplification of UW solution; (2) investigation of organ-specific requirements; (3) addition of pharmacologic agents, particularly calcium antagonists for control of acidosis; (5) the use of a terminal rinse solution; and (6) the use of solutions containing PEG.

Wicomb et al. reported the beneficial effects of PEG 8000 on rabbit hearts preserved by oxygenated low pressure perfusion for 24 hours; this solution also contained horseradish peroxidase. Wicomb et al. (1989) *Transplantation Proceedings* 21:1366–1368. The substitution of PEG20M for hydroxyethyl starch (HES) as the colloid in UW solution also yielded excellent cardiac function. PEG20M consists of two or more molecules of PEG 6000–8000 joined by a bisphenol epoxide linker (CAS #37225-26-6; CAS name Oxirane, 2, 2' [(1-methyl-ethylidene)bis(4,1-phenyleneoxy methylene)]bis-, polymer with α-hydro-ω-hydroxypoly (oxy-1,2-ethanediyl). The substitution of PEG20M for HES also allowed baboon heart storage up to 48 hours and increased cardiac output (CO) under conditions of microperfusion. Wicomb et al. (1986) *J. Surg. Res.* 40:276; and Wicomb et al. (1989) *Transplantation* 48:6–9. "Microperfusion" is a hypoxic, very-low-flow perfusion with flowrates such as 3 ml/g heart wt/24 hour, which is ⅟₅₀₀ of that typical of conventional continuous perfusion. Wicomb et al. (1989) Transplantation 48:6–9.

An improved OPS, Cardiosol™ heart preservation solution, contained the substitution of PEG20M for HES and eliminated five components of UW solution (penicillin, dexamethasone, insulin, allopurinol, and adenosine). Wicomb et al. (1990) *Transplantation* 49:261–264; and U.S. Pat. No. 4,938,961. Cardiosol™ heart preservation solution contains 5% or 10% by weight PEG 20M (Union Carbide Chemicals and Plastics Co., Inc., Charleston, W. Va.), 40 mM sodium, 125 mM potassium, 5 mM magnesium, 25 mM phosphate, 5 mM sulfate, 100 mM lactobionate, 30 mM raffinose, and 3 mM glutathione. Collins et al., *The Lancet* 338:890–891 (1991); and Wicomb et al. (1994) *J. Heart Lung Transplantation* 13:891–894. This solution was found to be superior to UW solution both for 4-hour hypothermic and 24-hour microperfusion storage. Collins et al. (1992).

Gastrointestinal Disorders

A variety of food supplements containing, in part, partially processed plant extracts have been used to ameliorate the gastrointestinal disorders that often accompany chemotherapy, radiation and AIDS. The supplements generally contain carbohydrates, fat and plant protein hydrolysates. See, e.g., Tomei and Cope et al. in *Apoptosis: The Molecular Basis of Cell Death* (1991) Cold Spring Harbor Laboratory Press. PCT Publication No. WO 95/15173 and U.S. Pat. Nos. 5,620,885, 5,567,425, 5,635,186 and 5,624, 672 describe plant-derived extracts that produce an anti-apoptotic effect. It has now been found that these extracts contain the following phospholipids: 18:1-LPA, lysophosphatidylcholine (LPC), lysophosphatidylinositol (LPI), phosphatidic acid (PA) and phosphatidylinositol (PI) in the ratios of approximately 2:1:2:20:20, by weight in addition to various optional protein and carbohydrate constituents.

A method of preserving or restoring cell, tissue, or organ function, and/or preventing apoptosis would be useful for a variety of therapeutic uses, particularly organ preservation.

All references cited herein are incorporated by reference in their entirety.

SUMMARY OF THE INVENTION

This invention relates to therapeutically effective compositions of matter. More specifically, it encompasses compositions containing lysophosphotidic acid or analogs and derivatives thereof, (collectively "LPA") which have been found to exhibit anti-apoptotic activity or to preserve or restore cell, tissue or organ function. Additionally, this invention relates to methods of use of these therapeutically effective compositions. A method of preserving or restoring cell, tissue, or organ function, and/or preventing apoptosis would be useful for a variety of therapeutic uses, particularly organ preservation.

The present invention encompasses compositions comprising a therapeutically effective amount of an LPA and a potentiating component in an amount sufficient to potentiate the therapeutic effectiveness of the LPA. In specific embodiments, the component is a polyethylene glycol, a protein, or a lipid membrane structure.

In one embodiment, LPA has the formula:

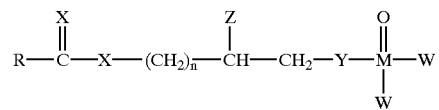

or a cyclic phosphate derivative thereof having the structure:

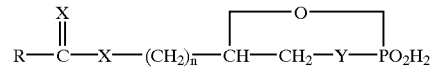

wherein each X is independently O or S; M is P or S, where when M is S, one W is (=O); each W is independently SH, OH, OCH$_2$CH(NH$_2$)CO$_2$H, OCHCH$_3$CH(NH$_2$)CO$_2$H, OPO$_3$H$_2$, or OPO$_2$HOPO$_3$H$_2$, where if one W is OPO$_3$H$_2$ or OPO$_2$HOPO$_3$H$_2$, the remaining W is OH; Z is OH, SH, NH$_2$, halogen, OPO$_3$H$_2$, H, O(CH$_2$)$_b$CH$_3$ where b=0 to about 2, or SO$_3$H; R is unsubstituted or substituted, saturated or unsaturated, straight or branched-chain alkyl having from about 10 to about 24 carbon atoms, or ((CH$_2$)$_m$O)$_p$(CH$_2$)$_m$W where p is an integer from 1 to about 900 and where each m is independently an integer from 2 to about 10 and W is OH, or O(CH$_2$)$_q$CH$_3$ where q is an integer from 0 to about 10; Y is O or S; and n is an integer from 0 to about 10; or a pharmaceutically acceptable salt thereof.

In another embodiment, LPA has the formula:

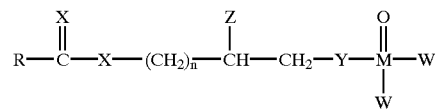

or a cyclic phosphate derivative thereof having the structure:

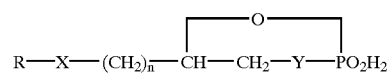

wherein X is O, S, or CH$_2$; M is P or S, where when M is S, one W is (=O); each W is independently SH, OH, OCH$_2$CH(NH$_2$)CO$_2$H, OCHCH$_3$CH(NH$_2$)CO$_2$H, OPO$_3$H$_2$, or OPO$_2$HOPO$_3$H$_2$, where if one W is OPO$_3$H$_2$ or OPO$_2$HOPO$_3$H$_2$, the remaining W is OH; Z is OH, SH, NH$_2$, halogen, OPO$_3$H$_2$, H or SO$_3$H; R is unsubstituted or substituted, saturated or unsaturated, straight or branched-chain alkyl having from about 10 to about 24 carbon atoms, or ((CH$_2$)$_m$O)$_p$(CH$_2$)$_m$W where p is an integer from 1 to about 900 and where each m is independently an integer from 2 to about 10 and W is OH, or O(CH$_2$)$_q$CH$_3$ where q is an integer from 0 to about 10; Y is O or S; and n is an integer from 0 to about 10; or a pharmaceutically acceptable salt thereof.

In another embodiment, LPA has the formula:

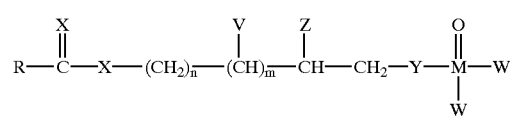

or a cyclic phosphate derivative thereof having the structure:

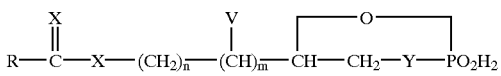

wherein each V is independently OH, —SH, H, $NH_2$, halogen, $OPO_3H_2$, or $OSO_3H$; each X is independently O or S; M is P or S, where when M is S; one W is (=O); each W is independently SH, OH, $OCH_2CH(NH_2)CO_2H$, $OCHCH_3CH(NH_2)CO_2H$, $OPO_3H_2$, or $OPO_2HOPO_3H_2$, where if one W is $OPO_3H_2$ or $OPO_2HOPO_3H_2$, the remaining W is OH; Z is OH, SH, $NH_2$, halogen, $OPO_3H_2$, H or $SO_3H$; R is unsubstituted or substituted, saturated or unsaturated, straight or branched-chain alkyl having from about 10 to about 24 carbon atoms, or $((CH_2)_pO)_q(CH_2)_pV$ where q is an integer from 1 to about 900 and where each p is independently an integer from 2 to about 10 and V is OH, or $O(CH_2)_bCH_3$ where b is an integer from 0 to about 10; Y is O or S; n is an integer from 0 to about 10; and m is an integer from 0 to about 10; or a pharmaceutically acceptable salt thereof.

In another embodiment, LPA has the formula:

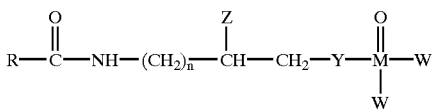

or a cyclic phosphate derivative thereof having the structure:

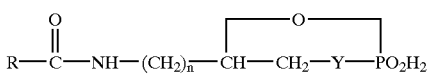

or the reverse amide thereof, wherein Z is OH, SH, $NH_2$, halogen, $OPO_3H_2$, H or $SO_3H$; M is P or S, where when M is S, one W is (=O); each W is independently SH, OH, $OCH_2CH(NH_2)CO_2H$, $OCHCH_3CH(NH_2)CO_2H$, $OPO_3H_2$, or $OPO_2HOPO_3H_2$, where if one W is $OPO_3H_2$ or $OPO_2HOPO_3H_2$, the remaining W is OH; R is an amino acid side chain unsubstituted or a branched amino acid side chain, or an alkylated amino acid side chain, or substituted, saturated or unsaturated, straight or branched-chain alkyl having from about 10 to about 24 carbon atoms, or $((CH_2)_mO)_p(CH_2)_mW$ where p is an integer from 1 to about 900 and where each m is independently an integer from 2 to about 10 and W is OH, or $O(CH_2)_qCH_3$ where q is an integer from 0 to about 10; Y is O or S; and n is an integer from 0 to about 10; or a pharmaceutically acceptable salt thereof.

In specific embodiments of the present invention, R, in the above structures, is an alkyl having between about 10 and about 24 carbon atoms, wherein between 0 and 11, inclusive, of the carbon-carbon bonds are unsaturated, and mixtures thereof, or, more specifically, R is an alkyl having 18 carbon atoms, wherein 1 or 2 of the carbon-carbon bonds are unsaturated, and mixtures thereof.

In one embodiment of the present invention, the composition comprising LPA is a solution and the LPA is present in an amount of from about 0.00001% to about 10% (weight/volume), or, more specifically, 0.00001% to 50% (weight/weight).

In a specific embodiment, where a lipid membrane structure is present, the lipid membrane structure comprises at least one compound selected from the group consisting of lipids, phospholipids and surfactants. In a specific embodiment, the lipid is selected from the group consisting of semi-synthetic or synthetic mono- or di-glycerophospholipids, haloalkyl derivatives thereof, amphipathic steroids, and bolaamphiles. In an additional embodiment, the surfactant is nonionic and is selected from the group consisting of polyoxyethylene derivatives of fatty alcohols, fatty acid esters of fatty alcohols and glyceryl esters wherein the polyoxyethylene group is coupled via an ether linkage to an alcohol group. Alternatively, the phospholipid is selected from the group consisting of monoacyl glyceryl phosphates and diacylglyceryl phosphates. The lipid membrane structure can further comprise a tissue targeting compound, which, in a specific embodiment, is selected from the group consisting of: an antibody, a cell surface receptor, a ligand for a cell surface receptor, a polysaccharide, a drug, a hormone, a hapten, a special lipid and a nucleic acid.

In one embodiment, the composition further comprises a component selected from the group consisting of polypeptides, modified polypeptides and polymers, wherein, in a specific embodiment, the polypeptide is selected from the group consisting of fatty acid binding proteins. In another specific embodiment, the modified polypeptide contains a modification selected from the group consisting of glycosylation, phosphorylation, myristylation, sulfation and hydroxylation. In additional specific embodiments, the polymer is a naturally occurring polymer and is selected from the group consisting of dextrans, hydroxyethyl starch, and polysaccharides, and/or the polysaccharide is selected from the group consisting of trehalose, glucose, maltose, lactose, maltulose, iso-maltulose, lactulose, mono-reducing glycosides of polyhydroxy compounds selected from sugar alcohols, other straight chain polyalcohols, raffinose, stachyose, melezitose, dextran, sucrose and sugar alcohols thereof, maltitol, lactitol, iso-maltulose, palatinit, 2-D-glucopyranosyl-1f6-mannitol and their individual sugar alcohols.

Alternatively, the polymer is synthetic and is selected from the group consisting of polyalkyl glycols, polyoxyethylated polyols, polyvinylpyrrolidone, polyhydroxyethyl methacrylate, polyvinyl alcohols, polyurethane, polytrimethylene glycol, polypropylene glycol, polyacrylic acid, polyethyloxazoline, polyacrylamide, polyphosphazene, poly(lactic acid), poly(glycolic acid), polyamino acids and polymeric mixtures thereof.

In another embodiment of the present invention, the composition comprising LPA further comprises a protein. In specific embodiments, the protein is selected from the group consisting of: a lipid binding protein and a lipid carrier protein, or the group consisting of: albumin, soy and plant protein, cytochrome c, low density lipoprotein, acyl carrier protein, and alphafeto protein. In one embodiment, the protein is a modified protein, specifically, the modified protein can contain a modification selected from the group consisting of glycosylation, phosphorylation, myristylation, sulfation and hydroxylation.

In another embodiment of the present invention, the composition comprising LPA further comprises a polyethylene glycol (PEG). In one embodiment, the weight ratio of PEG to LPA is 1–100,000 to 1, and/or the PEG has an average molecular weight from about 8,000 to about 40,000, preferably 20,000.

In specific embodiments of the present invention, the compositions of the present invention also contain pharmaceutically acceptable excipients, encompassing in one embodiment, without limitation, topical pharmaceutically acceptable carrier, cosmetic carrier, sterile solutions, sterile isotonic solutions, ingestable liquids, pharmaceutically acceptable aerosols and solutions for organ/tissue/cell preservation and/or transplantation.

In specific embodiments of the present invention, the compositions of the present invention also contain pharmaceutically acceptable excipients, encompassing in one embodiment, without limitation, drugs, antibiotics, wound healing agents and antioxidants. In a specific embodiment, the drug is selected from the group consisting of antipyretic and anti-inflammatory, analgesics, antiarthritics, antispasmodics, antidepressants, antipsychotics, tranquilizers, antianxiety drugs, narcotic antagonists, anti-parkinsonism agents, cholinergic antagonists, chemotherapeutic agents, immuno-suppressive agents, antiviral agents, parasiticides, appetite suppressants, antiemetics, antihistamines, antimigraine agents, coronary vasodilators, cerebral vasodilators, peripheral vasodilators, hormonal agents, contraceptives, antithrombotic agents, diuretics, antihypertensive agents, cardiovascular drugs, opioids, and vitamins. In another specific embodiment, the antibiotic is selected from the group consisting of ampicillin, tetracycline, chloramphenicol, erythromycin, amphotericin B and penicillin. In yet another specific embodiment, the wound healing agent is selected from the group consisting of transforming growth factors, platelet-derived growth factors, epidermal growth factors and fibroblast growth factors.

In yet another specific embodiment, the antioxidant is selected from the group consisting of Vitamin C, Vitamin E, Vitamin A, dihydrolipoamide, flavenoids, butylated hydroxytoluene, butylated hydroxyanisole, Trolox®, propyl gallate, phenolic antioxidants, phenothiazines, desferrioxamide, HBED and CP130.

In an additional embodiment of the present invention, the composition is in aqueous solution and the aqueous solution is in a pH range of from about 2–10, or preferably 4 to about 8.

The present invention further encompasses methods of making the LPA containing composition, comprising the steps of: forming a lipid dispersion comprising LPA; providing at least one of said components; and combining the products of steps a) and b). In aspecific embodiment, the lipid dispersion is formed by the steps of: a) dissolving LPA and any other lipids in organic solvent; b) removing the solvent to form dried lipid; and c) dispersing the dried lipid into aqueous media by the steps of: i) forming an even lipid dispersion; and ii) forming an even dispersion of lipid membrane structures. In specific embodiments, the dispersion is formed by a method selected from the group consisting of sonication, microfluidization, extrusion, and detergent dialysis. The method can further comprise the step of d) sterilizing the dispersion. The sterilization can be by any known method, including steam sterilization. In a preferred method, the sterile filter pore size is about 0.45 micron or smaller, and/or the dispersion has a particle size of from about 3–450 nm. In a specific embodiment, the method further comprises the step of c)i) sterilizing the dispersion, which can be, without limitation, by steam sterilization, which is preferably under anoxic conditions.

Also encompassed by the present invention is a composition obtained according to the above described method.

The present invention further encompasses methods of treating apoptosis or preserving or restoring function, in a cell, tissue or organ, comprising administering a therapeutically effective amount of a pharmaceutically acceptable composition comprising lysophosphatidic acid or an analog thereof (LPA).

In specific embodiments, the pharmaceutically acceptable composition further comprises a potentiating component, such as a polyethylene glycol; a protein; or a lipid membrane structure.

In additional embodiments, the composition is administered to a patient suffering from a condition related to any one of the following: apoptosis, ischemia, traumatic injury or reperfusion damage, gastrointestinal perturbation (wherein, in one embodiment, the gastrointestinal perturbation is caused by a stimulus selected from the group consisting of viruses (including human immunodeficiency virus), chemotherapeutic agents, radiation, infectious diseases, inflammatory bowel disease, and diarrhea-causing organisms.

Preferably, the method diminishes apoptosis-related problems associated with immunosuppressing viruses, chemotherapeutic agents, or radiation and immunosuppressive drugs.

In one embodiment, the reperfusion damage is associated with coronary artery obstruction; stroke; cerebral infarction; spinal/head trauma and concomitant severe paralysis; frostbite; coronary angioplasty; blood vessel attachment; limb attachment; organ attachment; and kidney reperfusion.

In a specific embodiment, the LPA used in the above method has one of the following structures:

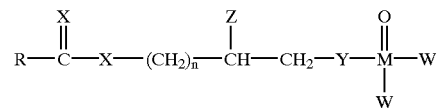

or a cyclic phosphate derivative thereof having the structure:

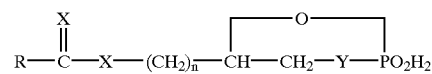

wherein each X is independently O or S; M is P or S, where when M is S, one W is (=O); each W is independently SH, OH, $OCH_2CH(NH_2)CO_2H$, $OCHCH_3CH(NH_2)CO_2H$, $OPO_3H_2$, or $OPO_2HOPO_3H_2$, where if one W is $OPO_3H_2$ or $OPO_2HOPO_3H_2$, the remaining W is OH; Z is OH, SH, $NH_2$, halogen, $OPO_3H_2$, H, $O(CH_2)_bCH_3$ where b=0 to about 2, or $SO_3H$; R is unsubstituted or substituted, saturated or unsaturated, straight or branched-chain alkyl having from about 10 to about 24 carbon atoms, or $((CH_2)_mO)_p(CH_2)_mW$ where p is an integer from 1 to about 900 and where each m is independently an integer from 2 to about 10 and W is OH, or $O(CH_2)_qCH_3$ where q is an integer from 0 to about 10; Y is O or S; and n is an integer from 0 to about 10; or a pharmaceutically acceptable salt thereof; or

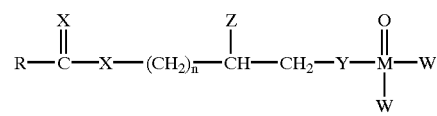

or a cyclic phosphate derivative thereof having the structure:

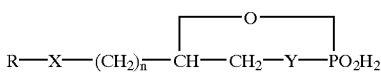

wherein X is O, S, or $CH_2$; M is P or S, where when M is S, one W is (=O); each W is independently SH, OH, $OCH_2CH(NH_2)CO_2H$, $OCHCH_3CH(NH_2)CO_2H$, $OPO_3H_2$, or $OPO_2HOPO_3H_2$, where if one W is $OPO_3H_2$ or $OPO_2HOPO_3H_2$, the remaining W is OH; Z is OH, SH, $NH_2$, halogen, $OPO_3H_2$, H or $SO_3H$; R is unsubstituted or substituted, saturated or unsaturated, straight or branched-chain alkyl having from about 10 to about 24 carbon atoms, or $((CH_2)_mO)_p(CH_2)_mW$ where p is an integer from 1 to about 900 and where each m is independently an integer from 2 to about 10 and W is OH, or $O(CH_2)_qCH_3$ where q is an integer from 0 to about 10; Y is O or S; and n is an integer from 0 to about 10; or a pharmaceutically acceptable salt thereof; or

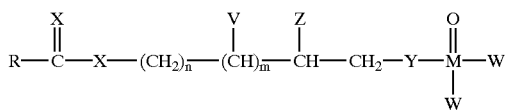

or a cyclic phosphate derivative thereof having the structure:

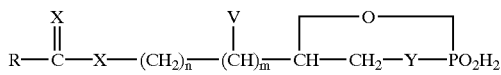

wherein each V is independently OH, SH, H, $NH_2$, halogen, $OPO_3H_2$, or $OSO_3H$; each X is independently O or S; M is P or S, where when M is S, one W is (=O); each W is independently SH, OH, $OCH_2CH(NH_2)CO_2H$, $OCHCH_3CH(NH_2)CO_2H$, $OPO_3H_2$, or $OPO_2HOPO_3H_2$, where if one W is $OPO_3H_2$ or $OPO_2HOPO_3H_2$, the remaining W is OH; Z is OH, SH, $NH_2$, halogen, $OPO_3H_2$, H or $SO_3H$; R is unsubstituted or substituted, saturated or unsaturated, straight or branched-chain alkyl having from about 10 to about 24 carbon atoms, or $((CH_2)_pO)_q(CH_2)_pV$ where q is an integer from 1 to about 900 and where each p is independently an integer from 2 to about 10 and V is OH, or $O(CH_2)_bCH_3$ where b is an integer from 0 to about 10; Y is O or S; n is an integer from 0 to about 10; and m is an integer from 0 to about 10; or a pharmaceutically acceptable salt thereof; or

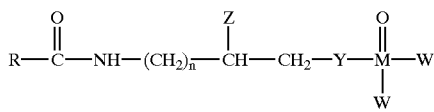

or a cyclic phosphate derivative thereof having the structure:

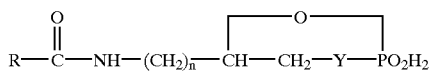

or the reverse amide thereof, wherein Z is OH, SH, $NH_2$, halogen, $OPO_3H_2$, H or $SO_3H$; M is P or S, where when M is S, one W is (=O); each W is independently SH, OH, $OCH_2CH(NH_2)CO_2H$, $OCHCH_3CH(NH_2)CO_2H$, $OPO_3H_2$, or $OPO_2HOPO_3H_2$, where if one W is $OPO_3H_2$ or $OPO_2HOPO_3H_2$, the remaining W is OH; R is an amino acid side chain unsubstituted or a branched amino acid side chain, or an alkylated amino acid side chain, or substituted, saturated or unsaturated, straight or branched-chain alkyl having from about 10 to about 24 carbon atoms, or $((CH_2)_mO)_p(CH_2)_mW$ where p is an integer from 1 to about 900 and where each m is independently an integer from 2 to about 10 and W is OH, or $O(CH_2)_qCH_3$ where q is an integer from 0 to about 10; Y is O or S; and n is an integer from 0 to about 10; or a pharmaceutically acceptable salt thereof.

In specific embodiments of the present invention, R, in the above structures, is an alkyl having between about 10 and about 24 carbon atoms, wherein between 0 and 11, inclusive, of the carbon-carbon bonds are unsaturated, and mixtures thereof, or more specifically, R is an alkyl having 18 carbon atoms, wherein 1 or 2 of the carbon-carbon bonds are unsaturated, and mixtures thereof.

Also encompassed by methods of the present invention are methods of culturing cells comprising treating cells with an amount of a composition of the present invention effective to prevent apoptosis and/or preserve the cells.

In a specific embodiment, the cells are selected from the group consisting of human, plant, bacterial, yeast and fungus, and/or the cells are part of a tissue or organ.

Also encompassed by methods of the present invention are methods of preserving an organ comprising adding an effective amount of the composition of the present invention to the solution with which the organ is treated, or, alternatively, administering to the host animal at least one intravenous bolus of an effective amount of the composition, or administering, to the recipient of an organ transplant, an amount of the composition effective to enhance function of the transplanted organ.

Also encompassed by the present invention are methods of treating a patient comprising administering to the patient a therapeutically effective amount of a composition of the present invention.

Also encompassed by the present invention are methods of treating dermatologic conditions, comprising topically administering a therapeutically effective amount of a pharmaceutically acceptable composition comprising the composition comprising an LPA and a potentiating component to a patient in need of such treatment. In a specific embodiment, the dermatological condition is wrinkling, or hair loss.

Also encompassed by the present invention are methods of treating wounds comprising administering an effective amount of the composition comprising an LPA, wherein, in a specific embodiment, the wounds are burn wounds.

Also encompassed by the present invention are methods of treating apoptosis, preserving or restoring function in a cell, tissue or organ comprising administering internally or in vitro a therapeutically effective amount of a pharmaceutically acceptable composition comprising lysophosphatidic acid or an analog thereof (LPA) to cells. In specific embodiments, the composition is a solution and the LPA is present in an amount of from about 0.00001% to about 10% (weight/volume), or the composition is a solid and the LPA is present in an amount of from about 0.00001% to 50% (weight/weight).

In one embodiment, the cells treated by compositions of the present invention are cardiac cells and the composition is delivered by intracoronary administration to said cardiac cells.

The present invention also encompasses compositions comprising: a compound of the following formula

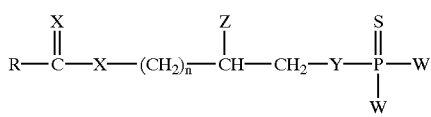

or a cyclic phosphate derivative thereof having the structure:

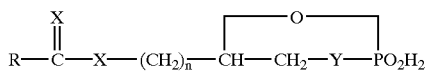

wherein each X is independently O or S; each W is independently SH, OH, $OCH_2CH(NH_2)CO_2H$, $OCHCH_3CH(NH_2)CO_2H$, $OPO_3H_2$, or $OPO_2HOPO_3H_2$, where if one W is $OPO_3H_2$ or $OPO_2HOPO_3H_2$, the remaining W is OH; Z is OH, SH, $NH_2$, halogen, $OPO_3H_2$, H, $O(CH_2)_bCH_3$ where b=0 to about 2, or $SO_3H$; R is unsubstituted or substituted, saturated or unsaturated, straight or branched-chain alkyl having from about 10 to about 24 carbon atoms, or $((CH_2)_mO)_p(CH_2)_mW$ where p is an integer from 1 to about 900 and where each m is independently an integer from 2 to about 10 and W is OH, or $O(CH_2)_qCH_3$ where q is an integer from 0 to about 10; Y is O or S; and n is an integer from 0 to about 10; or a salt thereof.

The present invention specifically encompasses the following compositions: 3-O-Oleoyl-2-O-methyl-rac-glycero-1-thiophosphate, or a salt thereof; Oleyl 1-thiophosphoryl-2-O-methyl-rac-glycerate, or a salt thereof; and 3-O-Oleyl-2-O-methyl-rac-glycero-1-thiophosphate, or a salt thereof.

Methods of treating apoptosis, preserving or restoring function in a cell, tissue or organ comprising administering internally or in vitro a therapeutically effective amount of a pharmaceutically acceptable composition comprising any of these compositions is also encompassed by the present invention.

BRIEF DESCRIPTION OF THE DRAWINGS

In FIGS. 2–8, the white bars represent adherent cells and the dark bars represent non-adherent cells. The following list provides the compositions represented by each column:
1 BME
2 Five Phospholipid Mixture (0.25 μg/ml LPA)
3 Five Phospholipid Mixture (0.75 μg/ml LPA)
4 Five Phospholipid Mixture (2.25 μg/ml LPA)
5 Five Phospholipid Mixture (6.75 μg/ml LPA)
6 10% LPA in PG 0.25 μg/ml
7 10% LPA in PG 0.75 μg/ml
8 10% LPA in PG 2.25 μg/ml
9 10% LPA in PG 6.75 μg/ml
10 PG only 67.5 μg/mL
11 10% LPA in PG/5% PE-PEG 0.25 μg/ml
12 10% LPA in PG/5% PE-PEG 0.75 μg/ml
13 10% LPA in PG/5% PE-PEG 2.25 μg/ml
14 10% LPA in PG/5% PE-PEG 6.75 μg/ml
15 PG/5% PE-PEG only 67.5 μg/ml
16 PG/5% PE-PEG only 22.5 μg/ml
17 10% LPA in PG/10% PE-PEG 0.25 μg/ml
18 10% LPA in PG/10% PE-PEG 0.75 μg/ml
19 10% LPA in PG/10% PE-PEG 2.25 μg/ml
20 10% LPA in PG/10% PE-PEG 6.75 μg/ml
21 PG/10% PE-PEG only 67.5 μg/ml
22 PG/10% PE-PEG only 22.5 μg/ml
23 10% LPA in PC 0.25 μg/ml
24 10% LPA in PC 0.75 μg/ml
25 10% LPA in PC 2.25 μg/ml
26 10% LPA in PC 6.75 μg/ml
27 PC only 67.5 μg/ml
28 PC only 22.5 μg/ml
29 10% LPA in PC/TAP 0.25 μg/ml
30 10% LPA in PC/TAP 0.75 μg/ml
31 10% LPA in PC/TAP 2.25 μg/ml
32 10% LPA in PC/TAP 6.75 μg/ml
33 PC/TAP only 67.5 μg/ml
34 PC/TAP only 22.5 μg/ml
35 10% LPA in PS 0.25 μg/ml
36 10% LPA in PS 0.75 μg/ml
37 10% LPA in PS 2.25 μg/ml
38 10% LPA in PS 6.75 μg/ml
39 PS only 67.5 μg/ml
40 BME only
FIG. 3 is a bar graph depicting protection of serum-deprived C3H/10T½ cells by Five Phospholipid Mixture and 18:1-LPA formulations in phosphotidyl glycerol (PG) and phosphotidyl glycerol/phosphotidylcholine (PG/PC) membrane structures.

FIG. 4 is a bar graph depicting protection of serum-deprived C3H/10T½ cells by 18:1-LPA and lysophosphotidylserine (LPS).

FIG. 5 is a bar graph depicting protection of C3H/10T½ cells from serum-deprivation by soy-derived, 18:1 and 16:0 LPA.

FIG. 6 is a bar graph depicting C3H/10T½ cell protection from serum-deprivation by 18:1 LPA and 18:0 LPA alone or in PG membrane structures.

FIG. 7 is a bar graph depicting protection of C3H/10T½ cells from serum-deprivation by lysophosphatidic acid incorporated at different concentrations into. Phosphatidic acid (PA)/phosphatidylinositol (PI) (1:1) membrane structures. Controls include concentrations of 0.3, 1, 3, and 10 μg/ml of the Five Phospholipid Mixture (referred to in figure as "Elirex").

FIG. 8 is a bar graph depicting protection of serum-deprived C3H/10T½ cells by 18:1-LPA in Five Phospholipid Mixture (labeled "Elirex") and PC or chemically modified PC membrane structures.

FIG. 15 is a compilation of photomicrographs showing the prevention of ceramide-induced cardiomyocyte death by Five Phospholipid Mixture and mixtures of Five Phospholipid Mixture and PEG. Pictures A-F contained 10 µM ceramide and 0.3% PEG (B), 2% PEG (C), 5 µM LPA presented as Five Phospholipid Mixture (D), 5 µM Five Phospbolipid Mixture plus 0.4% PEG (E), and 5 µM LPA presented as Five Phospholipid Mixture plus 2% PEG (F). Picture G contained only serum and glucose and no active ingredients. Pictures H–M contain 15 µM ceramide and 0.3% PEG I, 2% PEG (J), 5 µM LPA presented as Five Phospholipid Mixture (K), 5 µM LPA presented as Five Phospholipid Mixture, plus 0.4% PEG (L), and 5 µM LPA presented as Five Phospholipid Mixture plus 2% PEG (M).

MODES FOR CARRYING OUT THE INVENTION

Figure 1:
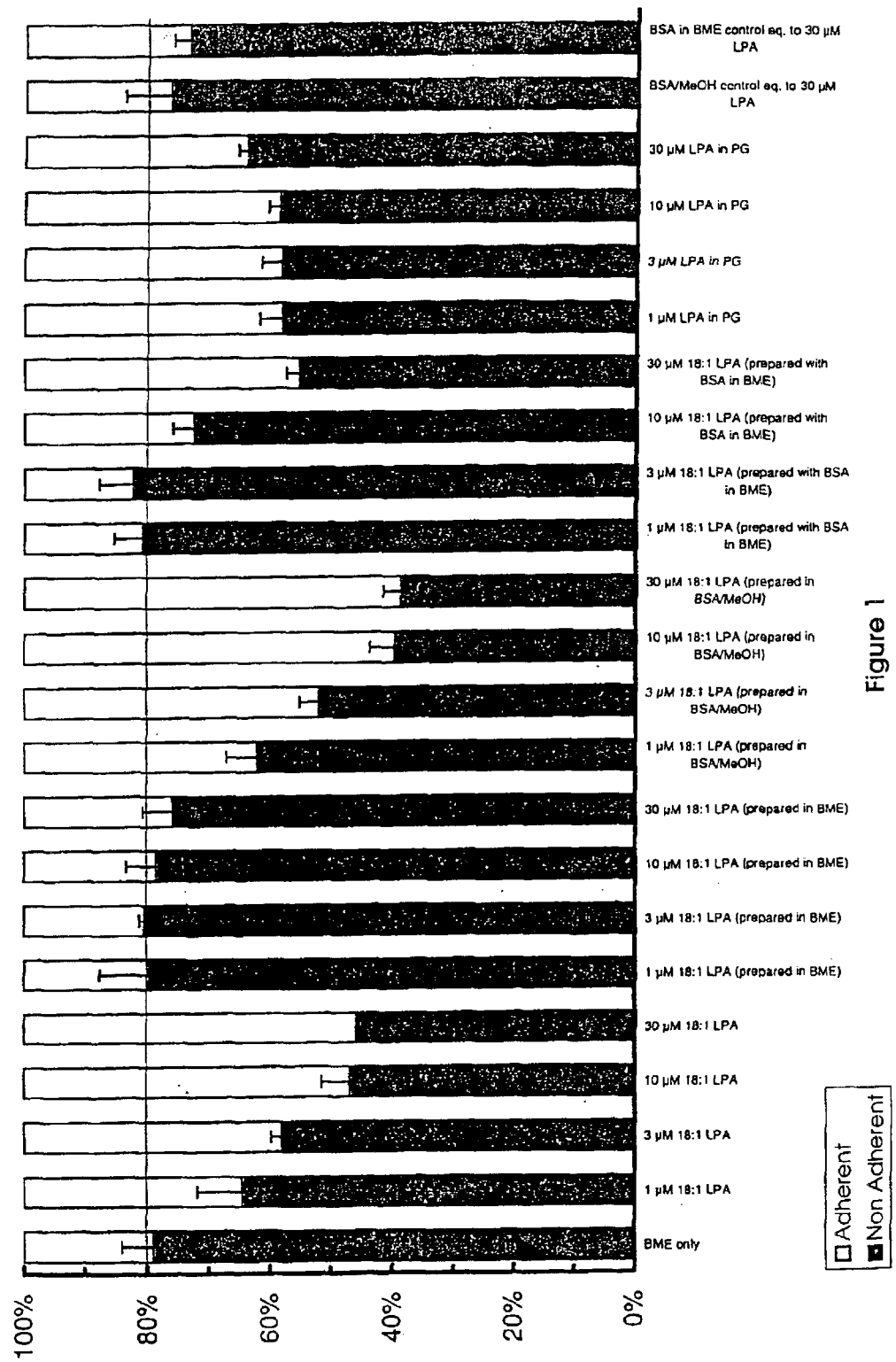
FIG. 1 is a bar graph depicting the effect of various concentrations of 18:1-LPA analog on protection of C3H/10T½ cells from serum deprivation. LPA was prepared with or without a potentiating component (bovine serum albumin or phosphatidyl glycerol vesicles). The shaded section of the bars represents adherent cells and the solid section of the bars represents non-adherent cells. Where not specified as a particular analog, "LPA" refers to 18:1-LPA in all figures.

It was previously found that compositions containing an extract derived from plants is capable of producing an anti-apoptotic effect as measured in in vitro cell assays designed to respond to an apoptosis signal. PCT WO 95/15173; and U.S. Pat. No. 5,567,425. These compositions were shown to prevent diarrhea and weight loss in animals treated with methotrexate, indicating that the in vitro anti-apoptosis activity is correlated with similar in vivo activity. The active ingredients of these anti-apoptotic compositions were found to be in the combination of the phospholipids phosphatidic acid (PA); phosphatidylinositol (PI); lysophosphatidic acid (an LPA); lysophosphatidylinositol (LPI); and lysophosphatidylcholine (LPC). Compositions containing various concentrations of these phospholipids and methods of making and using the compositions are described in detail in PCT/US96/14752. These compositions are readily obtainable from a variety of sources, including plants, animals and combinations of isolated or synthetic phospholipids. The phospholipids can also be prepared synthetically by methods known in the lipid synthesis art. Unfortunately, extracting or combining these 5 phospholipids can be time consuming and the mixture itself is not readily available in the desired ratios.

It has now been found that lysophosphatidic acid is the major active component of these phospholipid mixtures. A benefit in this discovery lies in the ability to easily obtain and formulate compositions containing this active ingredient. Surprisingly, certain combinations of the phospholipids and combinations with other compositions have been found to exhibit increased anti-apoptotic activity. This invention encompasses methods of use of therapeutically effective compositions containing lysophosphotidic acid, its analogs and derivatives (collectively "LPA"), which have been found to exhibit anti-apoptotic activity and to preserve or restore cell, tissue and organ function.

"Treating apoptosis" is herein defined as administering to a cell, tissue, organ or organism exhibiting apoptosis, or at risk of apoptosis, a treatment to effect beneficial or desired clinical results, including, but not limited to preventing or diminishing apoptosis.

The present invention provides methods of use wherein LPA acts alone or in combination with a potentiating component, as described in more detail below.

LPA shows activity in the preservation or restoration of cell, tissue and organ function both alone and in the presence of a potentiating component, including, but not limited to other phospholipids, proteins and polyethylene glycols (PEG).

I. Compounds of the Present Invention

Although phospholipid structures are well defined in the literature, they can vary with respect to lipid chain length and saturation. "Lysophosphotidic acids" or "LPAs" as used herein shall encompass the following structures and descriptions and will also include related structures known in the art provided they are effective in producing therapeutic response.

A. Structures of Compounds of the Present Invention.

LPA has the following general structure:

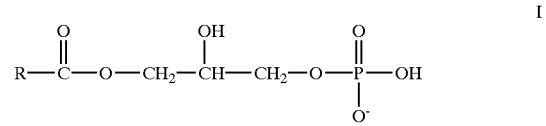

An LPA is an acid in which only one of the hydroxyl groups of the glycerol is esterified to a fatty acid. LPA is a phosphatidic acid in which the 2 carbon is not esterified and the 3 carbon is bound to the O—PO$_3$H$_2$ group, or, in the case of the salt, one or more hydrogens are replaced, for example with Na$^+$. The 1 carbon will contain an acyl ester of fatty acids.

The term "UB" is used in reference to the various structures herein to describe the number of unsaturated carbon atoms in R. For example, if R is 18 and UB is 1, R contains 18 carbon atoms, with 1 unsaturated bond. Some LPA analogs are also referred to herein as R:UB-LPA (i.e. 18:1-LPA, wherein R is 18 carbon atoms with 1 unsaturated bond).

As used herein, LPA includes LPA having any one of a variety of fatty acids esterified at the C1 position. Examples include LPA wherein the fatty acid ester is lauryl, myristyl, palmityl, stearyl, palmitoleyl, oleyl or linoleyl. (In structure I, above, the composition where R is 18 and UB is 1, shall herein be referred to as "18:1-LPA"). For a representative example of suitable phospholipids see any chemical catalog of a phospholipid supplier, for instance, the (1994) Avanti Polar Lipids Inc. catalog, particularly pages 14 and 21.

R can be an unsubstituted or substituted, saturated or unsaturated, straight or branched chain alkyl having from about 10 to about 24 carbon atoms. For all of the structures referenced herein, R can have between 0 and (n−2)/2 unsaturated bonds, wherein n is the number of carbon atoms in R. Substitutions include, but are not limited to, halogen, hydroxy, phenyl, amino or acylamino.

As used herein, "LPA" encompasses LPA analogs. Given the examples provided herein, it can be determined readily if an LPA analog exerts sufficient anti-apoptotic activity to be suitable for medical use. A wide variety of LPA analogs are known in the art and many of these can be purchased from commercial sources such as Avanti Polar Lipids Inc. (Alabaster, Ala.), or they can be synthesized by methods known in the art.

LPA analogs include, but are not limited to, the following structures:

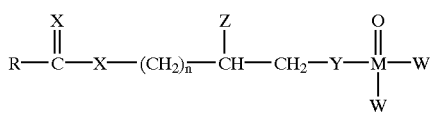

II or a cyclic phosphate derivative thereof having the structure:

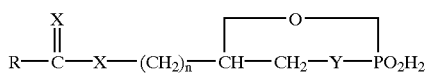

III or pharmaceutically acceptable salts thereof, wherein each X is independently O or S; M is P or S, where when M is S, one W is (=O); each W is independently SH, OH, $OCH_2CH(NH_2)CO_2H$ and $OCHCH_3CH(NH_2)CO_2H$; each W is independently SH, OH, $OCH_2CH(NH_2)CO_2H$, $OCHCH_3CH(NH_2)CO_2H$, $OPO_3H_2$, or $OPO_2HOPO_3H_2$, where if one W is $OPO_3H_2$ or $OPO_2HOPO_3H_2$, the remaining W is OH; Z is OH, SH, $NH_2$, halogen, $OPO_3H_2$, H, $O(CH_2)_bCH_3$ where b=0 to about 2, or $SO_3H$; R is unsubstituted or substituted, saturated or unsaturated, straight or branched-chain alkyl having from preferably 5–7, more preferably 8–10 and most preferably, about 10 to preferably 24–30, more preferably 24–28 and most preferably about 24 carbon atoms, or $((CH_2)_mO)_p(CH_2)_mW$ where p is an integer from 1 to about 900 and where each m is independently an integer from 2 to about 10 and W is OH, or $O(CH_2)_qCH_3$ where q is an integer from 0 to about 10; Y is O or S; and n is an integer from 0 to about 10. Preferably, R is between about 10 and 24, UB is 0–11, and mixtures thereof. More preferably, R is between about 14 and 20, UB is 0–6, and mixtures thereof. Even more preferably, R is between about 16 and 18, UB is 0–3, and mixtures thereof. Most preferably, R is 18, UB is 1 or 2, and mixtures thereof.

Methods of preparation of substitutions at the phosphate group of LPA have been described, and are included herein. Tokumura et al. (1981) *J. Pharm. Exp. Therap.* 219:219–224.

Also included in LPA analogs are ethers and thioethers at the C1 position having the structure:

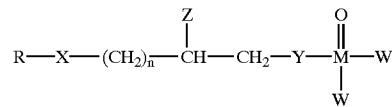

IV or a cyclic phosphate derivative thereof having the structure:

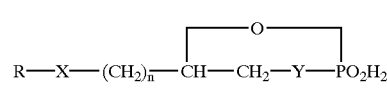

V or pharmaceutically acceptable salts thereof, wherein X is O, S, or $CH_2$; M is P or S, where when M is S, one W is (=O); each W is independently SH, OH, $OCH_2CH(NH_2)CO_2H$ and $OCHCH_3CH(NH_2)CO_2H$; each W is independently SH, OH, $OCH_2CH(NH_2)CO_2H$, $OCHCH_3CH(NH_2)CO_2H$, $OPO_3H_2$, or $OPO_2HOPO_3H_2$, where if one W is $OPO_3H_2$ or $OPO_2HOPO_3H_2$, the remaining W is OH; Z is OH, $CH_2OH$, SH, $NH_2$, halogen, $OPO_3H_2$, H or $SO_3H$; R is unsubstituted or substituted, saturated or unsaturated, straight or branched-chain alkyl having from preferably 5–7, more preferably 8–10 and most preferably, about 10 to preferably 24–30, more preferably 24–28 and most preferably about 24 carbon atoms, or $((CH_2)_mO)_p(CH_2)_mW$ where p is an integer from 1 to about 900 and where each m is independently an integer from 2 to about 10 and W is OH, or $O(CH_2)_qCH_3$ where q is an integer from 0 to about 10; Y is O or S; and n is an integer from 0 to about 10. Simon et al. (1982) *Biochem. Biophys. Res. Comm.* 108:1743–1750.

Preferably, R is between about 10 and 24, UB is 0–11, and mixtures thereof. More preferably, R is between about 14 and 20, UB is 0–6, and mixtures thereof. Even more preferably, R is between about 16 and 18, UB is 0–3, and mixtures thereof. Most preferably, R is 18, UB is 1 or 2, and mixtures thereof.

Also included are glycero LPA analogs having the structure:

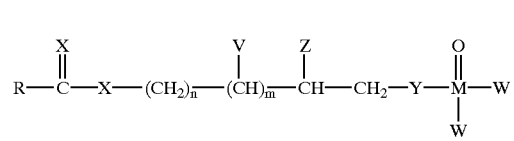

VI or a cyclic phosphate derivative thereof having the structure:

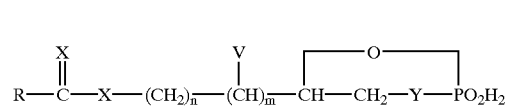

VII or pharmaceutically acceptable salts thereof, wherein each V is independently OH, SH, H, $NH_2$, halogen, $OPO_3H_2$, or $OSO_3H$; each X is independently O or S; M is P or S, where when M is S, one W is (=O); each W is independently SH, OH, $OCH_2CH(NH_2)CO_2H$ and $OCHCH_3CH(NH_2)CO_2H$; each W is independently SH, OH, $OCH_2CH(NH_2)CO_2H$, $OCHCH_3CH(NH_2)CO_2H$, $OPO_3H_2$, or $OPO_2HOPO_3H_2$, where if one W is $OPO_3H_2$ or $OPO_2HOPO_3H_2$, the remaining W is OH; Z is OH, SH, $NH_2$, halogen, $OPO_3H_2$, H or $SO_3H$; R is unsubstituted or substituted, saturated or unsaturated, straight or branched-chain alkyl having from preferably 5–7, more preferably 8–10 and most preferably, about 10 to preferably 24–30, more preferably 24–28 and most preferably about 23 carbon atoms, or $((CH_2)_pO)_q(CH_2)_pV$ where q is an integer from 1 to about 900 and where each p is independently an integer from 2 to about 10 and V is OH, or $O(CH_2)_bCH_3$ where b is an integer from 0 to about 10; Y is O or S; n is an integer from 0 to about 10; and m is an integer from 0 to about 10. Preferably, R is between about 10 and 24, UB is 0–11, and mixtures thereof. More preferably, R is between about 14 and 20, UB is 0–6, and mixtures thereof. Even more preferably, R is between about 16 and 18, UB is 0–3, and mixtures thereof. Most preferably, R is 18, UB is 1 or 2, and mixtures thereof.

Also included are LPA analogs containing an amide bond and having the structure:

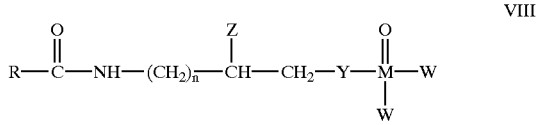

VIII or a cyclic phosphate derivative thereof having the structure:

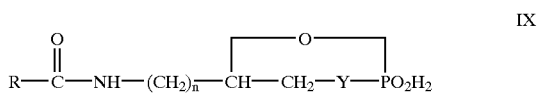

IX or the reverse amide [structures VIII and IX, having R—NH—C(=O)—$(CH_2)_n$— in place of R—C(=O)—NH—$(CH_2)_n$—](NH—$CH_2)_n$—] or pharmaceutically acceptable salts thereof, wherein Z is OH, SH, $NH_2$, halogen, $OPO_3H_2$, H or $SO_3H$; M is P or S, where when M is S, one W is (=O); each W is independently SH, OH, $OCH_2CH(NH_2)CO_2H$ and $OCHCH_3CH(NH_2)CO_2H$; each W is independently SH, OH, $OCH_2CH(NH_2)CO_2H$, $OCHCH_3CH(NH_2)CO_2H$, $OPO_3H_2$, or $OPO_2HOPO_3H_2$, where if one W is $OPO_3H_2$ or $OPO_2HOPO_3H_2$, the remaining W is OH; R is an amino acid side chain or a branched amino acid side chain, or an alkylated amino acid side chain, unsubstituted or substituted, saturated or unsaturated, straight or branched-chain alkyl having from preferably 5–7, more preferably 8–10 and most preferably, about 10 to preferably 24–30, more preferably 24–28 and most preferably about 23 carbon atoms, or $((CH_2)_mO)_p(CH_2)_mW$ where p is an integer from 1 to about 900 and where each m is independently an integer from 2 to about 10 and W is OH, or $O(CH_2)_qCH_3$ where q is an integer from 0 to about 10; Y is O or S; and n is an integer from 0 to about 10. Preferably, R is between about 10 and 24, UB is 0–11, and mixtures thereof. More preferably, R is between about 14 and 20, UB is 0–6, and mixtures thereof. Even more preferably, R is between about 16 and 18, UB is 0–3, and mixtures thereof. Most preferably, R is 18, UB is 1 or 2, and mixtures thereof.

In all analogs containing W, it is preferred that W is not ethanolamine, glycerol, or choline.

In the above structures, where one W is SH, some molecules will exist as resonance structures, alternating between the (=O) and (=S) structures.

Naturally occurring derivatives are also encompassed in the term "LPA." Such derivatives include, but are not limited to, PHYPLA or cLPA. Murakami-Murofushi et al. (1992) *J. Biol. Chem.* 267:21512–21517. Cyclic derivatives can also be synthesized by methods known in the art.

Pharmaceutically acceptable salts of the phospholipids encompassed by the present invention, include, but are not limited to, the free acid form, alkali metal salts, such as sodium and potassium; alkaline earth metal salts, such as calcium and magnesium; non-toxic heavy metal salts; ammonium salts; trialkylammonium salts, such as trimethylammonium and triethylammonium; and alkoxyammonium salts, such as triethanolammonium, tri(2-hydroxyethyl) ammonium, and tromethamine (tris(hydroxymethyl) aminomethane). Particularly preferred are sodium and ammonium salts.

B. Obtaining Compounds of the Present Invention

The phospholipids can be obtained from any source including, but not limited to, commercial, isolated from a variety of different plants (including plant organs) and animals or created synthetically. Preferably the plants are in the soybean family, but the phospholipids can be isolated from other plants including, but not limited to, those in the *leguminosae* (beans and peas etc.). The phospholipids can also be isolated from partially purified plant extracts including, but not limited to, soy molasses, lecithin (fluid, deoiled or other forms), partially purified protein concentrates, partially purified protein hydrolysates, defatted soy flakes, refined soy oils, soy grits, soy flours and other soy fractions from which lipids can be extracted. It is within the skill of one in the art, utilizing the methods described herein, to determine whether the phospholipids of the present invention can be isolated from a particular species of plant, plant extract or organ within a plant. In addition, U.S. Pat. No. 3,365,440 describes extraction of lipids from soybeans. U.S. Pat. Nos. 5,567,425; 5,602,885; 5,624,675; 5,635,186; 5,635,187 have further general descriptions of a variety of techniques useful for the present invention.

The phospholipids can be obtained from plant sources by any method known in the art provided it results in purification of at least one of the phospholipids of the invention. A variety of methods are known in the art for purifying and analyzing phospholipids from plant sources. For review, see Bligh and Dyer (1959) *Can. J. Biochem. Physiol.* 37:911–917; Patton et al. (1982) *J. Lipid Res.* 23:190–196; Jungalwala (1985) Recent Developments in Techniques for Phospholipid Analysis, in Phospholipids in Nervous Tissues (ed. Eichberg) John Wiley and Sons, pp. 1–44; Hamilton et al. (1992) in the series. A Practical Approach (Rickwood et al. eds.) IRL Press at Oxford University Press; and Kates (1986) Techniques of Lipidology: Isolation, Analysis and Identification in Laboratory Techniques in Biochemistry and Molecular Biology (Burdon et al. eds.) Elsevier.

Phospholipids can also be derived from animal sources. Preferably, the animal is a mammal. Even more preferably, the phospholipids are derived from liver cells. Such phospholipids are commercially available or can be purified from animal tissue by methods known in the art, for instance from animal and egg lecithin or from the compositions described in WO 95/15173. Phospholipids in general, and LPAs in particular, can also be derived from blood.

The phospholipids of the invention can also be synthesized by methods known in the art. Suitable semi-synthetic phospholipids and their synthesis are described in Kates, Techniques of Lipidology (1972).

A synthesis of lysophosphatidic acid is described in W. Stoffel and G. D. Wolf, Chemische Synthese von 1-O-[3H] Palmitoyl-L-glycerin-3-phosphate (L-3-Lysophosphatids äure), *Chem. Ber.*, 347 (1966) 94–101.

The synthesis of various cyclic phosphate LPAs is described in A. J. Slotboom, et al., Synthesis of Lysophosphoglycerides, *Chem. Phys. Lipids*, 1 (1967)

317–336; PCT Publication No. WO 92/21323; and U.S. Pat. No. 5,565,439.

The synthesis of a phosphonate analog of 1-O-hexadecyl-2-O-methyl-glycero-phosphate is described in Z. Li, et al., Phosphonate isosteres of phospholipids, *Tetrahedron Lett.*, 34 (1993) 3539–3542.

Procedures for synthesis of functionalized glycerol ether derivatives which can be used in the synthesis of compounds suitable for use in the present invention are described in K. Agarwal, et al. Synthesis of carbamyl and ether analogs of phosphatidylcholines, *Chem. Phys. Lipids*, 39 (1984) 169–177, and H. Eibl and P. Woolley, A general synthetic method for enantiomerically pure ester and ether lysophospholipids, *Chem. Phys. Lipids*, 47 (1988) 63–68.

The preparation of 1-O-benzyl-2-deoxy-2-bromo glycerol, a starting material for the synthesis of 2-bromo LPA Compound 37, is described in W. L. F. Armarego, B. A. Milloy and W. Pendergast, A highly stereospecific synthesis of (R)- and (S)-[2-2H1]glycine, J. C. S. Perkin I, (1976) 2229–2237.

The synthesis of 2-deoxy-2-bromo-phosphatidylcholine is described in C. J. Lacey and L. M. Loew, Phospholipid synthesis based on new sequential phosphate and carboxylate ester bond formation steps, *J. Org. Chem.*, 48 (1983) 5214–5221.

The synthesis of bisphosphatidic acid and its conversion to bis-lysophosphatidic acid using phospholipase A2 from pig pancreas is described in Q. Quan Dang, et al., Synthesis and identification of bis(diacylglycero)phosphoric acid and bis(monoacylglycero)phosphoric acid, *Lipids*, 17 (1982) 798–802, and Q. Quan Dang and L. Douste-Blazy, Synthesis and stereochemical study of some biologically relevant phosphoglycerides: dicarboxylic phosphatidyl cholines and bis(diacylglycero)phosphoric acids, *Phosphorus and Sulfur,* 18 (1983) 377–380.

A method for the preparation of lysophosphatidic acid or lysophosphatidates by reacting glycidyl esters with anhydrous phosphoric acid is described in U.S. Pat. No. 3,423,440.

A synthesis of lysothiophosphatidic acid is described in N. V. Heeb and K. P. Nambiar, Synthesis of (R)-lysothiophosphatidic acid and (R)-thiophosphatidic acid, *Tetrahedron Lett.*, 34 (1993) 6193–6196

The preparation of LPA amide analogs and 2-deoxy LPA plus various derivatives is described in D. W. Hopper, et al., Facile synthesis of lysophospholipids containing unsaturated fatty acid chains, *Tetrahedron Lett.*, 37 (1996) 7871–7874; and K. R. Lynch, et al., Structure/activity relationships in lysophosphatidic acid: the 2-hydroxyl moiety, *Mol. Pharmacol.*, 52 (1997) 75–81.

The following papers describe synthetic routes which can be used for the synthesis of additional LPA analogs: M. Fuji, et al., A stereoselective and highly practical synthesis of cytosolic phospholipase A2 substrate, 2-S-arachidonoyl-1-O-hexadecyl-sn-thioglycero-3-O-phosphocholine, *J. Org. Chem.*, 62 (1997) 6804–6809; (Strategy for the preparation of 2-thioglycero phosphocholines and guidance for the synthesis of 2-deoxy-2-thiol LPA); and A. Markowska, et al., Etheranaloge der Thio-und Dithiophospholipide mit C-S-P-Bindung, *Liebigs Ann. Chem.*, (1993) 1327–1329 (synthesis of 1-O-hexadecyl-2-O-methyl-3-thioglycero-3-phosphocholine and 1-S-hexadecyl-2-O-methyl-1,3-dithioglycero-3-phosphocholine, guidance for the preparation of LPA analogs containing sulfur linked phosphates).

Various degrees of purity of the phospholipids can be used. Purity can be assayed by any method known in the art such as two dimensional TLC or HPLC and assayed for total lipids, phospholipids or phosphate. Various suitable methods are outlined in Kates (1972). Preferably, the phospholipids must be of sufficient purity such that, when mixed at a total concentration of about 10 mg/mL, the mixture can be sonicated as described below to provide a relatively translucent solution. Preferably, the phospholipids are at least 90% pure, more preferably, they are at least 95% pure and, most preferably, they are at least 99% pure.

C. Potentiating Components

One factor that can influence the therapeutic activity of the compositions of the present invention is the presence of a potentiating component. Under certain conditions LPA alone has displayed mitogenic activity and a short half life in vivo and under certain storage conditions. The present invention provides novel compositions in which one or more potentiating components are combined with LPA that have been found to potentiate the therapeutic activity of LPA. A "potentiating component" is defined as a molecule which potentiates the therapeutic activity of LPA. Potentiating components include, but are not limited to, proteins, other phospholipids, polyethylene glycols (PEG), lipid membrane structure forming compounds, polypeptides, modified polypeptides and polymers.

In some cases, the presence of calcium has been found to inhibit the anti-apoptotic properties of LPA. However, certain potentiating components have proven to counteract the inhibition by calcium. Therefore, in one embodiment, LPA is presented in combination with a potentiating component such as BSA and/or PEG. Alternative potentiating components appropriate to protect the activity of LPA can be identified by performing a screen as described in Example 2, in the presence and absence of the potentiating component to be tested.

An appropriate potentiating component for use in the present invention can easily be selected by combining the composition to be evaluated with a therapeutic amount of LPA in a therapeutically acceptable solution and evaluating the combination for its mitogenic activity, storage stability, in vivo half life, and for anti-apoptotic activity by any method known in the art, including those described herein. If the mixture has acceptable stability, is not therapeutically unacceptable due to mitogenic activity, and displays anti-apoptotic activity, or preserves or restores cell, tissue or organ function, the potentiating component is appropriate for use in the present invention.

1. Other Phospholipids

In one embodiment of the present invention, the phospholipids PA; PI; lysophosphatidic acid; LPI; and LPC are present in the composition in a range of ratios from 0–20:5–20:2–16:0–4:0–8, respectively. Preferably, these phospholipids are in a ratio of approximately 2–15:8–15:6–10:2–4:2–8, respectively. Most preferably, these phospholipids are in a ratio of approximately 10:10:8:2:4, respectively.

2. Polyethylene Glycol

In one embodiment of the present invention, LPA is combined with PEG prior to therapeutic use. PEGs constitute a diverse group of molecules. Only those that potentiate the therapeutic efficacy of LPA are encompassed herein. It is within the skill of one in the art to determine whether a particular PEG is suitable for use in the claimed compositions. Such a determination can be made, for instance, by the methods described herein.

Polyethylene glycol ("PEG"), (α-Hydro-ω-hydroxypoly (oxy-1,2-ethanediyl)), is known by numerous designations including macrogel; PEG; Carbowax; Jeffox; Nycoline; Pluracol E; Poly-G; Polyglycol E; and Solbase. PEG refers to the liquid and solid polymers of the general formula $H(OCH_2—CH_2)_nOH$, where n is greater than or equal to 4. In general, each PEG is followed by a number which corresponds to its average MW. PEG syntheses are described for instance in Hibbert (1939) *J. Am. Chem. Soc.* 61:1905–1910. For review, see also, Powell, III in *Handbook of Water-Soluble Gums & Resins*, R. L. Davidson ed. (McGraw-Hill, New York, 1980) pp. 18/1–18/31. PEGs have found use as water-soluble lubricants for rubber molds, textile fibers, and metal-forming operations, in food and food packaging, in hair preparations and in cosmetics in general and as ointment and suppository bases in pharmaceutical compositions.

Typically, PEGs are clear, viscous liquids or white solids that dissolve in water to form transparent solutions. They are soluble in many organic solvents and readily soluble in aromatic hydrocarbons. They are only slightly soluble in aliphatic hydrocarbons. Typically, they do not hydrolyze on storage. PEGs have low toxicity. The molecular weights of PEG compositions listed herein are given in number averages rather than weight averages.

PEG20M consists of two or more molecules of PEG having approximate molecular weights of 6000–10,000 joined by a bisphenol epoxide linker (CAS # 37225-26-6; CAS name Oxirane, 2,2' [(1-methyl-ethylidene)bis(4,1-phenyleneoxy methylene)]bis-, polymer with α-hydro-ω-hydroxypoly(oxy-1,2-ethanediyl). PEG20L is a substantially linear PEG having an average molecular weight of about 20,000 Daltons (available from several commercial sources including, but not limited to, Clariant/Hoechst Celanese, Fluka and Nippon Oils and Fats). The molecular weights of PEG compositions listed herein are given in number averages rather than weight averages. Various other molecular weights of linear PEG are also available from several commercial sources.

More recently, PEG has been used in a number of pharmacologic applications. The conjugation of PEG to foreign proteins, such as cytokines and antibodies, reduces the immune response triggered when the proteins are administered into test mammals. U.S. Pat. Nos. 5,447,722; 4,902,502; 5,089,261; 5,595,732; 5,559,213; and 4,732,863. Conjugation to PEG also increases the solubility and biological half-life of cytokines. WO 8700056 and U.S. Pat. No. 5,089,261. Conjugates of PEG and glucocerebroside have been formulated for treating Gaucher's disease. WO 9413311. PEG has also been conjugated to such enzymes as adenosine deaminase, amidase bovine and asparaginase, for therapeutic use. See Delgado et al. (1992) *Crit. Rev. Ther. Drug. Carrier Syst.* 9:249–304; and Burnham (1994) *Am. J. Hosp. Pharm.* 51:210–218, for review.

The invention further encompasses compositions comprising therapeutically effective amounts of LPA and PEG. In compositions comprising LPA and PEG, the PEG to LPA weight ratio is such that the LPA therapeutic activity is potentiated by the PEG. Typically, the PEG to LPA weight ratio of the composition is preferably 1–100,000:1 and most preferably 10–10,000:1.

PEG can be in the molecular weight range from about 6,000 to about 500,000. Preferably, the PEG has an average molecular weight of about 8,000 to about 40,000. More preferably, the PEG has an average molecular weight of from about 20,000 to about 40,000. Most preferably, the PEG has an average molecular weight of 20,000. Even more preferably, the PEG is 20L PEG. By "PEG20L" is meant a substantially linear PEG having an average molecular weight of about 1,000 to 100,000 Daltons, preferably about 8,000 to 35,000 Daltons, and most preferably about 20,000 Daltons. Experience in our laboratory suggests that certain samples of PEG 20L may not be suitable for use in the compositions described herein. Therefore, each sample should be tested for activity before use, preferably as described herein. By "linear PEG" or "linear polymer" is meant that each PEG molecule comprises a single polymeric subunit without molecular linkages such as those found in PEG20M. PEG of 35,000 molecular weight is also preferred. PEG of higher molecular weight may have clearance problems when administered in vivo. Thus, PEG of molecular weight greater than 35,000 is preferably used in compositions for topical delivery.

With reference to PEG20L, "linear PEG" or "linear polymer" means that each PEG molecule comprises a single subunit without molecular linkages. By "having an average molecular weight of about 20,000 Daltons" is meant that individual linear polymers can vary in length, but the average molecular weight is about 20,000 Daltons. Those of ordinary skill in the art will appreciate that synthetic polymers such as PEG cannot be prepared practically to have exact molecular weights, and that the term "molecular weight" as used herein refers to the average molecular weight of a number of molecules in any given sample, as commonly used in the art. For example, a sample of PEG 2,000 might contain a statistical mixture of polymer molecules ranging in weight from, for example, 1,500 to 2,500 Daltons with one molecule differing slightly from the next over a range. Specification of a range of molecular weight indicates that the average molecular weight can be any value between the limits specified, and can include molecules outside those limits. The molecular weight distribution of a PEG can be determined by gel permeation chromatography (GPC), a technique known in the art, using, for example, a combination of columns to achieve resolution from 1,000,000 to 200 molecular weight. PEG standards from 100,000 to 1,400 molecular weight can be used for calibration.

PEG20L is supplied as a white flake, and is readily soluble in water. The oxidation rate of PEG is dependent on storage conditions including: (1) temperature; (2) exposure to light; and (3) the availability of oxygen.

By "anoxically" is meant the reduction of ambient oxygen, a condition which can be maintained by purging with argon or nitrogen gas, and then packaging in a gas-impervious container. The absence of oxygen need not be total. Preferably, it is below about 10% of the total gas present in the sample. More preferably, it is below about 1% of total gas present in the sample.

Preferably, PEG is present in an effective concentration and is essentially free of impurities. By "impurities" is meant the products produced when PEG is oxidized. In addition, small molecular fragments are formed such as formate, methyl formate, formaldehyde, acetaldehyde, etc., all of which are defined here as impurities. These impurities can be removed by any method known in the art, including, but not limited to, dialysis, which removes not only small molecular impurities such as formaldehyde, but also removes hydroperoxides, as evidenced by spectrophotometry. In order to determine the effectiveness of dialysis, conductivity is measured. When dialysis is effective, conductivity drops markedly to 10–20 microsiemens.

Removal of impurities by dialysis can be performed through a Cellulose Acetate Hollow Fiber Dialyzer (Baxter Model CA 110) but the same procedure can also be performed by Ultrafiltration using a Regenerated Cellulose Ultrafiltration Membrane or a Polyethersulphone Ultrafiltration Membrane or using other dialysis methods known in the art. The membrane should have a molecular weight cut off of approximately 20,000 Daltons to allow removal of impurities, metals and other contaminants.

By "therapeutically effective amount" is meant an amount sufficient to effect beneficial or desired clinical results. A therapeutically effective amount can be administered in one or more administrations.

Preferably, PEG is present in a therapeutically effective amount. In the case of OPS, an effective amount is the amount required to improve the ability of an OPS to preserve organs.

In the case of compositions comprising LPA and PEG, where the compositions include other phospholipids, the preferred composition is where phospholipids are combined in a ratio of about 10:10:8:2:4 by weight. A ratio of "about" means that the ratios of the phospholipids can range approximately up to 15% but preferably not more than 5%. More preferably, the ratios are within ±0.5%.

Just as PEG has been used as a potentiating component for therapeutic agents, so the capacity of other macromolecules and macromolecular structures to serve as potentiating components has been explored. Included among these are various lipid membrane structures and proteins.

3. Lipid Membrane Structures.

Lipid membrane structures (LMSs), including liposomes, micelles, multilamellar vesicles and cellular membrane isolates, have been used as vehicles for delivering therapeutic agents. U.S. Pat. Nos. 5,045,530; 5,141,751; 5,100,662; 5,292,499; 5,213,804; 5,449,513; 5,190,822; 5,540,925; and 5,395,619. LMSs are lamellar lipid particles wherein polar head groups of a polar lipid are arranged to face an aqueous phase of an interface to form membrane structures.

As used herein, a "liposome" or "lipid vesicle" is a small vesicle bounded by at least one and possibly more than one bilayer lipid membrane. These vesicles are made artificially from phospholipids, glycolipids, lipids, steroids such as cholesterol, related molecules, or a combination thereof by any technique known in the art, including, but not limited to sonication, extrusion, or removal of detergent from lipid-detergent complexes. A liposome can also optionally comprise additional components associated with the outer surface, such as a tissue targeting component. It is understood that a "lipid membrane" or "lipid bilayer" need not consist exclusively of lipids, but can additionally contain any percentage of other components, including, but not limited to, cholesterol and other steroids, proteins of any length, and other amphipathic molecules, providing the general structure of the membrane is a sheet of two hydrophilic surfaces sandwiching a hydrophobic core. For a general discussion of membrane structure, see *The Encyclopedia of Molecular Biology* by J. Kendrew (1994). Suitable lipids include, but are not limited to, those discussed in Lasic (1993) "Liposomes: from Physics to Applications" Elsevier, Amsterdam.

The lipid bilayer making up the liposome can comprise phospholipids, glycolipids, steroids, and their equivalents; amphipathic proteins, and lipid-soluble chemicals. Preferably, a composition is chosen that allows the membrane to be formed with reproducible qualities, such as diameter, and is stable in the presence of elements expected to occur where the liposome is to be used, such as physiological buffers and circulating molecules. Preferably, the liposome is resilient to effects of manipulation by storage, freezing, and mixing with pharmaceutical excipients.

Lipids suitable for incorporation into lipid membrane structures include, but are not limited to, natural, semi-synthetic or synthetic mono- or di-glycerophospholipids including phosphatidylcholines, phosphatidylethanolamines, phosphatidylglycerols, phosphatidylinositols, phosphatidic acids, phosphatidylserines, glycero- and cardiolipins. Sphingolipids such as sphingomyelin and cerebrosides can also be incorporated. While natural phospholipids occur with the phospho moiety at the sn-3 position and hydrophobic chains at the sn-1 and sn-2 positions, synthetic lipids can have alternative stereochemistry with, e.g., the phospho group at the sn-1 or sn-2 positions. Furthermore, the hydrophobic chains can be attached to the glycerol backbone by acyl, ether, alkyl or other linkages. Derivatives of these lipids are also suitable for incorporation into liposomes. Derivatives suitable for use include, but are not limited to, haloalkyl derivatives, including those in which all or some of the hydrogen atoms of the alkyl chains are substituted with, e.g., fluorine. In addition, cholesterol and other amphipathic steroids, bolaamphiphiles (lipids with polar moieties at either end of the molecule which form monolayer membranes) and polyglycerolmonoalkylthers can also be incorporated. Liposomes can be composed of a single lipid or mixtures of two or more different lipids.

In one preferred embodiment, the lipid bilayer of the liposome is formed primarily from phospholipids. More preferably, the phospholipid composition is a complex mixture, comprising a combination of phosphatidylcholine (PC), phosphatidic acid (PA), phosphatidylethanolamine (PE), phosphatidylglycerol (PG) and sphingomyelin (SM). The LMS can further comprise additional lipids such as phosphatidylinositol (PI), phosphatidylserine (PS), or cardiolipin (diphosphatidylglycerol). If desired, SM can be replaced with a greater proportion of PC, PE, or a combination thereof. PS can optionally be replaced with phosphatidylglycerol (PG). Preferably, at least PC and PE are included; more preferably, at least three of the group PC, PS, PE, and SM are included. The composition is chosen so as to confer upon the LMS stability during both storage and administration.

Practitioners of ordinary skill will readily appreciate that each phospholipid in the foregoing list can vary in its structure depending on the fatty acid moieties that are esterified to the glycerol moiety of the phospholipid. Generally, most commercially available forms of a particular phospholipid can be used. However, phospholipids containing particular fatty acid moieties may be preferred for certain applications.

Preferably, the LMS also includes cholesterol or a related steroid to improve the rigidity of the membrane. Any amount of cholesterol can be used. A preferred ratio of total cholesterol to lipid is between about 0.5 and about 1.2 moles of cholesterol per mole of lipid. More preferred is a molar ratio of about 0.8 to about 1.2:1; even more preferred is a molar ratio of about 0.9 to about 1.1:1; still more preferred is a molar ratio of about 1.0:1.0. Other molecules that can be used to increase the rigidity of the membrane include cross-linked phospholipids.

Other preferred liposomes for use in vivo are those with an enhanced ability to evade the reticuloendothelial system, thereby giving them a longer period in which to reach the target cell. Effective lipid compositions in this regard are those with a large proportion of SM and cholesterol, or SM and PI. Liposomes with prolonged circulation time also include those that comprise the monosialoganglioside GM1, glucuronide, or PEG. For example, cholesterol can be added at the ratios indicated above to a lipid mixture consisting of any combination of SM, PI, glucuronide, PEG, and other suitable components.

Liposomes are completely closed lipid bilayer membranes which contain entrapped aqueous volume. Liposomes are vesicles which can be unilamellar (single membrane) or multilamellar (onion-like structures characterized by multiple membrane bilayers, each separated from the next by an aqueous layer). The bilayer is composed of two lipid monolayers having a hydrophobic "tail" region and a hydrophilic "head" region. In the membrane bilayer, the hydrophobic (nonpolar) "tails" of the lipid monolayers orient toward the center of the bilayer, whereas the hydrophilic (polar) "heads" orient toward the aqueous phase. The basic structure of liposomes can be made by a variety of techniques known in the art.

Methods of making LMSs are well known in the art. A number of publications describe a variety of methods for preparing liposomes of different structure and lipid composition. Gregoriadis (1988) *Liposomes as Drug Carriers* Wiley, New York; Gregoriadis (1993) *Liposome Technology 2nd Ed. Vol. I: Liposome Preparation and Related Techniques* CRC Press, Boca Raton; Watwe et al. (1995) *Curr. Sci.* 68:715–724; Vemuri et al. (1995) *Pharm. Acta Helvetiae* 70:95–111; Elorza et al. (1993) *J. Microencapsulation* 10:237–248; and U.S. Pat. Nos. 4,737,323 and 5,008,050.

Liposomes can also be provided with molecules at the surface that target them to the cell of interest. Such small molecules can be attached by incorporating into the lipid bilayer a functionalized phospholipid (U.S. Pat. Nos. 5,052,421 and 5,540,935) or a functionalized cholesterol (U.S. Pat. No. 4,544,545). Polypeptides can be attached covalently to the lipid bilayer (EP Patent 0036277), to a glycophospholipid (U.S. Pat. No. 5,374,548), to a carboxylated phospholipid (U.S. Pat. No. 4,762,915), to a derivatized sterol (U.S. Pat. No. 5,000,960), or to a peptide anchor (U.S. Pat. No. 5,109,113). Alternatively, if the polypeptide comprises a hydrophobic domain, it can be incorporated directly into the lipid bilayer, either by forming the liposome in its presence, or by performing the liposome and inserting the polypeptide subsequently using a suitable detergent. Tranum-Jensen et al. (1994) *J. Membrane Biol.* 140: 215–23; EP Patent 0047480; and U.S. Pat. No. 5,252,348.

Liposomes have been prepared with mammalian-derived peptides such as cytokines (U.S. Pat. No. 5,258,499), transferrin (Stavridis et al.), antibody (Laukkanen et al. (1994) *Biochem.* 33:11664–11670), asialofetuin and other galactose-terminated side chains (Ishihara (1990) *Pharm. Res.* 7:542–546; and Ghosh et al. (1991) In: *Liver Diseases, Targeted Diagnosis and Therapy Using Specific Receptors and Ligands* Wu et al., Ed. Marcel Dekker, New York), a fusogenic protein from rat brain microsomal membranes (Rakowska et al. (1994) *J. Membrane Biol.* 142:35–42), and surfactant protein A (Walther et al. (1993) *Am. J. Physiol.* 265:L330–339). Liposomes have been prepared with artificial peptides, such as a 14-residue amphipathic sequence which is a fusogenic GALA-type peptide. Puyal et al. (1994) *Biochim. Biophys. Acta* 1195:259–266. Liposomes have also been prepared with viral components: for example, the F and G glycoprotein of respiratory syncytial virus (RSV) (U.S. Pat. No. 5,252,348), reovirus M cell attachment protein (Rubas et al. (1990) *J. Microencapsulation* 7:385–395), influenza virus surface protein (WO 92/19267; EP 0047480; and Nussbaum et al. (19897) *J. Virol.* 61:2245–2252), viral membrane fusion proteins, particularly hemagglutinin (WO 95/32706), and the influenza hemagglutinin D loop and K loop peptides (Friede et al. (1994) *Vaccine* 12:791–797).

Rapid uptake of liposomes in vivo by cells of the reticuloendothelial system has restricted their therapeutic utility. This problem has been overcome by incorporation of lipids derivatized with various synthetic polymers, for example, polyethylene glycol (PEG), polylactic acid, polyglycolic acid, or combinations thereof. Woodle and Lasic (1992) *Biochim. Biophys. Acta* 1113:171–199; Zalipsky et al. (1994) *FEBS Letters* 353:71–74; and U.S. Pat. No. 5,395,619.

The present invention encompasses compositions and methods of using compositions comprising micelles. Micelles in aqueous solution, both non-ionic, cationic and anionic, have been described in the literature in numerous publications. Mittal (1977) *Micellization, Solubilization and Microemulsions* Plenum Press, New York; Mittal (1979) *Solution Chemistry of Surfactants* Plenum Press, New York; Menger (1977) *In Biorganic Chemistry III. Macro-and Multicomponent Systems* Van Tanelen, Ed. Academic Press, New York; and Menger (1979) *Acc. Chem. Res.* 12:111–117. "Micelles" is a term applied to aggregates which form from tenside molecules in aqueous solutions above a specific temperature or a characteristic concentration. This concentration is called the critical micellization concentration, or cmc. When the cmc is exceeded, the monomer concentration remains practically constant and the excess tenside molecules form micelles. They can occur in various shapes (spheres, rods, discs) depending on the chemical constitution of the tenside and on the temperature, concentration or ionic strength of the solution. The micelles have characteristic aggregation numbers with usually only a small distribution spread. Reaching the cmc is manifest by abrupt changes in the surface tension, the osmotic pressure, the electrical conductivity and the viscosity. Micelles are thermodynamically stable association colloids of surfactant substances in which the hydrophobic radicals of the monomers lie in the interior of the aggregates and are held together by hydrophobic interaction; the hydrophilic groups face the water and by solvation provide the solubility of the colloid.

A process for preparing liposomes containing LPA is as follows. An aqueous dispersion of liposomes is prepared from membrane components, such as phospholipids (e.g. phosphatidylcholine, phosphatidylglycerol, sphingomyelin and phosphatidylethanolamine) and glycolipids according to known methods as disclosed. *Ann. Rev. Biophys. Bioeng.* 9:467 (1980). The liposomes can further contain sterols (e.g., cholesterol and cholestanol), dialkylphosphates, dicylphosphatidic acids, stearylamine, $\alpha$-tocopherol, etc., in the liposomal membrane.

To the liposomal dispersion thus prepared is added an aqueous solution of LPA, at a concentration sufficient to produce a therapeutically effective final product, and the mixture is allowed to stand for a given period of time, preferably under warming at a temperature more than the phase transition temperature of the membrane or above 40° C., followed by cooling to thereby prepare liposomes containing LPA in the liposomal membrane.

Alternatively, the desired liposomes can also be prepared by previously mixing the above-described membrane components and LPA and treating the mixture in accordance with known methods for preparing liposomes.

The lipid vesicles can be prepared by any suitable technique known in the art. Methods include, but are not limited to: microencapsulation, microfluidization, LLC method, ethanol injection, freon injection, the "bubble" method, detergent dialysis, hydration, sonication, and reverse-phase evaporation (reviewed in Watwe et al.). For example, ultrasonication and dialysis methods generally produce small unilamellar vesicles; extrusion and reverse-phase evaporation generally produce larger sized vesicles. Techniques can be combined in order to provide vesicles with the most desirable attributes. One particularly preferred method is microfluidization.

The invention encompasses LMSs containing tissue or cellular targeting components. Such targeting components are components of a LMS, that enhance its accumulation at certain tissue or cellular sites in preference to other tissue or cellular sites when administered to an intact animal, organ, or cell culture. A targeting component is generally accessible from outside the liposome, and is therefore generally either bound to the outer surface or inserted into the outer lipid bilayer. A targeting component can be inter alia a peptide, a region of a larger peptide, an antibody or antigen binding fragment thereof, a nucleic acid, a carbohydrate, a region of a complex carbohydrate, a special lipid, or a small molecule such as a drug, hormone, or hapten, attached to any of the aforementioned molecules.

Via targeting components, the LMSs can be targeted to any cell type toward which a therapeutic treatment is to be directed, e.g., a cell type which is undergoing an inappropriate level of apoptosis. Such cells include, but are not limited to, cardiomyocytes, endothelial cells, neuronal cells, hepatocytes, glomerulocytes, lung cells, mucosal cells, skin cells and heart cells.

LMSs can be targeted to such cell types in various ways. For example, a LMS can be modified to contain an antibody, or a fragment of an antibody, specific for a cell surface molecule, or marker, found solely or primarily on a given cell type. Antibodies with specificity toward cell type-specific cell surface markers are known in the art.

The compositions of the present invention can additionally comprise surfactants. Surfactants can be cationic, anionic, amphiphilic, or nonionic. A preferred class of surfactants are nonionic surfactants; particularly preferred are those that are water soluble. Nonionic, water soluble surfactants include polyoxyethylene derivatives of fatty alcohols, fatty acid ester of fatty alcohols and glyceryl esters, wherein the polyoxyethylene group is coupled via an ether linkage to an alcohol group. Examples include, but are not limited to, polyoxyethylene sorbitan fatty acid esters, polyoxyethylene castor oil derivatives, polyoxyethylene hardened castor oil derivatives, fatty acid sodium salts, sodium cholates, polyexyethylene fatty acid ester and polyoxyethylene alkyl ethers.

4. Proteins

Proteins other than serum albumin have been characterized or implicated as having fatty acid/lipid binding capabilities. These include the fatty acid binding proteins (FABPs); the lipid binding proteins; long-chain fatty acyl-CoA (LCFA-CoA) binding proteins; phospholipid transfer proteins; and $Ca^{2+}$/lipid binding proteins. Lipid-binding proteins are a family of fatty acid and retinoid transport proteins. Some are intracellular, while others are secreted from the cell. Intracellular lipid binding proteins include cellular retinoic acid binding proteins, CRABP I and CRABP II, which belong to a family of small cytosolic lipid binding proteins and appear to play a role in regulating transport and metabolism of retinoic acid in the developing embryo and throughout adult life. Banaszak et al. (1994) *Adv. Prot. Chem.* 45:89–151; and Donovan et al. (1995) *J. Steroid Biochem. Mol. Biol.* 53:459–465. The lipid-binding protein family includes many FABP. The FABP are relatively small proteins (13–15 kDa) capable of binding long-chain fatty acids (LCFA) and their coenzyme A and L-carnitine esters. They are believed to have major functions in the metabolism of LCFA for energy production or storage, and are abundantly present in tissues such as the intestine, liver and heart, which are actively involved in the uptake or utilization of LCFA. Bass (1993) *Mol. Cell. Biochem.* 123:191–202; and Glatz and van der Vusse (1989) *Mol. Cell. Biochem.* 88:37–44. A liver form of FABP has been shown to stimulate export of LPA from mitochondria. Vancura and Haldar (1992) *J. Biol. Chem.* 267:14353–14359.

LCFA-CoA play an important physiological role in intermediary metabolism of fatty acids, but recent data indicate that they also can be potent regulators of cell functions. LCFA-CoA typically exist within a cell bound to membrane lipids and/or proteins. Proteins which bind LCFA-CoA include LCFA CoA binding protein, FABP and sterol carrier protein-2. Gossett et al. (1996) *Lipids* 31:895–918.

A protein that enhances a therapeutic effect of LPA can be a naturally-occurring or a synthetic protein, a protein fragment, or can contain lipid or sugar moieties. Preferably, the protein is a lipid-binding or carrier protein. The protein can contain other modifications including, but not limited to glycosylation, phosphorylation, myristylation, sulfation and hydroxylation. The protein can be a hybrid protein, part of which confers the property of enhancing a therapeutic effect of LPA, and another part of which confers some other desirable property such as targeting to a particular cell type, enhanced in vivo stability, and the like. Preferred proteins include, but are not limited to, albumin, soy and plant proteins, cytochrome C, low density lipoprotein, acyl carrier protein and alphafeto-protein.

Suitable polypeptides include any known in the art and include, but are not limited to, fatty acid binding proteins. Modified polypeptides contain any of a variety of modifications, including, but not limited to glycosylation, phosphorylation, myristylation, sulfation and hydroxylation. As used herein, a suitable polypeptide is one that will protect LPA to preserve its activity. Examples of binding proteins include, but are not limited to, albumins such as bovine serum albumin (BSA) and pea albumin.

Proteins active in enhancing anti-apoptotic activity of LPA bind to LPA. "Binding" as used herein means that the LPA and the protein form non-covalent complexes with one another. Binding of a protein to LPA can be determined by a variety of methods known in the art, including a non-denaturing gel electrophoresis binding assay as described in Example 3 or a size shift assay as described in Example 3.

The protein/LPA compositions optionally exhibit a reduction in the mitogenic activity of LPA. Mitogenic activity can be measured by any method known in the art, for instance, measurement of uptake of $^3$H-thymidine by cells treated with LPA with or without the addition of protein.

LPA/protein compositions of the present invention can be prepared in a variety of ways. LPA and a protein can be suspended in any biocompatible buffer, for example, bicarbonate buffered saline, at a ratio of about 0.00001% to 10%, more preferably about 0.001% to 1%. The mixtures can then be sonicated for about 5 minutes or until the mixture is clear or can be sterile filtered.

The protein concentration of the LPA/protein compositions can be from about 0.001 to about 50 mg/mL, more preferably from about 0.01 to about 10 mg/mL, even more preferably from about 0.05 to about 1.0 mg/mL.

The protein component of the LPA/protein compositions of the present invention are substantially pure, i.e., the protein is substantially free of lipids, other proteins, or any other material that might affect the activity of the LPA/protein complex. Preferably, the protein is at least about 75% pure, more preferably at least about 85% pure and still more preferably at least about 95% pure.

5. Other Optional Components

Suitable polymers can be any known in the art of pharmaceuticals and include, but are not limited to, naturally-occurring polymers such as dextrans, hydroxyethyl starch, and polysaccharides; and synthetic polymers.

Examples of naturally occurring polymers include proteins, glycopeptides, polysaccharides, dextran and lipids. The additional polymer can be a synthetic polymer. Examples of synthetic polymers which are suitable for use in the present invention include, but are not limited to, polyalkyl glycols (PAG) such as PEG, polyoxyethylated polyols (POP) such as polyoxyethylated glycerol (POG), polytrimethylene glycol (PTG) polypropylene glycol (PPG), polyhydroxyethyl methacrylate, polyvinyl alcohol (PVA), polyacrylic acid, polyethyloxazoline, polyacrylamide, polyvinylpyrrolidone (PVP), polyamino acids, polyurethane and polyphosphazene. The synthetic polymers can also be linear or branched, substituted or unsubstituted, homopolymeric, co-polymers, or block co-polymers of two or more different synthetic monomers.

The synthetic polymers can have the following generic structure:

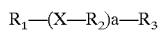

where $R_1$ and $R_3$ are the same or different and are H, $H_3C$, OH, $R_2$ or a reactive group (as described below); where $R_2$ is a linear or branched substituted or unsubstituted alkyl group; where X is O (in which case the synthetic polymer can be a polyoxyalkylene) or X is NH(C=O) (in which case the synthetic polymer can be a polyamine), or X is absent (in which case the synthetic polymer can be a polyalkylene); and a is an integer between 1 and about 1,000.

Biodegradable polymers can also be included in the compositions. These include, but are not limited to poly (lactide), poly(glycolide) poly(vinyl alcohol), crosslinked collagen. The polymers can also include polyglycolic acid, polyethylene terephthalate, polybutyl lactose, polycaprolactone, D-polylactic acid, L-polylactic acid and poly-L-lysine and polymeric mixtures thereof.

Suitable polymers also include polysaccharides. Suitable polysaccharides include, but are not limited to, trehalose, glucose, maltose, lactose, maltulose, iso-maltulose, lactulose, mono-reducing glycosides of polyhydroxy compounds selected from sugar alcohols, other straight chain polyalcohols, raffinose, stachyose, melezitose, dextran, sucrose and sugar alcohols thereof, maltitol, lactitol, iso-maltulose, palatinit, 2-D-glucopyranosyl-1-β-6-mannitol and their individual sugar alcohols.

The compositions can further include pharmaceutically acceptable excipients. Pharmaceutically acceptable excipients include, but are not limited to, topical pharmaceutically acceptable carrier, cosmetic carrier, sterile solutions, sterile isotonic solutions, ingestable liquids, pharmaceutically acceptable aerosols and solutions for organ/tissue/cell preservation and/or transplantation.

The compositions can further include additional pharmaceutically effective agents. Suitable classes of pharmaceutically effective agents include, but are not limited to, drugs, antibiotics, wound healing agents and antioxidants.

Suitable drugs include, but are not limited to, those from the following classes. Other examples are presented in Table 1. Antipyretic and anti-inflammatory drugs, analgesics, antiarthritics, antispasmodics, antidepressants, antipsychotics, tranquilizers, antianxiety drugs, narcotic antagonists, antiparkinsonism agents, cholinergic antagonists, chemotherapeutic agents, immuno-suppressive agents, antiviral agents, parasiticides, appetite suppressants, antiemetics, antihistamines, antimigraine agents, coronary vasodilators, cerebral vasodilators, peripheral vasodilators, hormonal agents, contraceptives, antithrombotic agents, diuretics, antihypertensive agents, cardiovascular drugs, opioids, and vitamins are all included in the compositions described herein.

TABLE 1

| Cardiac glycosides | Immunotherapies | Antifungal |
|---|---|---|
| digitalis | interferon | amphotericin B |
| digitoxin | interleukin-2 | myconazole |
| lanatoside C | monoclonal antibodies | muramyl dipeptide |
| digoxin | gammaglobulin | clotrimazole |
| Anticancer | Steroids | Antiarrhythimic |
| azathioprine | prednisone | propanolol |
| bleomycin | triamcinolone | etanolol |
| byclophosphamide | hydrocortisone | verapamil |
| adriamycin | dexamethasone | captopril |
| daunorubicin | betamethosone | isosorbide |
| vincristine | prednisolone | |
| Antibiotic | Hormones | Antiviral |
| penicillin | antidiuretic | acyclovir and derivatives |
| tetracycline | corticosteroids | Winthrop-51711 |
| erythromycin | testosterone | ribavirin |
| cephalothin | estrogen | rimantadine/amantadine |
| imipenem | thyroid | azidothymidine & |
| cefofaxime | growth | derivatives |
| carbenicillin | ACTH | adenine arabinoside |
| vancomycin | progesterone | amidine-type protease |
| gentamycin | gonadotropin | inhibitors |
| tobramycin | mineralocorticoid | |
| piperacillin | | Vaccines |
| moxalactam | Antihistanmines | influenza |
| amoxicillin | pyribenzamine | respiratory syncytial virus |
| ampicillin | chlorpheniramine | Hemophilus influenza |
| cefazolin | diphenhydramine | vaccine |
| cefadroxil | | |
| cefoxitin | Antiparasitic | Antihypotension |
| other | praziquantel | dopamine |
| aminoglycosides | metronidazole | dextroamphetamine |
| other cephalosporins | pentamidine | |
| Antiasthma | Sedatives & Analgesic | Tranquilizers |
| metaproterenol | morphine | chlorpromazine |
| aminophylline | dilaudid | benzodiazepine |
| theophylline | codeine | butyrophenomes |
| terbutaline | codeine-like synthetics | hydroxyzines |
| Tegretol | Demerol | meprobamate |
| ephedrine | oxymorphone | phenothiazines |
| isoproterenol | Phenobarbital | reserpine |
| adrenaline | barbiturates | thioxanthines |
| norepinephrine | | |
| Antihypertensives | Antidiabetic | Other |
| apresoline | Diabenese | Receptor agonists and |
| etanolol | insulin | antagonists |

Suitable antibiotics include, but are not limited to, ampicillin, tetracycline, chloramphenicol, erythromycin, amphotericin B and penicillin. Suitable wound healing agents include, but are not limited to, transforming growth factors, platelet-derived growth factors, epidermal growth factors and fibroblast growth factors. Suitable antioxidants include, but are not limited to, naturally-occurring antioxidants such as tocopherols, (e.g., α-tocopherol, vitamin E), ascorbic acid (Vitamin C), β-carotene (vitamin A), dihydrolipoamide and flavenoids; and synthetic antioxidants such as butylated hydroxytoluene, butylated hydroxyanisole, Trolox®, propyl gallate, other phenolic antioxidants and phenothiazines; and chelators such as desferoxamide, HBED and CP130.

II. Methods of Formulating Compositions for Use in The Present Invention

The invention further includes methods of formulating compositions for use in the present invention, some of which appear below and some of which appear throughout the text of the specification.

The compositions of the present invention can be in either a liquid or solid form. In the liquid form, the LPA can be concentrated for dilution prior to use. Preferably, the components are in a concentration suitable for immediate use. In the case of a solid, addition of a predetermined amount of an aqueous solution will result in the appropriate concentration of the components. The solid can also be in powder form, for use in therapies including, but not limited to inhalation therapies. In the case where the composition is a solution, the LPA is preferably present in an amount of from about 0.00001% to about 10% (weight/volume). More preferably, the LPA is present in an amount of from about 0.0001% to about 1% (weight/volume). Most preferably, the LPA is present in an amount of from about 0.005% to about 1% (weight/volume).

Where the composition is a solid, preferably the LPA is present in an amount of from about 0.00001% to 50% (weight/weight). More preferably, the LPA is present in an amount of from about 0.001% to 1% (weight/weight).

LPA can be suspended in any buffered solution that is preferably free of divalent cations having a pH range of 2–10, more preferably, about 4–8 and most preferably about 6–8. Suitable buffers include, but are not limited to, D-PBS (phosphate buffered saline, free of calcium and magnesium salts; Gibco BRL) or 50 mM ammonium bicarbonate containing isotonic sodium chloride. When the compositions are to be used therapeutically, the buffered solution is preferably physiologically acceptable. A wide range of pH values are effective. Preferably the pH is between about 5.5 to about 8. However, any pH at which the composition is at least minimally therapeutically effective is suitable for use. The mixture has been found to be most active at pH 8. Preferably, the phospholipids are suspended in 50 mM ammonium bicarbonate/0.154 M sodium chloride, 250 $\mu$M EDTA with a pH of 7.7–8.0.

Preferably, if there is a mixture of phospholipids/lipids, the mixture is dispersed in order to achieve maximal activity. Any method of dispersion that forms particles of about 5–450 microns is acceptable and about 30–100 microns is preferred. These methods include, but are not limited to, microfluidization, extrusion and sonication, provided that the method does not denature or otherwise chemically modify the phospholipids in such a manner as to render them toxic or of substantially diminished therapeutic activity. Typically, when small batches are prepared, the mixture is sonicated until optical clarity is attained although sonication can be continued beyond this point provided the mixture is not overheated. The preferred sonication parameters are those provided in the examples herein. As used herein, "optical clarity" indicates that the mixture changes from opaque to translucent. This change is readily monitored visually; no further measurements are necessary. However, "translucent" can be defined as when the mixture has an O.D. 600 of less than about 0.2 AU.

Concentrations of up to approximately 50 mg/mL phospholipids can be prepared. Preferably, 10 mg/mL solutions are used. Typically, sonication, if used, is in 5 minute alternating cycles, with 5 minutes of sonication followed by 5 minutes of equilibration. However, this can be varied, depending on the volume of mixture being sonicated and the heat generated by sonication.

The total length of sonication depends on the concentration and volume of the mixture being sonicated and the power output of the sonicator. Sonication should proceed until the mixture has become translucent. Typically, mixtures are sonicated for 3 to 90 minutes. Preferably, sonication proceeds by several periods of 5 minutes each, 6 to 12 total periods, with 1 to 5 minutes between each period to allow equilibration and dissipation of heat. The temperature of the water bath should not exceed about 60° C. Preferably, the temperature of the water bath is not allowed to exceed 37° C. Preferably, the sonicated mixture is passed through a sterile filter before use. Preferably, the sterile filter has a 0.2 micron cut off.

The compositions can be sterilized at any point. Sterilization can be by any method known in the art, and encompasses, but is not limited to, heat sterilization, steam sterilization, ultrafiltration, sterile filtration and ultraviolet light sterilization. Sterilization is essential for most of the methods of treatment, although for certain applications, it may not be necessary, or the level of sterilization required can be reduced. The compositions can also be prepared and dried to form a solid. The solid is suitable for use as a powder or pill, or in solution upon reconstitution. Any method of drying is suitable for use herein, including, but not limited to, freeze-drying, air drying, spray drying and fluidized bed evaporation, vacuum drying and rotary evaporation Preferably, the compositions, both liquid and solid, are stored under anoxic conditions. Any method of such storage known in the art is suitable for use herein, including, but not limited to, storage under an inert gas such as argon.

III. Prevention of Apoptosis and Preservation or Restoration of Cell, Tissue and Organ Function.

The anti-apoptotic activity of the compositions of the present invention can be measured in many anti-apoptosis assays known in the art. These include, but are not limited to, the serum deprivation of the C3H/10T½ cell assay described in detail in Example 2. Furthermore, in vivo apoptosis inhibition can be measured by any method known in the art. Methods for determining therapeutic efficacy in treating an ischemic event are known in the art and described herein. Methods for determining efficacy in organ storage and transplantation are known in the art and described herein.

The therapeutic activity of the compositions described herein can be measured or determined by any method known in the art. For instance, there are a variety of wound healing assays described in the art and cited herein.

The invention further comprises any of the above-described compositions in combination with a pharmaceutically acceptable vehicle. The level of purity of the components necessary for the composition can be determined empirically and is within the skill of one in the art. The compositions are suitable for use in a variety of disorders, as described below, and in both human and veterinary applications.

In general, the compositions are pharmaceutically acceptable due to their low toxicity in the therapeutic dosage range, stability and ability to be incorporated into a wide variety of vehicles for numerous routes of administration. The compositions can be administered alone or in combination with other pharmaceutically effective agents including, but not limited to, antibiotics, wound healing agents, antioxidants and other therapeutic agents. Suitable antibiotics include, but are not limited to, ampicillin, tetracycline, chloramphenicol, erythromycin, amphotericin B and penicillin. Suitable wound healing agents include, but are not limited to, transforming growth factors (TGFs), epidermal growth factors (EGFs), fibroblast growth factors (FGFs) and platelet-derived growth factors (PDGFs). Suitable antioxidants include, but are not limited to, naturally-occurring antioxidants such as tocopherols, (e.g., $\alpha$-tocopherol, vitamin E), ascorbic acid (Vitamin C), $\beta$-carotene (vitamin A), dihydrolipoamide and flavenoids; and synthetic antioxidants such as butylated hydroxytoluene, butylated hydroxyanisole, Trolox®, propyl gall ate, other phenolic antioxidants and phenothiazines; and chelators such as desferrioxamide, HBED and CP130.

The compositions can contain at least a therapeutically effective amount of at least one of the above-described compositions and at least one physiologically acceptable carrier. A physiologically acceptable carrier is one that does not cause an adverse physical reaction upon administration and one in which the compositions are sufficiently soluble to deliver a therapeutically effective amount of the compound. The therapeutically effective amount of the compositions depends in part upon the manner of introduction and the indication to be treated and other criteria evident to one of ordinary skill in the art. Typically, a therapeutically effective amount is one sufficient to ameliorate or cure the condition being treated as evidenced by diminishment of the symptoms compared to a control. Typically, a therapeutically effective amount is from about 0.0001% or 1 $\mu$g/mL by weight of the phospholipid mixture although a wide range of effective amounts can be used for different indications and can be determined empirically. The route(s) of administration useful in a particular indication are discussed below and are well known to one of skill in the art.

IV. Biological Materials Suitable for Treatment and Routes of Administration to These Materials Suitable cell types for treatment and/or preservation include, but are not limited to, eukariotic and prokariotic cells, such as bacterial cells, plant cells, yeast cells, fungi cells, insect cells, mammalian cells, and human cells in particular. Mammalian cell types encompass cardiomyocytes, endothelial cells, neuronal cells, hepatocytes, renal cells, lung cells, mucosal cells, pancreatic cells, gastrointestinal cells, corneal cells and skin cells. These cell types, and the tissues and organs they form, are suitable for treatment and/or preservation by the methods of the present invention. These cell types can be treated either in vivo or in vitro using methods of the present invention.

Routes of administration include, but are not limited to, topical, transdermal, parenteral, gastrointestinal, transbronchial, transalveolar, and in vitro treatment of cells, tissues or organs followed by in vitro administration of treated cells, tissues or organs. Internal routes of administration encompass any method of in vivo administration other than solely by topical application to the skin. Surface administration is accomplished via application of a cream, gel, rinse, etc. containing a therapeutically effective amount of the compositions. Transdermal administration is accomplished by application of a cream, rinse, gel, etc. capable of allowing the active components to penetrate the skin and enter the blood stream. Parenteral routes of administration include, but are not limited to, direct injection such as intravenous, intramuscular, intraperitoneal or subcutaneous injection. Gastrointestinal routes of administration include, but are not limited to, ingestion and rectal. Transbronchial and transalveolar routes of administration include, but are not limited to, inhalation, either via the mouth or intranasally (for example, of a mist or a dry powder) and direct injection into an airway, such as through a tracheotomy.

While the compositions can be topically administered alone, it may be desirable to administer them in a mixture with a topical physiologically or cosmetically acceptable carrier. "Topical pharmaceutically acceptable carrier" as used herein is any substantially non-toxic carrier conventionally useable for topical administration of pharmaceutical agents in which the compositions will remain stable and bioavailable when applied directly to skin or mucosal surfaces. For example, the compositions can be dissolved in a liquid, dispersed or emulsified in a medium in a conventional manner to form a liquid preparation or mixed with a semi-solid (gel) or solid carrier to form a paste, powder, ointment, cream, lotion or the like.

Suitable topical pharmaceutically acceptable carriers include water, petroleum jelly (Vaseline), petrolatum, mineral oil, vegetable oil, animal oil, organic and inorganic waxes, such as microcrystalline, paraffin and ozocerite wax, natural polymers, such as xanthanes, gelatin, cellulose, collagen, starch, or gum arabic, synthetic polymers, such as discussed below, alcohols, polyols, and the like. The carrier can be a water miscible carrier composition that is substantially miscible in water. Such water miscible topical pharmaceutically acceptable carrier composition can include those made with one or more appropriate ingredients set forth above but can also include sustained or delayed release carriers, including water containing, water dispersible or water soluble compositions, such as liposomes, microsponges, microspheres or microcapsules, aqueous base ointments, water-in-oil or oil-in-water emulsions, gels or the like.

In one embodiment of the invention, the topical pharmaceutically acceptable carrier comprises a sustained release or delayed release carrier. The carrier is any material capable of sustained or delayed release of the compositions to provide a more efficient administration resulting in one or more of less frequent and/or decreased dosage of the compositions, ease of handling, and extended or delayed effects on dermatologic conditions. The carrier is capable of releasing the compositions when exposed to any oily, fatty, waxy, or moist environment on the area being treated or by diffusing or by release dependent on the degree of loading of the compositions to the carrier in order to obtain release thereof. Non-limiting examples of such carriers include liposomes, microsponges, microspheres, or microcapsules of natural and synthetic polymers and the like.

Examples of suitable carriers for sustained or delayed release in a moist environment include gelatin, gum arabic, xanthane polymers; by degree of loading include lignin polymers and the like; by oily, fatty or waxy environment include thermoplastic or flexible thermoset resin or elastomer including thermoplastic resins such as polyvinyl halides, polyvinyl esters, polyvinylidene halides and halogenated polyolefins, elastomers such as brasiliensis, polydienes, and halogenated natural and synthetic rubbers, and flexible thermoset resins such as polyurethanes, epoxy resins and the like. Preferably, the sustained or delayed release carrier is a liposome, microsponge, microsphere or gel.

The compositions used in the method of treating dermatologic conditions of the invention are applied directly to the areas to be treated. While not required, it is desirable that the topical composition maintain the active components at the desired location for about 24 to 48 hours, or a length of time sufficient to exert therapeutic efficacy.

If desired, one or more additional ingredients conventionally found in topical pharmaceutical or cosmetic compositions can be included with the carrier, such as a moisturizers, humectants, odor modifiers, buffers, pigments, preservatives, Vitamins such as A, C and E, emulsifiers, dispersing agents, wetting agents, odor-modifying agents, gelling agents, stabilizers, propellants, antimicrobial agents, sunscreens, enzymes and the like. Those of skill in the art of topical pharmaceutical formulations can readily select the appropriate specific additional ingredients and amounts thereof. Suitable non-limiting examples of additional ingredients include superoxide dismutase, stearyl alcohol, isopropyl myristate, sorbitan monooleate, polyoxyethylene stearate, propylene glycol, water, alkali or alkaline earth lauryl sulfate, methylparaben, octyl dimethyl-p-amino benzoic acid (Padimate O), uric acid, reticulin, polymucosaccharides, hydroxyethyl starch (such as, DuPont Pentafraction), hyaluronic acids, aloe vera, lecithin, polyoxyethylene sorbitan monooleate, Vitamin A or C, tocopherol (Vitamin E), alpha-hydroxy of alpha-keto acids such as pyruvic, lactic or glycolic acids, or any of the topical ingredients disclosed in U.S. Pat. Nos. 4,340,586, 4,695,590, 4,959,353 or 5,130,298 and 5,140,043.

Because dermatologic conditions to be treated may be visible, the topical carrier can also be a topical cosmetically acceptable carrier. By "topical cosmetically acceptable carrier" as used herein is meant any substantially non-toxic carrier conventionally useable for topical administration of cosmetics in which the compositions will remain stable and bioavailable when applied directly to the skin surface. Suitable cosmetically acceptable carriers are known to those of skill in the art and include, but are not limited to, cosmetically acceptable liquids, creams, oils, lotions, ointments, gels, or solids, such as conventional cosmetic night creams, foundation creams, suntan lotions, sunscreens, hand lotions, make-up and make-up bases, masks and the like. Thus, to a substantial extent, topical cosmetically acceptable carriers and pharmaceutically acceptable carriers are similar, if not often identical, in nature so that most of the earlier discussion on pharmaceutically acceptable carriers also applies to cosmetically acceptable carriers. The compositions can contain other ingredients conventional in cosmetics including perfumes, estrogen, Vitamins A, C or E, alpha-hydroxy or alpha-keto acids such as pyruvic, lactic or glycolic acids, lanolin, vaseline, aloe vera, methyl or propyl paraben, pigments and the like.

The effective amount of the compositions used to treat dermatologic conditions or diseases can vary depending on such factors as condition of the skin, age of the skin, the particular ratio of phospholipids or degree of the purity of phospholipids employed, the type of formulation and carrier ingredients used, frequency of administration, overall health of the individual being treated and the like. The precise amount for any particular patient use can be determined by those of skill in the dermatologic art taking into consideration these factors and the present disclosure. Preferably the composition is administered in at least two doses and no more than about six doses per day, or less when a sustained or delayed release form is used.

The compositions for topical, oral and parenteral administration usually contain from about 0.001% to about 10% by weight of the LPA compared to the total weight of the composition, preferably from about 0.01% to about 2% by weight of the mixture to the pharmaceutical composition, and especially from about 0.1% to about 1.5% by weight of the mixture to the pharmaceutical composition.

The topical composition is administered by applying a coating or layer to the skin or mucosal area desired to be treated. As a practical matter of convenience, the applied material is rubbed into the area. Applications need not be rubbed into the skin and the layer or coating can be left on the skin overnight.

The present invention provides compositions suitable for transdermal administration including, but not limited to, pharmaceutically acceptable lotions, suspensions, oils, creams, ointments, rinses, gels and liposomal carriers suspended in a suitable vehicle in which a therapeutically effective amount of the compositions has been admixed. Such compositions are applied directly to the skin or incorporated into a protective carrier such as a transdermal device (so-called "patch"). Examples of suitable creams, ointments etc. can be found, for instance, in the Physician's Desk Reference. Examples of suitable transdermal devices are described, for instance, in U.S. Pat. No. 4,818,540 (Chien et al.).

The present invention includes compositions suitable for parenteral administration including, but not limited to, pharmaceutically acceptable sterile isotonic solutions. Such solutions include, but are not limited to, saline and phosphate buffered saline for intravenous, intramuscular, intraperitoneal or subcutaneous injection.

The present invention includes compositions suitable for gastrointestinal administration including, but not limited to, pharmaceutically acceptable powders, pills or liquids for ingestion and suppositories for rectal administration.

The present invention includes compositions suitable for transbronchial and transalveolar administration including, but not limited to, various types of pharmaceutically acceptable aerosols for inhalation, both liquid and powder forms. An example of a drug administered in the form of an aerosol is pentamidine which is administered to AIDS patients by inhalation to prevent pneumonia caused by *Pneumocystis carnii*.

In some cases it may be desirable to perform internal delivery of LPA containing compositions in a localized area of the body, organ or tissue. The present invention encompasses methods of delivery including, but not limited to, delivery by catheter inserted into a vessel. Where delivery of the LPA containing compositions is desired to prevent or minimize damage resulting from cardiac ischemia the present invention encompasses intracoronary delivery by guide catheter.

The present invention further encompasses devices suitable for transbronchial and transalveolar administration of the compositions. Such devices include, but are not limited to, atomizers and vaporizers. The present invention also includes devices for electrical or direct injection. Electrical injection, or iontophoresis, is the process of using a small electrical current to drive charged elements, compounds and drugs through the skin to deliver the therapeutic compound to the local tissues or to the whole body without breaking the skin.

The present invention encompasses solutions suitable for flushing, perfusion, and storage of organs and tissues prior to or during transplantation. Such solutions are described in Chien et al. (1993) "Hibernation Induction Trigger for Organ Preservation" in Medical Intelligence Unit, R.G. Landes Co. Austin, Tex. The compositions described herein can be used, for instance, to replace and improve on much more impure soy preparations currently in use.

By "organ preservation solution" (OPS) is meant an aqueous solution specifically designed to preserve organs. Preferably the organ is the heart. Preferably, the solutions are used in organ transplantation, but are also useful for use in cardioplegia during open heart surgery. The OPS can also be used to flush the organ to be transplanted either prior to or after harvesting, or both. Preferably, this solution contains between about 0.00001% to about 10%, preferably about 0.001% to about 1%, more preferably about 0.005% to about 0.1%. Preferably, this solution additionally contains between about 0.1% and 20% by weight PEG. More preferably, this solution contains between about 2% and 15% by weight PEG and most preferably, this solution contains between about 8% by weight PEG. Preferably, the PEG is PEG20L.

Preferably, this solution contains between about 2% and 15% by weight PEG and can also contain effective amounts of: (a) a buffer such as NaOH, preferably about 30–40 mM, (or sufficient to result in pH of 7.2 to 7.9); (b) an impermeant anion such as Lactobionic acid, preferably about 100 mM; (c) a component providing phosphate such as $KH_2PO_4$, preferably about 25 mM; (d) a component providing potassium such as KOH, preferably about 100 mM; and (e) a component controlling cell swelling such as Raffinose, preferably about 30 mM.

Optionally, the OPS also contains effective amounts of any component known in the art of organ preservation. These include, but are not limited to glutathione, parahydroxyanisole (PHA), desferoxamine, and nitroglycerin.

The above-mentioned compositions are meant to describe, but not limit, the compositions suitable for use in the invention. The methods of producing the various compositions are within the ability of one skilled in the art and are not described in detail here. The methods of producing suitable devices for injection, topical application, atomizers and vaporizers are known in the art and will not be described in detail.

The invention further provides methods of treatment comprising administering an amount of the compositions effective to inhibit apoptosis or to preserve or restore cell, tissue or organ function. These methods entail administration of a therapeutically effective amount of the above-described compositions.

Various indications which can be treated, include, but are not limited to, those related to apoptosis, ischemia, traumatic injury and reperfusion damage. Those conditions related to apoptosis include, but are not limited to, dermatological effects of aging, the effects of reperfusion after an ischemic event, immunosuppression, gastrointestinal perturbations, cardiovascular disorders, rejection of tissue transplantation, wound healing and Alzheimer's disease. The treatment can also diminish the apoptosis-related problems associated with immunosuppressing viruses, chemotherapeutic agents, or radiation and immunosuppressive drugs.

The compositions are also suitable for use in organ transplantation during all phases of transplantation. The compositions can be used to prepare the organ by administering an amount of the compositions to the donor effective to stabilize or preserve the organ. The organ can be perfused and/or preserved in OPS containing the compositions. The organ recipient can then be administered an amount of the compositions effective to enhance organ stability and function. The compositions are also particularly suitable for use in treating cardioplegia whether related to transplantation or other surgical intervention.

Apoptosis related problems are caused by a variety of stimuli which include, but are not limited to, viruses including, but not limited to, HIV, chemotherapeutic agents, and radiation. These stimuli trigger apoptosis in a variety of disorders, including, but not limited to, those of the digestive tract tissues and associated gastrointestinal perturbations.

Gastrointestinal perturbations include, but are not limited to, damage to the lining of the gut, severe chronic ulcers, colitis, radiation induced damage, chemotherapy induced damage, and the perturbation of the gastrointestinal tract caused by parasites, and diarrhea from any other cause. Various viral and bacterial infections are known to result in gastrointestinal perturbations; the compositions are also suitable for use in treatment of the side effects associated with these infections. The compositions are particularly suited for use in ameliorating the gastrointestinal disturbances associated with chemotherapy. Thus, the compositions are suitable for use not only in preventing the diarrhea associated with chemotherapy but also the nausea.

The compositions are particularly suited to treatment of various gastrointestinal conditions in animals, including, but not limited to livestock and domesticated animals. Such conditions, particularly diarrhea, account for the loss of many calves and puppies to dehydration and malnutrition. Treatment of gastrointestinal conditions is preferably by gastrointestinal administration. In the case of cattle and domesticated animals, an effective amount of the compositions can be conveniently mixed in with the feed. In humans, administration can be by any method known in the art of gastrointestinal administration. Preferably, administration is oral.

In addition, the compositions can be administered to immunodeficient patients, particularly HIV-positive patients, to prevent or at least mitigate apoptotic death of T cells associated with the condition, which results in the exacerbation of immunodeficiencies as seen in patients with AIDS. Preferably, administration to such patients is parenterally, but can also be transdermally or gastrointestinally.

The compositions can also be administered to treat apoptosis associated with reperfusion damage involved in a variety of conditions, including, but not limited to, coronary artery obstruction; cerebral infarction; spinal/head trauma and concomitant severe paralysis; reperfusion damage due to other insults such as frostbite; coronary angioplasty, blood vessel attachment, limb attachment, organ attachment and kidney reperfusion.

Myocardial and cerebral infarctions (stroke) are caused generally by a sudden insufficiency of arterial or venous blood supply due to emboli, thrombi, or pressure that produces a macroscopic area of necrosis; the heart, brain, spleen, kidney, intestine, lung and testes are likely to be affected. Cell death occurs in tissue surrounding the infarct upon reperfusion of blood to the area; thus, the compositions are effective if administered at the onset of the infarct, during reperfusion, or shortly thereafter. The invention includes methods of treating reperfusion damage by administering a therapeutically effective amount of the compositions to a patient in need of such therapy.

The invention further encompasses a method of reducing the damage associated with myocardial and cerebral infarctions for patients with a high risk of heart attack and stroke by administering a therapeutically effective amount of the compositions to a patient in need of such therapy. Preferably, treatment of such damage is by parenteral administration of the compositions of the invention. Any other suitable method can be used, however, for instance, direct cardiac injection in the case of myocardial infarct. Devices for such injection are known in the art, for instance the Aboject cardiac syringe.

The invention further provides methods of limiting and preventing apoptosis in cells, or otherwise preserving cells, during the culture or maintenance of mammalian organs, tissues, and cells, by the addition of an effective amount of the compositions to any media or solutions used in the art of culturing or maintaining mammalian organs, tissues, and cells.

The invention further encompasses media and solutions known in the art of culturing and maintaining mammalian organs, tissues and cells, which comprise an amount of the compositions effective to preserve or restore cell, tissue or organ function, or limit or prevent apoptosis of the cells in culture.

These aspects of the invention encompass mammalian cell culture media comprising an effective amount of at least one composition and the use of such media to preserve or restore cell, tissue or organ function, or to limit or prevent apoptosis in mammalian cell culture. An effective amount is one which decreases the rate of apoptosis and/or preserves the cells, tissue or organ. The compositions have been found to limit or prevent apoptosis under circumstances in which cells are subjected to mild traumas which would normally stimulate apoptosis. Such traumas can include, but are not limited to, low level irradiation, thawing of frozen cell stocks, rapid changes in the temperature, pH, osmolarity, or ion concentration of culture media, prolonged exposure to non-optimal temperature, pH, osmolarity, or ion concentration of the culture media, exposure to cytotoxins, disassociation of cells from an intact tissue in the preparation of primary cell cultures, serum deprivation (or growth in serum-free media).

Thus, the invention encompasses compositions comprising tissue culture medium and an effective amount of the compositions. Serum-free media to which the compositions can be added as anti-apoptotic media supplements include, but are not limited to, AIM V® Media, Neuman and Tytell's Serumless Media, Trowell's T8 Media, Waymouth's MB 752/1 and 705/1 Media, and Williams' Media E. In addition to serum-free media, suitable mammalian cell culture media to which the compositions can be added as anti-apoptotic media supplements include, but are not limited to, Basal Media Eagle's, Fischer's Media, McCoy's Media, Media 199, RPMI Media 1630 and 1640, Media based on F-10 & F-12 Nutrient Mixtures, Leibovitz's L-15 Media, Glasgow Minimum Essential Media, and Dulbecco's Modified Eagle Media. Mammalian cell culture media to which the compositions can be added further comprise any media supplement known in the art, including, but not limited to, sugars, Vitamins, hormones, metalloproteins, antibiotics, antimycotics, growth factors, lipoproteins and sera.

The invention further encompasses solutions for maintaining mammalian organs prior to transplantation, which comprise an effective amount of the compositions, and the use of such solutions to preserve or restore organ function or to limit or prevent apoptosis in such mammalian organs during their surgical removal and handling prior to transplantation. The solutions can be used to flush, perfuse and/or store the organs. In all cases, concentrations of the compositions required to limit or prevent damage to the organs can be determined empirically by one skilled in the art by methods such as those found in the example provided below, as well as other methods known in the art.

It has now been found that the compositions can be topically applied to the skin to treat a variety of dermatologic conditions. These conditions include, but are not limited to, hair loss and wrinkling due to age and/or photo damage. The present invention thus encompasses methods of treating dermatological conditions. Furthermore, hair loss can be caused by apoptosis of the cells of the hair follicles. Therefore, the compositions are suitable for use in topical treatment of the skin to prevent continued hair loss. Stenn et al. (1994) *J. Invest. Dermatol.* 103:107–111.

As discussed above, these conditions are preferably treated by topical application of a composition comprising an effective amount of the compositions. An effective amount of the compositions is one which ameliorates or diminishes the symptoms of the dermatologic conditions. Preferably, the treatment results in resolution of the dermatologic condition or restoration of normal skin function; however, any amelioration or lessening of symptoms is encompassed by the invention.

The following examples are provided to illustrate but not limit the invention. Note that references to specific LPAs using compound numbers in this document refer to the compound numbers assigned in Example 1, below.

EXAMPLE 1

Structure and Synthesis of Various Analogs of Lysophosphatidic Acid

The following example sets forth the synthetic methodology and analytical data used in the construction and characterization of several lysophosphatidic acid analogs and derivatives. In addition experimental procedures and analytical data has been provided for intermediates used in the construction of these LPAs.

Contained at the end of the experimental procedures and analytical data are reaction schemes which show the synthetic routes used in compound construction. The following nomenclature and abbreviations are used in the naming of the compounds:

| | |
|---|---|
| Bn | benzyl |
| BSA | bis(trimethylsilyl)acetamide |
| t-BuOOH | tert.-butylhydroperoxide |
| CNE | cyanoethyl |
| DMAP | N,N-dimethylaminopyridine |
| DMF | N,N-dimethylformamide |
| Ile | L-isoleucine |
| Me | methyl |
| MeI | methyl iodide |
| MeOH | methanol |
| sat. | saturated |
| TBAF | tetra-butylammonium fluoride |
| TBS | tert.-butyldimethylsilyl |
| TBTU | O-benzotriazol-1-yl-N,N,N',N'-tetramethyluronium tetrafluoroborate |
| TEA | triethylamine |
| THF | tetrahydrofuran |
| TLC | thin layer chromatography |
| TMSBr | trimethylsilyl bromide |
| Tr | trityl |
| Ts | tosyl |
| Val | L-valine |
| Z | benzyloxycarbonyl |

1-O-Decyl-rac-glycerol (Compound 1)

To a stirring mixture of NaH (0.36 g, 15.1 mmol) in dry DMF (15 ml) under $N_2$ was added solketal (0.94 ml, 7.6 mmol) dropwise over a 30 min period. After 30 min, NaI (0.30 g, 2.0 mmol) was added followed by the addition of 1-chlorodecane (1.34 g, 7.6 mmol) and stirring was continued at 50° C. for 16 hours. The reaction mixture was diluted with diethyl ether (50 mL) and washed with $H_2O$ (2×50 mL), dried ($MgSO_4$) and concentrated to give a crude oil (1.48 g). The crude oil (1.06 g, 3.9 mmol) was treated with 1/1 2M HCl/THF (14 mL, v/v) for 2 hours, and the resulting solution was concentrated and redissolved in ethyl acetate (80 nml), washed with $H_2O$ (2×20 mL), dried ($MgSO_4$) and concentrated to give a yellow oil. The oil was subjected to silica-gel column chromatography [eluent: ethyl acetate/hexane, 50/50, v/v] to give the title diol (Compound 1) (58 mg, 65%) as a colourless oil.

1H NMR (360 MHz; CDCl3): d 0.87 (3 H, t, J 7 Hz, Me), 1.26 (14 H, br s, 7×CH2), 1.53–1.59 (2 H, m, b-H2), 3.41–3.55 (4 H, m, a-H2 and 1-H2 or 1-H2), 3.64 (1 H, dd, J 11.5 and 5 Hz, 1-H or 3-H), 3.72 (1 H, dd, J 11.5 and 4 Hz, 1-H or 3-H) and 3.83–3.88 (1 H, m, 2-H); ESI-MS (m/z, +ve): 231 (MH+, 100%).

1-O-Tetradecyl-rac-glycerol (Compound 2) To a mixture of solketal (5.0 mL, 40 mmol), 1-chlorotetradecane (10.9 mL, 40 mmol) and a catalytic amount of NaI in DMF (200 mL) was added NaH (3.1 g, 80 mmol) and the reaction was stirred for 16 hours at 50° C. After removal of the solvent in vacuo, the residue was redissolved in ethyl acetate (150 mL), washed with $H_2O$ (3×50 mL), dried ($MgSO_4$) and evaporated to dryness. The obtained oil was treated with 1/1 2M HCl/THF (150 mL, v/v) for 16 hours. The resulting mixture was concentrated and redissolved in ethyl acetate (150 mL), washed with $H_2O$ (3×50 mL), dried ($MgSO_4$) and evaporated to dryness. The crude product was purified by silica-gel column chromatography [eluent: $CH_2Cl_2 \rightarrow$ethyl acetate/$CH_2Cl_2$, 50/50, v/v] to yield diol Compound 2 (8.4 g, 73%) as a white solid.

1H NMR (360 MHz; CDCl3): d 0.87 (3 H, t, J 7 Hz, Me), 1.25 (22 H, br s, 11×CH2), 1.57 (2 H, quintet, J 7 Hz, b-H2), 2.38 and 2.77 (each 1 H, br s, 2×OH), 3.46 (2 H, dt, J 6.5 and 2 Hz, 1-H2 or a-H2), 3.49–3.55 (2 H, m, a-H2 or 1-H2), 3.64(1 H, dd, J 11.5 and 5 Hz, 3-H), 3.71 (1 H, dd, J 11.5 and 4 Hz, 3-H) and 3.85–3.86 (1 H, m, 2-H).

Dimethyl 3-O-tetradecyl-rac-glycero-1-phosphate (Compound 3) To a solution of diol Compound 2 (1.0 g, 3.5 mmol) and N-methylimidazole (0.45 mL, 5.6 mmol) in dry $CH_2Cl_2$ (25 mL) was added dimethyl chlorophosphate (0.42 mL, 3.9 mmol). After stirring for 3 days, the mixture was concentrated and purified by silica-gel column chromatography [eluent: hexane/ethyl acetate, 60/40, v/v] to yield phosphate Compound 3 (0.10 g, 7%) as an oil.

1H NMR (360 MHz; CDCl3): d 0.87 (3 H, t, J 7 Hz, Me), 1.25 (22 H, br s, 11×CH2), 1.55–1.58 (2 H, m, b-H2), 3.43–3.53 (4 H, m, 3-H2 and a-H2), 3.80 and 3.83 (each 3 H, s, 2×OMe), 4.00–4.02 (1 H, m, 2-H) and 4.10–4.20 (2 H, m, 1-H2); ESI-MS (m/z, +ve): 397 (MH+, 100%) and 419 ($MH^+$, 66).

3-O-Tetradecyl-rac-glycero-1-phosphate (Compound 4) To a solution of diol 2 (1.0 g, 3.5 mmol) and dibenzyl N,N-diisopropylphosphoramidite (1.16 mL, 3.5 mmol) in dry $CH_3CN$ (30 mL) was added 1H-tetrazole (0.12 g, 1.7 mmol). After stirring for 2 hours, t-BuOOH (2 mL) was added and after another 30 min the mixture was concentrated. The residue was purified by silica-gel column chromatography [eluent: hexane/ethyl acetate, 66/33, v/v) to give dibenzyl 3-O-tetradecyl-rac-glycero-1-phosphate (0.27 g, 14%) as an oil. Subsequent hydrogenolysis in MeOH (30 mL) in the presence of 10% Pd/C (0.5 g), followed by filtration over Celite and evaporation to dryness, afforded the title phosphate (Compound 4) (0.18 g, 99%) as a glass.

1H NMR (360 MHz; CDCl3): d 0.87 (3 H, t, J 6.5 Hz, Me), 1.25 (22 H, br s, 11×CH2), 1.55 (2 H, br s, b-H2), 3.45 (4 H, br s, a-H2 and 3-H2) and 4.05–4.14 (3 H, m, 2-H and 1-H2); 31P NMR(146 MHz; CDCl3): d 1.11; ESI-MS (m/z, +ve): 367 (M−H+, 100%).

1-O-Decyl-glycidol (Compound 6) To a stirring solution of glycidyl tosylate (2.0 g, 8.8 mmol) and decyl alcohol (1.34 mL, 7.0 mmol) in dry $CH_2Cl_2$ (40 mL) under N2 was added a $BF_3.OEt_2$ solution (~2.2 mL, ~10% in CH2Cl2). After 48 hours, TLC analysis showed the reaction to be complete and the solvent was removed in vacuo to give 1-O-decyl-rac-glycero-3-p-toluenesulfonate (Compound 5) as an oil.

Crude Compound 5 was taken up in 50% aqueous MeOH (30 mL), NaOH (1.4 g, 35.0 mmol) was added and the mixture was left to stir for 16 hours. TLC analysis showed the reaction to be complete and the mixture was concentrated to remove MeOH. The remaining aqueous phase was extracted with diethyl ether (2×40 mL) and the combined organic phases were washed with $H_2O$ (30 mL), sat. $NaHCO_3$ (30 mL), dried ($MgSO_4$) and concentrated. The residue was subjected to silica-gel column chromatography [eluent: ethyl acetate/hexane, 91/9, v/v] to give epoxide Compound 6 (0.93 g, 62%) as a colourless oil.

1H NMR (360 MHz; CDCl3): d 0.87 (3 H, t, J 7 Hz, Me), 1.26 (14 H, br s, 7×CH2), 1.58 (2 H, m, b-H2), 2.61(1 H, dd, J 5 and 2.5 Hz, 3-H), 2.80 (1 H, t, J 4.5 Hz, 3-H), 3.13–3.17 (1 H, m, 2-H), 3.38 (1 H, dd, J 11.5 and 6 Hz, 1-H), 3.42–3.54 (2 H, m, a-H2) and 3.70 (1 H, dd, J 11.5 and 3 Hz, 1-H).

1-O-Tetradecyl-glycidol (Compound 8) To a solution of glycidyl tosylate (2.0 g, 8.8 mmol) and 1-tetradecanol (1.5 g, 7.0 mmol) in dry $CH_2Cl_2$ (40 mL) under $N_2$ was added a $BF_3.OEt_2$ solution (~2.2 mL, ~10% in $CH_2Cl_2$). After 48 hours, TLC analysis showed the reaction to be complete and the solvent was removed in vacuo to give 1-O-tetradecyl-rac-glycero-3-p-toluenesulfonate (Compound 7) as an oil.

Crude Compound 7 was taken up in 50% aq. MeOH (30 mL), NaOH (1.4 g, 35.0 mmol) was added and the mixture was left to stir for 16 hours. TLC analysis showed the reaction to be complete and the mixture was concentrated to remove MeOH. The remaining aqueous phase was extracted with diethyl ether (2×40 mL) and the combined organic phases were washed with $H_2O$ (30 mL), sat. $NaHCO_3$ (30 mL), dried ($MgSO_4$) and evaporated to dryness. The residue was subjected to silica-gel column chromatography [eluent: ethyl acetate/hexane, 91/9, v/v] to give epoxide Compound 8 (1.57 g, 83%) as a colourless oil.

1H NMR (360 MHz; CDCl3): d 0.88 (3 H, t, J 7 Hz, Me), 1.25 (22 H, m, 11×CH2), 1.57 (2 H, m, b-H2), 2.61(1 H, dd, J 5.5 and 3 Hz, 3-H), 2.80 (1 H, t, J 4.5 Hz, 3-H), 3.13–3.17 (1 H, m, 2-H), 3.38 (1 H, dd, J 11.5 and 6 Hz, 1-H), 3.42–3.54 (1 H, m, a-H2) and 3.70 (1 H, dd, J 11.5 and 6 Hz, 1-H).

1-O-Oleyl-glycidol (Compound 10) To a solution of glycidyl tosylate (2.0 g, 8.8 mmol) and oleyl alcohol (1.88 mL, 7.0 mmol) in dry $CH_2Cl_2$ (40 mL) under $N_2$ was added a $BF_3OEt_2$ solution (~2.2 mL, ~10% in $CH_2Cl_2$). After 48 hours, TLC analysis showed the reaction to be complete and the solvent was removed in vacuo to give 1-O-oleyl-rac-glycero-3-p-toluenesulfonate (Compound 9) as an oil.

Crude Compound 9 was taken up in 50% aq. MeOH (30 mL) to which NaOH (1.4 g, 35.0 mmol) was added. After 16 hours, TLC analysis showed the reaction to be complete and the mixture was concentrated to remove MeOH. The remaining aqueous phase was extracted with diethyl ether (2×40 mL) and the combined organic phases were washed with $H_2O$ (30 mL), sat. $NaHCO_3$ (30 mL), dried ($MgSO_4$) and concentrated. The residual oil was purified by silica-gel column chromatography [eluent: ethyl acetate/hexane, 91/9, v/v] to furnish epoxide Compound 10 (1.65 g, 72%) as a colourless oil.

1H NMR (360 MHz; CDCl3): d 0.88 (3 H, t, J 6.5 Hz, Me), 1.28 (22 H, apparent br d, separation 9 Hz, —(CH2)5- and —(CH2)6-), 1.58 (2 H, br s, b-H2), 2.01 (4 H, apparent br d, separation 4.5 Hz, —CH2CH═CHCH2-), 2.61 (1 H, br s, 3-H), 2.80(1 H, br t, J 4 Hz, 3-H), 3.15 (1 H, br s,2-H), 3.38 (1 H, dd, J 11.5 and 6 Hz, 1-H), 3.45–3.54 (2 H, m, a-H2), 3.69–3.72 (1 H, m, 1-H) and 5.34 (2H, br s, —CH2CH═CHCH2-).

3-O-Decyl-rac-glycero-1-phosphate (Compound 11) A mixture of 98% phosphoric acid (0.18 g, 1.9 mol) and decyl glycidol (Compound 6) (0.4 g, 1.9 mmol) in dry $CH_2Cl_2$ was refluxed for 2 hours until TLC analysis showed the reaction to be complete. Then, the reaction mixture was concentrated to afford phosphate Compound 11 (0.56 g, 78%) as a colourless oil.

1H NMR (360 MHz; CDCl3): d 0.87 (3 H, t, J 6.5 Hz, Me), 1.25 (14 H, br s, 7×CH2), 1.56 (2 H, br s, b-H2), 3.44–3.53 (4 H, m, a-H2 and 3-H2) and 3.61–4.13 (3 H, m, 2-H and 1-H2); 31P NMR (146 MHz; CDCl3): d 1.41; ESI-MS (m/z, -ve): 311 (M−H+, 100%).

3-O-Oleyl-rac-glycero-1-phosphate (Compound 12) A mixture of 98% phosphoric acid (0.18 g, 1.9 mol) and oleyl glycidol (Compound 10) (0.4 g, 1.2 mmol) in dry $CH_2Cl_2$ was refluxed for 16 hours. TLC analysis showed the reaction to be complete and the mixture was concentrated to give the title phosphate (Compound 12) (0.501 g, 96%) as a colourless oil.

1H NMR (360 MHz; CDCl3): d 0.87 (3 H, t J 6.5 Hz, Me), 1.27 (22 H, apparent br d, separation 6 Hz, —(CH2)5- and —(CH2)6-), 1.55 (2 H, br s, b-H2), 1.98–2.03 (4 H, m, —CH2CH═CHCH2-), 3.44–3.51 (4 H, m, 3-H2 and a-H2), 3.53–4.12 (3 H, , 2-H and 1-H2), 5.30–5.38 (2H, m, —CH2CH═CHCH2-) and 6.43 (2H, br s, 2×OH); 31P NMR (146 MHz; CDCl3): d 1.68; ESI-MS (m/z, -ve): 421 (M−H+, 100%).

Dimethyl 3-oleyloxypropyl-1-phosphate (Compound 15) To a suspension of NaH (0.40 g, 13.1 mmol) and anhydrous NaI (1.98 g, 13.4 mmol) in dry DMF (30 mL) under $N_2$ was added dropwise 1,3-propanediol (0.95 mL, 13.1 mmol) over a 30 min period. Next, oleyl tosylate (13) (5.6 g, 13.1 mmol) was added and stirring was continued for 16 hours at 50° C. The reaction mixture was quenched with water (50 mL) and extracted with diethyl ether (2×100 mL). The combined organic phases were dried ($MgSO_4$) and concentrated to give crude alcohol Compound 14.

To a solution of Compound 14 (0.51 g, 1.6 mmol) in dry $CH_2Cl_2$ (10 mL) was added N-methylimidazole (0.28 mL, 3.5 mmol) followed by the addition of dimethyl chlorophosphate (0.2 mL, 1.9 mmol). After 16 hours, the reaction was quenched with sat. $KHSO_4$ (20 mL) and extracted with ethyl acetate (3×50 mL). The organic phases were washed with sat. NaCl (40 mL), dried ($MgSO_4$) and concentrated to give protected phosphate Compound 15 as a yellow oil.

1H NMR (360 MHz; CDCl3): d 0.88 (3 H, t J 7 Hz, Me), 1.27 (22 H, apparent br d, separation 12 Hz, —(CH2)5- and —(CH2)6-), 1.55–1.57 (2 H, m, b-H2), 1.95–2.01 (6 H, m, —CH2CH═CHCH2- and 2-H2), 3.41–3.43 (2 H, t, J 6 Hz, α-H2), 3.57 (2 H, t, J 6.5 Hz, 3-H2), 3.77 and 3.80 (each 3 H, s, 2×OMe), 4.20 (2H, m, 1-H2) and 5.33–5.38 (2 H, m, —$CH_2$CH═CH$CH_2$—); ESI-MS (m/z, +ve): 435 (MH+, 100%).

3-O-Oleyloxypropyl-1-phosphate (Compound 16) To a solution of dimethyl phosphate Compound 15 (0.26 g, 0.59 mmol) in dry $CH_2Cl_2$ (8 mL) was added BSA (0.30 mL, 1.2 mmol) followed by the addition of TMSBr (0.24 mL, 1.8 mmol). After 15 min, TLC analysis showed complete consumption of the starting material and the reaction was quenched with 1/1 MeOH/$H_2O$ (2 mL, v/v) for 15 min, followed by the addition of sat. $KHSO_4$ (5 mL). The reaction mixture was subsequently extracted with ethyl acetate (2×30 mL), the organic extracts were combined, dried ($MgSO_4$) and concentrated to give the title phosphate (Compound 16) as an oil.

$^1$H NMR (360 MHz; CDCl$_3$): δ 0.88 (3 H, t, J 7 Hz, Me), 1.27 (22 H, apparent br d, separation 6 Hz, —(CH$_2$)$_5$— and —(CH$_2$)$_6$—), 1.56 (2 H, br s, β-H$_2$), 1.95–2.01 (6 H, m, 2-H$_2$ and —CH$_2$CH═CHCH$_2$—), 3.43 (2 H, t, J 6 Hz, α-H$_2$), 3.57 (2 H, br s, 3-H$_2$), 4.12 (2 H, br s, 1-H$_2$), 5.33–5.38 (2 H, m, —CH$_2$CH═CHCH$_2$—) and 8.06 (2 H, br s, 2×OH); $^{31}$P NMR (146 MHz; CDCl$_3$): δ 1.95; ESI-MS (m/z, -ve): 405 (M−H+, 100%).

3-Hydroxypropyl decyl ether (Compound 17) To a mixture of NaH (2.6 g, 70 mmol) and anhydrous NaI (9.9 g, 70 mmol) in dry DMF (80 mL) under $N_2$ was added dropwise a solution of 1,3-propanediol (4.75 mL, 70 mmol) in DMF (20 mL). The mixture was stirred until hydrogen evolution had ceased, decyl chloride (1.34 g, 7.6 mmol) was added and stirring was continued at 50° C. for 18 hours. Then, the reaction mixture was poured into $H_2O$ (300 mL) and extracted with diethyl ether (3×250 mL). The organic extracts were combined, washed with sat. NaCl (100 mL), dried ($MgSO_4$) and evaporated to dryness. The residue was subjected to silica-gel column chromatography [eluent: ethyl acetate/hexane, 30/70, v/v] to furnish decyl ether Compound 17 as a colourless oil.

$^1$H NMR (360 MHz; CDCl$_3$): δ 0.87 (3 H, t, J 7 Hz, Me), 1.25 (14 H, br s, 7×CH$_2$), 1.55 (2 H, quintet, J 7 Hz, β-H$_2$), 1.82 (2 H, quintet, J 5.5 Hz, 2-H$_2$), 2.62 (1 H, br s, OH), 3.41 (2 H, t, J 7.5 Hz, α-H$_2$), 3.60 (2 H, t, J 5.5 Hz, 1-H$_2$), and 3.77 (2 H, t, J 5.5 Hz, 3-H$_2$); ESI-MS (m/z, +ve): 217 (MH+, 100%).

3-Decyloxypropyl-1-phosphate (Compound 19) To a solution of alcohol Compound 17 (0.5 g, 2.3 mmol) in dry $CH_2Cl_2$ (20 mL) was added TEA (0.48 mL, 3.5 mmol) followed by the addition of trimethyl phosphite (0.41 mL, 3.5 mmol). After 90 min, the reaction was cooled to −40° C., pyridinium tribromide (0.89 g, 2.8 mmol) was added and the reaction was allowed to warm to 20° C. overnight. The mixture was subsequently quenched with sat. $KHSO_4$ (30 mL) and extracted with ethyl acetate (2×50 mL). The organic extracts were combined, washed with sat. NaCl (30 mL), dried ($MgSO_4$) and concentrated to give phosphate triester Compound 18.

$^1$H NMR (360 MHz; CDCl$_3$): δ 0.87 (3 H, t, J 6.5 Hz, Me), 1.25 (14 H, br s, 7×CH$_2$), 1.50–1.56 (2 H, m, β-H$_2$), 1.93 (2 H, quintet, J 6 Hz, 2-H$_2$), 3.39 (2 H, t, J 6.5 Hz, α-H$_2$ or 3-H$_2$), 3.49 (2 H, t, J 6 Hz, α-H$_2$ or 3-H$_2$), 3.74 and 3.77 (each 3 H, s, 2×OMe) and 4.14 (2 H, quartet, J 6.5 Hz, 1-H$_2$).

To a stirring solution of phosphate triester Compound 18 (0.25 g, 0.72 mmol) in dry $CH_2Cl_2$ (5 mL) was added BSA (0.25 mL, 1.0 mmol) followed by the addition of TMSBr (0.3 mL, 2.3 mmol). After 15 min, TLC analysis showed complete consumption of the starting material and the reaction was quenched with 1/1 MeOH/$H_2O$ (2 mL, v/v) for 15 min, followed by the addition of sat. $KHSO_4$ (5 mL). The reaction mixture was subsequently extracted with ethyl acetate (2×30 mL), and the combined organic extracts were dried ($MgSO_4$) and concentrated to give the title phosphate (Compound 19) as an oil.

$^1$H NMR (360 MHz; CDCl$_3$): δ 0.88 (3 H, t, J 7 Hz, Me), 1.27 (14 H, br s, 7×CH$_2$), 1.55–1.58 (2 H, m, β-CH$_2$), 1.95 (2 H, br s, 2-H2), 3.42–3.48 (4 H, m, α-H$_2$ and 3-H$_2$), 4.10 (2 H, br s, 1-H$_2$) and 6.35 (2 H, br s, 2×OH); ESI-MS (m/z, -ve): 295 (M−H+, 100%).

Dimethyl 1-O-oleyl-2-O-methyl-rac-glycero-1-phosphate (Compound 23) To a solution of tosyl chloride (19.1 g, 0.10 mol) in dry $CH_2Cl_2$ (200 mL) at 0° C. was added TEA (15.3 mL, 0.10 mol) and oleyl alcohol (37.2 mL, 0.10 mol). The reaction mixture was allowed to warm to 20° C. and was subsequently stirred for 3 days. Next, the solvent was removed in vacuo and the resulting residue was redissolved in ethyl acetate (400 mL), washed with sat. $NaHCO_3$ (40 mL), dried ($MgSO_4$), concentrated and subjected to silica-gel column chromatography [eluent: hexane/$CH_2Cl_2$, 66:33, v/v] to give oleyl tosylate (Compound 13) as an oil.

To a mixture of NaH (4.8 g, 120 mmol) and NaI (0.2 g) in dry DMF (20 mL) was added solketal (5.0 mL, 40 mmol)

dropwise over a 30 min period. Once the effervescence had stopped, oleyl tosylate (Compound 13) (16.9 g, 40 mmol) was added and the reaction mixture was left for 3 days at 50° C. Then, $H_2O$ (10 mL) was added and the mixture was extracted with diethyl ether (2×100 mL), the combined organic phases were dried ($MgSO_4$) and evaporated to dryness. The residue was taken up in THF (150 mL), 2M HCl was added until the solution turned turbid and the reaction was left to stir for 16 hours. The mixture was concentrated and subjected to silica-gel column chromatography [eluent: ethyl acetate/hexane, 50/50, v/v] to give 1-O-oleyl-rac-glycerol (Compound 20) as an oil.

Diol Compound 20 (2.0 g, 5.97 mmol) was added dropwise to a solution of trityl chloride (1.66 g, 6.0 mmol) in anhydrous pyridine (10 mL). The reaction was left to stir for 16 hours after which the solvent was removed by co-evaporation with toluene (2×5 mL). Then, part of the residue (1.0 g, 1.7 mmol) was added dropwise to a suspension of NaH (0.14 g, 3.4 mmol) in THF (50 mL), followed by the addition of MeI (0.22 mL, 3.4 mmol). After 16 hours, TLC analysis showed that the reaction had gone to completion and $H_2O$ (5 mL) was added followed by concentration of the reaction mixture. The residue was partitioned between $H_2O$ (20 mL) and diethyl ether (100 mL), the organic extract was washed with sat. $NaHCO_3$ (10 mL), dried ($MgSO_4$) and concentrated to give 1-O-oleyl-2-O-methyl-3-O-trityl glycerol (Cornpound 21) as an oil.

Crude Compound 21 (1.16 g) was dissolved in $CH_2Cl_2$ (10 mL) after which trifluoroacetic acid (2 mL) was added. The reaction mixture was stirred for 5 min and excess TFA was quenched by adding solid $NaHCO_3$ until effervescence ceased. The mixture was diluted with $H_2O$ (10 mL), extracted with $CH_2Cl_2$ (2×50 mL) and the combined organic phases were dried ($MgSO_4$), concentrated and subjected to silica-gel column chromatography [eluent: hexane/ethyl acetate, 80/20, v/v] to give glycerol derivative Compound 22 (0.28 g, 42%) as an oil.

$^1$H NMR (360 MHz; $CDCl_3$): δ 0.88 (3 H, t J 7 Hz, Me), 1.27 (22 H, apparent br d, separation 9.5 Hz, —$(CH_2)_5$— and —$(CH_2)_6$—), 1.53–1.60 (2 H, n, —H2), 1.98–2.01 (4 H, m, —$CH_2CH=CHCH_2$—), 3.37–3.46 (3 H, m, 2-H and α-$H_2$), 3.47 (3H, s, OMe), 3.52 (1 H, dd, J 10 and 5 Hz, 1-H), 3.56 (1 H, dd, J 10 and 5 Hz, 1-H), 3.65 (1 H, dd, J 11.5 and 5.5 Hz, 3-H), 3.76 (1 H, dd, J 11.5 and 4 Hz, 3-H) and 5.30–5.39 (2 H, m, —$CH_2CH=CHCH_2$—).

To a solution of compound Compound 22 (0.26 g, 0.76 mmol) in dry $CH_2Cl_2$ (8 mL) was added N-methylimidazole (67 μl, 0.84 mmol) followed by the addition of dimethyl chlorophosphate (0.12 mL, 1.22 mmol). After 1 hours, TLC analysis showed the reaction to be complete, sat. $KHSO_4$ (20 mL) was added and the mixture was extracted with ethyl acetate (3×50 mL). The organic phases were combined and washed with sat. NaCl (40 mL), dried ($MgSO_4$), concentrated and subjected to silica-gel column chromatography [eluent: ethyl acetate/hexanes, 50/50, v/v] to give the title dimethyl phosphate (Compound 23) as an oil.

$^1$H NMR (360 MHz; $CDCl_3$): δ 0.88 (3 H, t J 7 Hz, Me), 1.27 (22 H, apparent br d, separation 12 Hz, —$(CH_2)_5$— and —$(CH_2)_6$—), 1.54–1.59 (2 H, n, β-$H_2$), 1.98–2.01 (4 H, m, —$CH_2CH=CHCH_2$—), 3.41–3.56 (5 H, m, 2-H, 3-$H_2$ and α-$H_2$), 3.47 (3 H, s, OMe), 3.77 (3 H, d, J 2 Hz, OMe), 3.80 (3 H, d, J 2 Hz, OMe), 4.08 (1 H, ddd, J 11, 7.0 and 5.5 Hz, 1-H), 4.19 (1 H, ddd, J 11, 7.0 and 4 Hz, 1-H) and 5.30–5.39 (2 H, m, —$CH_2CH=CHCH_2$—); $^{31}$P NMR (146 MHz; $CDCl_3$): δ 2.60; ESI-MS (m/z, +ve): 465 ($MH^+$, 100%).

3-O-Oleyl-2-O-methyl-rac-glycero-1-phosphate (Compound 24) To a stirring solution of protected phosphate Compound 23 (85 mg, 0.18 mmol) in dry $CH_2Cl_2$ (5 mL) was added BSA (140 μL, 0.55 mmol) and TMSBr (50 μL, 0.05 mmol). After 30 min, TLC analysis showed the reaction to be complete, 1/1 $MeOH/H_2O$ (1 mL, v/v) was added and left for 30 min. Then, sat. KHSO4 (5 mL) was added and the mixture was extracted with ethyl acetate (2×30 mL), the combined organic extracts were dried ($MgSO_4$), evaporated to dryness and subjected to Sephadex LH-20 column chromatography [eluent: $MeOH/CH_2Cl_2$, 50/50, v/v] to give phosphate Compound 24 as an oil.

$^1$H NMR (360 MHz; $CDCl_3$): δ 0.87 (3 H, t J 7 Hz, Me), 1.25 (22 H, apparent br d, separation 4 Hz, —$(CH_2)_5$— and —$(CH_2)_6$—), 1.55–1.56 (2 H, β-$H_2$), 1.98–2.03 (4 H, m, —$CH_2CH=CHCH_2$—), 3.40–3.58 (5 H, m, 2-H, 3-H2 and α-$H_2$), 3.46 (3 H, s, OMe), 3.99–4.05 (2 H, m, 1-H2), 5.30–5.37 (2 H, m, —$CH_2CH=CHCH_2$—) and 5.75 (2 H, br s, 2×OH); $^{31}$P NMR (146 MHz; $CDCl_3$): δ 1.68; ESI-MS (m/z, -ve): 435 (M–$H^+$, 100%).

Dimethyl 3-O-oleyl-rac-glycero-1-thiophosphate (Compound 25) To a solution of 1-O-Oleyl-glycerol (Compound 20) (1.5 g, 4.4 mmol) and dimethyl chlorothiophosphate (0.80 mL, 6.57 mmol), dried by azeotropic removal of $H_2O$ with $CH_3CN$ (2×15 mL), in $CH_2Cl_2$ (20 mL) under $N_2$ was added N-methylimidazole (0.70 mL, 8.8 mmol). After 3 days, the mixture was concentrated and subjected to silica-gel column chromatography [eluent: hexane:ethyl acetate, 90/10, v/v] to give protected thiophosphate Compound 25 (0.17 g, 25%) as an oil.

$^1$H NMR (360 MHz; $CDCl_3$): δ 0.87 (3 H, t, J 6 Hz, Me), 1.27 (22 H, apparent br d, separation 12 Hz, —$(CH_2)_5$— and —$(CH_2)_6$—), 1.54–1.58 (2 H, m, β-$H_2$), 1.98–2.04 (4 H, m, —$CH_2CH=CHCH_2$—), 3.44–3.53 (2 H, m, 3-$H_2$), 3.75 and 3.79 (each 3 H, s, 2×OMe), 3.97–4.03 (1 H, m, 2-H), 4.04–4.18 (2 H, m 1-$H_2$) and 5.30–5.35 (2 H, m, —$CH_2CH=CHCH_2$—); ESI-MS (m/z, +ve): 467 ($MH^+$, 52%), 489 ($MNa^+$, 100) and 505 ($MK^+$, 20%).

3-Hydroxypropyl oleate (Compound 28) To a solution of 1,3-propanediol (3.61 mL, 50.0 mmol) in pyridine (100 mL) was added chlorotriphenylmethane (14 g, 50.0 mmol) and the mixture was stirred at 70° C. for 16 hours. The solvent was removed by co-evaporation with dry toluene (2×50 mL) and the resulting residue was redissolved in diethyl ether (150 mL), washed with $H_2O$ (2×50 mL), dried ($MgSO_4$), concentrated and purified by silica-gel column chromatography [eluent: hexane/ethyl acetate, 90/10, v/v] to give monotritylated diol Compound 26.

$^1$H NMR (360 MHz; $CDCl_3$): δ 1.82 (2 H, quintet, J 6 Hz, 2-$H_2$), 3.23 (2H, t, J 6 Hz, 1-$H_2$ or 3-$H_2$), 3.72 (2 H, t, J 5.5 Hz, 1-$H_2$ or 3-$H_2$), 7.18–7.28 (10H, m, 2×Ph) and 7.34–7.40 (5 H, m, Ph).

To a solution of Compound 26 (3.2 g, 10 mmol) and DMAP (50 mg) in pyridine (10 mL) was added oleoyl chloride (3.3 g, 10 mmol). After 4 hours, pyridine was removed by co-evaporation with dry toluene (2×50 ml) and the obtained residue was partitioned between diethyl ether (150 mL) and $H_2O$ (50 mL). The diethyl ether layer was subsequently washed with sat. NaCl (50 mL), dried ($MgSO_4$) and evaporated to dryness. The residue was purified by silica-gel column chromatography [eluent: hexane/ diethyl ether, 90/10, v/v] to give trityl ester 27.

Treatment of a solution of Compound 27 (3.72 g, 6.39 mmol) in dry $CH_2Cl_2$ (100 mL) with trifluoroacetic acid (5 mL) resulted in a bright yellow solution. Subsequently, the mixture was quenched by the addition of $H_2O$ (10 mL) and solid $NaHCO_3$ (5 g). The product was extracted into $CH_2Cl_2$ (2×100 mL), the organic phases were combined, dried (MgSO$_4$) and concentrated. Purification of the residue by silica-gel column chromatography [eluent: ethyl acetate/hexanes, 30/70, v/v] furnished the title alcohol (Compound 28) (2.1 g, 95%) as an oil.

$^1$H NMR (360 MHz; CDCl$_3$): δ 0.87 (3 H, t, J 7 Hz, Me), 1.28 (20 H, apparent br d, separation 13.5 Hz, —(CH$_2$)$_4$— and —(CH$_2$)$_6$—), 1.60–1.63 (2 H, m, β-H$_2$), 1.86 (2 H, quintet, J 6 Hz, 2-H$_2$), 1.98–2.01 (4 H, m, —CH$_2$CH=CHCH$_2$—), 2.31 (2 H, t, J 7.5 Hz, α-H$_2$), 3.68 (2 H, t, J 6 Hz, 3-H$_2$), 4.24 (2 H, t, J 6 Hz, 1-H$_2$), and 5.29–5.39 (2 H, m, —CH$_2$CH=CHCH$_2$—).

Dimethyl 1-(3-propyl oleoate)phosphate (Compound 29) To a solution of alcohol Compound 28 (0.52 g, 1.5 mmol) and N-methylimidazole (0.27 mL, 3.3 mmol) in dry CH$_2$Cl$_2$ (5 mL) was added dimethyl chlorophosphate (0.2 mL, 1.8 mmol). After 1 hours, TLC analysis showed the reaction to be complete, sat. KHSO$_4$ (20 mL) was added and the mixture was extracted with ethyl acetate (3×50 mL), the combined organic phases were washed with sat. NaCl (40 mL), dried (MgSO$_4$) and concentrated. The residue was subjected to silica-gel column chromatography [eluent: ethyl acetate/hexanes, 50/50, v/v] to give protected phosphate Compound 29 as an oil.

$^1$H NMR (360 MHz; CDCl$_3$): δ 0.87 (3 H, t, J 7 Hz, Me), 1.28 (20 H, apparent br d, separation 13 Hz, —(CH$_2$)$_5$— and —(CH$_2$)$_6$—), 1.59–1.64 (2 H, m, β-H$_2$), 1.98–2.04 (6 H, m, 2-H$_2$ and —CH$_2$CH=CHCH$_2$—), 2.30 (2 H, t, J 7.5 Hz, α-H$_2$), 3.75 and 3.78 (each 3 H, s, 2×OMe), 4.11–4.20 (4 H, m, 1-H$_2$ and 3-H$_2$), 5.29–5.39 (2 H, m, —CH$_2$CH=CHCH$_2$—); $^{31}$P NMR (146 MHz; CDCl$_3$): δ 2.54; ESI-MS (m/z, +ve): 449 (MH$^+$, 100%) and 466 (M+18$^+$, 89).

1-(3-propyl oleoate)phosphate (Compound 30) To a stirring solution of dimethyl phosphate 29 (0.31 g, 0.7 mmol) in dry CH$_2$Cl$_2$ (4 mL) was added BSA (0.52 mL, 2.1 mmol) followed by the addition of TMSBr (0.19 mL, 1.4 mmol). After 30 min, TLC analysis showed complete consumption of the starting material, the reaction was quenched with 1/1 MeOH/H$_2$O (1 mL, 1/1) for 30 min, followed by the addition of sat. KHSO$_4$ (5 mL). The mixture was extracted with ethyl acetate (2×30 mL), the organic extracts were combined, dried (MgSO$_4$) and evaporated to dryness. Purification of the residue by Sephadex LH-20 column chromatography [eluent: MeOH/CH$_2$Cl$_2$, 50/50, v/v] gave the title phosphate (Compound 30) as an oil.

$^1$H NMR (360 MHz; CDCl$_3$): δ 0.87 (3 H, t, J 7 Hz, Me), 1.28 (20 H, apparent br d, separation 11 Hz, —(CH$_2$)$_4$— and—(CH$_2$)$_6$—), 1.57–1.61 (2 H, m, β-H$_2$), 2.00 (6 H, apparent br d, separation 3.5 Hz, —CH$_2$CH=CHCH$_2$— and 2-H$_2$), 2.30 (2H, t, J 7.5 Hz, α-H$_2$), 4.11 (2 H, quartet, J 6 Hz, 3-H$_2$), 4.19 (2 H, t, J 6.5 Hz, 1-H$_2$), 5.29–5.38 (2 H, m, —CH$_2$CH=CHCH$_2$—) and 9.24 (2 H, br s, 2×OH); $^{31}$P NMR (146 MHz; CDCl$_3$): δ 1.80; ESI-MS (m/z, -ve): 419 (M-H$^+$, 100%).

Dimethyl 3-O-oleoyl-2-deoxy-2-bromo-rac-glycero-1-phosphate (Compound 36) To a stirring solution of 1-O-benzyl-2-deoxy-2-bromo-rac-glycerol (0.5 g, 2.0 mmol), dimethyl chlorophosphate (270 μL, 2.5 mmol) in dry CH$_2$Cl$_2$ (20 mL) under N$_2$ was added N-methylimidazole (180 μL, 2.2 mmol). After 3 days, the mixture was concentrated and purified by silica-gel column chromatography [eluent: ethyl acetate/hexane, 50/50, v/v] to yield dimethyl 3-O-benzyl-2-deoxy-2-bromo-rac-glycero-1-phosphate (Compound 34) (0.43 g, 59%) as an oil.

$^1$H NMR (360 MHz; CDCl$_3$): δ 3.73–3.81 (2 H, m, 3-H$_2$), 3.75 (3 H, apparent d, separation 13.5 Hz, OMe), 3.78 (3 H, appparent d, separation 14 Hz, OMe), 4.21 (1 H, quintet, J 5.5 Hz, 2-H), 4.28–4.40 (2 H, m, 1-H$_2$), 4.57 (2 H, br s, —OCH$_2$Ph) and 7.26–7.37 (5 H, m, -Ph); $^{31}$P NMR (146 MHz; CDCl$_3$): δ 1.88; ESI-MS (m/z, +ve): 353 and 355 (MH$^+$, 100%).

A mixture of bromo Compound 34 (0.43 g, 1.2 mmol) and 10% palladium on activated carbon (0.43 g) in ethyl acetate (50 mL) was evacuated using an aspirator pump and filled with hydrogen. After 2 hours, TLC analysis showed the reaction to be complete and the mixture was filtered through Celite. The filtrate was evaporated to dryness to furnish dimethyl 2-deoxy-2-bromo-rac-glycero-1-phosphate (Compound 35) (0.28 g, 88%) as a colourless oil.

$^1$H NMR (360 MHz; CDCl$_3$): δ 2.35 (1 H, br s, OH), 3.80 (3 H, d, J 7 Hz, OMe), 3.83 (3 H, d, J 6.5 Hz, OMe), 3.89 (1 H, dd, J 12.5 and 6 Hz, 3-H), 3.94 (1H, dd, J 12.5 and 5 Hz, 3-H), 4.13–4.19 (1 H, m, 2-H), 4.31 (1 H, ddd, J 11.5, 9.5 and 6 Hz, 1-H) and 4.46 (1 H, ddd, J 11.5, 9 and 4.5 Hz, 1-H).

To a solution of alcohol Compound 35 (0.28 g, 1.1 mmol) in dry CH$_2$Cl$_2$ (5 mL) under N$_2$ was added oleoyl chloride (0.39 mL, 1.2 mmol) followed by the addition of pyridine (0.09 mL, 1.2 mmol). After 1 hour, the mixture was concentrated and subjected to silica-gel column chromatography [eluent: ethyl acetate (20–50%) in hexane, v/v] to give phosphate Compound 36 (0.48 g, 85%) as an oil.

$^1$H NMR (360 MHz; CDCl$_3$): δ 0.86 (3 H, t, J 7 Hz, Me), 1.25 (20 H, apparent doublet, separation 14 Hz, —(CH$_2$)$_4$— and —(CH$_2$)$_6$—), 1.58–1.62 (2 H, m, β-H$_2$), 1.97–1.98 (4 H, m, —CH$_2$CH=CHCH$_2$—), 2.33 (2 H, t, J 7.5 Hz, α-H$_2$), 3.76 (3H, d, J 1.5 Hz, OMe), 3.79 (3 H, d, J 2 Hz, OMe), 4.20–4.31 (3 H, m, 2-H and 3-H$_2$), 4.36 (1 H, dd, J 12 and 5 Hz, 1-H), 4.40 (1 H, dd, J 12 and 5.5 Hz, 1-H) and 5.26–5.36 (2 H, m, —CH$_2$CH=CHCH$_2$—); $^{31}$P NMR (146 MHz; CDCl$_3$): δ 1.82; ESI-MS (m/z, +ve): 527 and 529 (MH$^+$, 29%), 549 and 551 (MH$^+$, 49) and 565 and 567 (MH$^+$, 100).

3-O-Oleoyl-2-deoxy-2-bromo-rac-glycero-1-phosphate (Compound 37)

To a solution of bromo alcohol Compound 36 (0.20 g, 0.38 mmol) in dry CH$_2$Cl$_2$ (20 mL) under N$_2$ was added BSA (0.21 ml, 0.83 mmol) followed by the addition of TMSBr (0.11 mL, 0.83 mmol). The reaction was carefully monitored by TLC and after 85 min all the starting material had been consumed. Then, 1/1 MeOH/H$_2$O (3 mL, v/v) was added and the mixture was stirred for a subsequent 15 min after which sat. KHSO$_4$ (5 mL) was added. The mixture was subsequently extracted with ethyl acetate (3×10 mL), the organic extracts were combined, dried (MgSO$_4$), concentrated and subjected to Sephadex LH-20 column chromatography [eluent: MeOH/CH$_2$Cl$_2$, 50/50, v/v] to give the title phosphate (Compound 37) (0.19 g, 99%) as a yellow oil.

$^1$H NMR (360 MHz; CDCl$_3$): δ 0.87 (3 H, t, J 7 Hz, Me), 1.28 (20 H, apparent doublet, separation 13.5 Hz, —(CH$_2$)$_4$— and —(CH$_2$)$_6$—), 1.61–1.62 (2 H, m, β-H$_2$), 1.99–2.01(4 H, m, —CH$_2$CH=CHCH$_2$—), 2.36 (2 H, t, J 7 Hz, α-H$_2$), 4.19–4.28 (3 H, m, 2-H and 3-H$_2$), 4.37 (1 H, dd, J 12 and 5 Hz, 1-H), 4.47 (1 H, dd, J 12 and 5 Hz, 1-H), 5.29–5.38 (2 H, m, —CH$_2$CH=CHCH$_2$—) and 9.05 (2 H, s, 2×OH); $^{31}$P NMR (146 MHz; CDCl$_3$): δ 1.08; ESI-MS (m/z, -ve): 499 and 501 (M-H$^+$, 100%).

1-O-Oleoyl-2-O-methyl-rac-glycerol (Compound 44) To a mixture of 1-O-benzyl-glycerol (27 mL, 0.16 mol) and t-butyldimethylsilyl chloride (25 g, 0.17 mol) in dry CH$_2$Cl$_2$ (250 mL) under N$_2$ was added DMAP (0.8 g, 6.6 mmol)

followed by the addition of TEA (23 mL, 0.17 mol). After 3 hours, the mixture was washed with $H_2O$ (2×100 mL), dried ($MgSO_4$) and concentrated to give 1-O-benzyl-3-O-t-butyldimethylsilyl-rac-glycerol (40) (48.8 g, 100%) as a yellow oil.

$^1$H NMR (360 MHz; $CDCl_3$): δ 0.06 (6 H, s, $Me_2Si$), 0.89 (9 H, s, Bu$^t$Si), 3.48–3.56 (2 H, m, 1-$H_2$ or 3-$H_2$), 3.64 (1 H, dd, J 10 and 5.5 Hz, 1-H or 3-H), 3.68 (1 H, dd, J 10 and 5 Hz, 1-H or 3-H), 3.86 (1 H, quintet, J 5.5 Hz, 2-H), 4.56 (2 H, s, —$OCH_2Ph$) and 7.27–7.35 (5 H, m, -Ph).

Alcohol Compound 40 (48.8 g, 0.16 mmol) was added to a mixture of NaH (4.0 g, 0.17 mol) in dry THF (500 mL). After 5 min, MeI (10 mL, 0.17 mol) was added and, after another 3 hours, the mixture was quenched with $H_2O$ (150 mL), extracted into diethyl ether (500 mL), dried ($MgSO_4$) and concentrated. Purification of the residue by silica-gel column chromatography [eluent: hexane/ethyl acetate, 90/10, v/v] yielded 1-O-benzyl-3-O-t-butyldimethylsilyl-2-O-methyl-rac-glycerol (Compound 41) (37 g, 74%) as a yellow oil.

$^1$H NMR (360 MHz; $CDCl_3$): δ 0.05 and 0.05 (each 3 H, s, $Me_2Si$), 0.88 (9H, s, Bu$^t$Si), 3.42 (1 H, apparent quintet, separation 4.5 Hz, 2-H), 3.47 (3 H, s, OMe), 3.51 (1 H, dd, J 10 and 5.5 Hz, 1-H or 3-H),), 3.61 (1 H, dd, J 10 and 4 Hz, 1-H or 3-H), 3.68 (2 H, d, J 5.5 Hz, 1-H or 3-H), 4.54 (2 H, apparent d, separation 12 Hz, —OCHHAr), 4.58 (2 H, apparent d, separation 12 Hz, —OCHHAr), 7.28 (1 H, m, p-H) and 7.34 (4 H, apparent d, separation 4.5 Hz, o-$H_2$ and m-$H_2$); ESI-MS (m/z, +ve): 333 (MNa$^+$, 100%).

A mixture of the protected glycerol derivative Compound 41 (5.0 g, 16 mmol) and 10% palladium on activated carbon (wet Degussa type E101 NE/W) (0.43 g) in MeOH (50 mL) was evacuated using an aspirator pump and filled with hydrogen. After 2 hours, TLC analysis showed the reaction to be complete, the mixture was filtered through Celite and the filtrate was evaporated to dryness to give 1-O-t-butyldimethylsilyl-2-O-methyl-rac-glycerol (Compound 42) (99%) as a colourless oil.

$^1$H NMR (360 MHz; $CDCl_3$): δ 0.07 (6 H, s, $Me_2Si$), 0.89 (9 H, s, Bu$^t$Si), 3.30–3.36 (1 H, m, 2-H), 3.46 (3 H, s, OMe), 3.63 (1 H, dd, J 11.5 and 5.5 Hz, 1- or 3-H), 3.65 (1 H, dd, J 10.5 and 6.5 Hz, 1- or 3-H), 3.74 (1 H, dd, J 10.5 and 5 Hz, 1- or 3-H) and 3.75 (1 H, dd, J 11.5 and 4 Hz, 1- or 3-H).

To a solution of alcohol Compound 42 (1.1 g, 5.0 mmol) in $CH_2Cl_2$ (10 mL) was added oleoyl chloride (1.8 mL, 5.5 mmol) followed, after 5 min, by the addition of pyridine (0.44 mL, 5.5 mmol). After TLC analysis indicated that the reaction had gone to cmpletion, the mixture was partitioned between ethyl acetate (100 mL) and $H_2O$ (30 mL), the organic extract was dried ($MgSO_4$) and concentrated to give 1-O-t-butyldimethylsilyl-2-O-methyl-3-O-oleoyl-rac-glycerol (Compound 43) (2.4 g, 99%) as a dark brown oil.

$^1$H NMR (360 MHz; $CDCl_3$): δ 0.06 (6 H, s, $Me_2Si$), 0.88 (3 H, t, J 7 Hz, Me), 0.89 (9 H, s, Bu$^t$Si), 1.28 (20 H, apparent br d, separation 11.5 Hz, —$(CH_2)_4$— and —$(CH_2)_6$—), 1.60–1.64 (2 H, m, β-$H_2$), 1.98–2.03 (4 H, m, —$CH_2CH=CHCH_2$—), 2.33 (2 H, t, J 7.5 Hz, α-$H_2$), 3.41–3.46 (1 H, br t, 2-H), 3.45 (3 H, s, OMe), 3.64 (1 H, dd, J 10.5 and 6 Hz, 3-H), 3.68 (1 H, dd, J 10.5 and 5.5 Hz, 3-H), 4.09 (1 H, dd, J 11.5 and 5.5 Hz, 1-H), 4.27 (1 H, dd, J 11.5 and 4 Hz, 1-H) and 5.32–5.36 (2H, m, —$CH_2CH=CHCH_2$—).

1M TBAF (6 mL, 6.0 mmol) was added to a solution of compound Compound 43 (2.4 g, 5.0 mmol) in THF (50 mL). After 30 min, TLC analysis showed that all the starting material had been consumed. Then, the reaction mixture was partitioned between diethyl ether (100 mL) and sat. NaCl solution (30 mL). The organic extract was dried ($MgSO_4$), concentrated and subjected to silica-gel column chromatography [eluent: hexane/ethyl acetate, 75/25, v/v] to give glycerol derivative Compound 44 (1.52 g, 79%) as an oil $^1$H NMR (360 MHz; $CDCl_3$): δ 0.88 (3 H, t, J 7 Hz, Me), 1.28 (20 H, apparent br d, separation 13 Hz, —$(CH_2)_4$— and —$(CH_2)_6$—), 1.60–1.64 (2 H, m, β-$H_2$), 1.98–2.03 (4 H, m, —$CH_2CH=CHCH_2$—), 2.33 (2 H, t, J 7.5 Hz, α-$H_2$), 3.45–3.51 (1H, br t, 2-H), 3.47 (3 H, s, OMe), 3.61 (1 H, dd, J 11.5 and 6 Hz, 3-H), 3.69 (1 H, dd, J 11.5 and 4.5 Hz, 3-H), 4.20 (2 H, apparent d, separation 5 Hz, 1-$H_2$) and 5.29–5.39 (2 H, m, —$CH_2CH=CHCH_2$—).

Dimethyl 3-O-oleoyl-2-O-methyl-rac-glycero-1-phosphate (Compound 45)

To a solution of alcohol Compound 44 (0.79 g, 2.2 mmol) in dry $CH_2Cl_2$ (8 mL) was added N-methylimidazole (0.2 mL, 2.4 mmol) followed by the addition of dimethyl chlorophosphate (0.26 mL, 2.4 mmol). After stirring for 1 hour, the mixture was quenched with sat. $KHSO_4$ (20 mL) and extracted into ethyl acetate (3×50 mL). The combined organic phases were subsequently washed with sat. NaCl (40 mL), dried ($MgSO_4$), concentrated and subjected to silica-gel column chromatography [eluent: ethyl acetate/hexanes, 50/50, v/v] to give protected phosphate Compound 45 as an oil.

$^1$H NMR (360 MHz; $CDCl_3$): δ 0.87 (3 H, t, J 7 Hz, Me), 1.28 (20 H, apparent br d, separation 12.5 Hz, —$(CH_2)_4$— and —$(CH_2)_6$—), 1.60–1.64 (2 H, m, β-$H_2$), 1.98–2.01 (4 H, m, —$CH_2CH=CHCH_2$—), 2.33 (2 H, t, J 7.5 Hz, α-$H_2$), 3.47 (3H, s, OMe), 3.61 (1 H, quintet, J 5 Hz, 2-H), 3.76 (3 H, d, J 2 Hz, OMe), 3.80 (3H, d, J 2 Hz, OMe), 4.05–4.19 (3 H, m, 1-$H_2$ or 3-$H_2$ and 3-H or 1-H), 4.25 (1 H, dd, J 12 and 4.5 Hz, 1-H or 3-H) and 5.29–5.39 (2 H, m, —$CH_2CH=CHCH_2$—); $^{31}$P NMR (146 MHz; $CDCl_3$): δ 2.52; ESI-MS (m/z, +ve): 479 (MH$^+$, 100%) and 496 (M+18$^+$, 83).

3-O-Oleoyl-2-O-methyl-rac-glycero-1-phosphate (Compound 46)

To a solution of dimethyl phosphate Compound 45 (0.10 g, 0.22 mmol) in dry $CH_2Cl_2$ (5 mL) was added BSA (0.16 ml, 0.65 mmol) followed by the addition of TMSBr (60 μL, 1.4 mmol). After 30 min, the reaction was treated with 1/1 MeOH/$H_2O$ (1 mL, v/v) for 30 min after which sat. KHSO4 (5 mL) was added. The mixture was subsequently extracted with ethyl acetate (2×30 mL), the combined organic extracts were dried ($MgSO_4$), concentrated and subjected to Sephadex LH-20 column chromatography [eluent: MeOH/$CH_2Cl_2$, 50/50, v/v] to give the title phosphate (Compound 46) as an oil.

$^1$H NMR (360 MHz; $CDCl_3$): δ 0.86–0.87 (3 H, m, Me), 1.28 (20 H, apparent br d, separation 12 Hz, —$(CH_2)_4$— and —$(CH_2)_6$—), 1.61 (2 H, br s, β-$H_2$), 2.00 (4 H, apparent br d, separation 5 Hz, —$CH_2CH=CHCH_2$—), 2.34 (2 H, t, J 7.5 Hz, α-$H_2$), 3.48 (3 H, s, OMe), 3.66 (1 H, br s, 2-H), 4.15 (3 H, m, 1-$H_2$ or 3-$H_2$ and 3-H or 1-H), 4.27 (1 H, m, 1-H or 3-H), 5.30–5.34 (2 H, m, —$CH_2CH=CHCH_2$—) and 8.41 (1 H, br s, 2×OH); $^{31}$P NMR (146 MHz; $CDCl_3$): δ 1.82; ESI-MS (m/z, -ve): 449 (M–H$^+$,100%) and 463 (MNa$^+$, 37).

Bis-(2-cyanoethyl) 3-O-oleoyl-2-O-methyl-rac-glycero-1-thiophosphate (Compound 47) 2-Cyanoethyl N,N,N',N'-tetraisopropylphosphorodiamidite (0.53 mL, 1.7 mmol) was added under $N_2$ to a solution of 3-hydroxypropionitrile (94 μl, 1.4 mmol) and 1H-tetrazole (0.12 g, 1.7 mmol) in dry $CH_2Cl_2$ (10 mL). After stirring for 1 hour, a subsequent portion of 1H-tetrazole (0.19 g, 2.8 mmol) was added followed by the addition of alcohol Compound 44 (0.51 g, 1.4 mmol). After an additional 30 min, elemental sulfur (1 g) and 1/1 CS$_2$/pyridine (1 mL, v/v) was added. After 2 hours, the reaction mixture was filtered through a short silica-gel plug, concentrated and subjected to silica-gel column chromatography [eluent: ethyl acetate (20–100%) in hexane, v/v] to yield protected thiophosphate Compound 47 (0.29 g, 37%) as a pale yellow oil.

$^1$H NMR (360 MHz; CDCl$_3$): δ 0.88 (3 H, t, J 7 Hz, Me), 1.28 (20 H, apparent br d, separation 13.5 Hz, —(CH$_2$)$_4$— and —(CH$_2$)$_6$—), 1.60–1.64 (2 H, m, β-H$_2$), 1.98–2.01 (4 H, m, —CH$_2$CH=CHCH$_2$—), 2.34 (2 H, t, J 7.5 Hz, α-H$_2$), 2.78 (4H, t, J 6 Hz, 2×NCCH$_2$CH$_2$—), 3.47 (3 H, s, OMe), 4.11–4.48 (8 H, m, 1-H$_2$, 3-H$_2$, and 2×NCCH$_2$CH$_2$—) and 5.29–5.39 (2 H, m, —CH$_2$CH=CHCH$_2$—); $^{31}$P NMR (146 MHz; CDCl$_3$): δ 69.08; ESI-MS (m/z, +ve): 595 (MNa$^+$, 100%).

3-O-Oleoyl-2-O-methyl-rac-glycero-1-thiophosphate (Compound 48)

To a solution of Compound 47 (100 mg, 0.18 mmol) in CH$_3$CN (1.5 mL) under N$_2$ was added TEA (1.5 mL) followed by the addition of BSA (0.11 mL, 0.44 mmol). After 24 hours, the reaction mixture was concentrated and subjected to Sephadex LH-20 column chromatography [eluent: MeOH/CH$_2$Cl$_2$, 50/50, v/v] to give thiophosphate Compound 48 (75 mg, 92%) as a pale yellow oil.

$^1$H NMR (360 MHz; CDCl$_3$): δ 0.87 (3 H, t, J 7 Hz, Me), 1.28 (20 H, apparent br d, separation 12.5 Hz, —(CH$_2$)$_4$— and —(CH$_2$)$_6$—), 1.60–1.61 (2 H, m, β-H$_2$), 2.00–2.01 (4 H, m, —CH$_2$CH=CHCH$_2$—), 2.35 (2 H, t, J 7.5 Hz, α-H$_2$), 3.51 (3H, s, OMe), 3.69 (1 H, br t, 2-H), 4.13–4.31 (4 H, m, 1-H$_2$ and 3-H$_2$), 5.18 (2 H, br s, 2×OH) and 5.29–5.39 (2 H, m, —CH$_2$CH=CHCH$_2$—); $^{31}$P NMR (146 MHz; CDCl$_3$): δ 56.72 ESI-MS (m/z, -ve): 465 (M–H$^+$, 100%); ESI-MS (m/z, +ve): 467 (MH$^+$, 100%).

3-Hydroxypropyl oleoyl amide (Compound 51) To a solution of 3-amino-propan-1-ol (3.1 mL, 40 mmol) in dry THF (150 mL) was added oleoyl chloride (4.4 mL, 13 mmol). After 16 hours, the reaction mixture was diluted with ethyl acetate (100 mL) and washed with sat. NH$_4$Cl (2×100 mL). The organic extract was dried (MgSO$_4$), concentrated and subjected to silica-gel column chromatography [eluent: ethyl acetate (25–100%) in hexane, v/v] to give amide Compound 51 (4.4 g, 95%) as a white solid.

$^1$H NMR (360 MHz; CDCl$_3$): δ 0.88 (3 H, t, J 7 Hz, Me), 1.27 (20 H, apparent br d, separation 12.5 Hz, —(CH$_2$)$_4$— and —(CH$_2$)$_6$—), 1.60–1.69 (4 H, m, 2-H$_2$ and β-H$_2$), 1.99–2.00 (4 H, m, —CH$_2$CH=CHCH$_2$—), 2.19 (2 H, t, J 7.5 Hz, α-H$_2$), 3.41 (2 H, quartet, J 6 Hz, 1-H$_2$), 3.61 (2 H, t, J 5.5 Hz, 3-H$_2$), 5.29–5.38 (2 H, m, —CH$_2$CH=CHCH$_2$—) and 5.90 (1 H, br s, N—H); ESI-MS (m/z, +ve): 340 (MH$^+$, 100%).

Dibenzyl 3-amino-3-N-oleoyl-propyl phosphate (Compound 52) To a mixture of Compound 51 (0.34 g, 1.0 mmol) and 1H-tetrazole (0.14 g, 2.0 mmol) in dry CH$_2$Cl$_2$ (5 mL) under N$_2$ was added dibenzyl N,N-diisopropylphosphoramidite (1.1 mL, 3.0 mmol). After 45 min t-BuOOH (2 mL) was added and the mixture was stirred for a subsequent 35 min after which the mixture was concentrated and subjected to silica-gel column chromatography [eluent: ethyl acetate in hexane, 50/50, v/v] to give dibenzyl phosphate Compound 38 (0.27 g, 44%) as an oil.

$^1$H NMR (360 MHz; CDCl$_3$): δ 0.87 (3 H, t, J 7 Hz, Me), 1.28 (20 H, br s, —(CH$_2$)$_4$— and —(CH$_2$)$_6$—), 1.57 (2 H, br s, β-H$_2$), 1.77–1.82 (2 H, m, 2-H$_2$), 1.98–2.00 (4 H, m, —CH$_2$CH=CHCH$_2$—), 2.11 (2 H, t, J 8 Hz, α-H$_2$), 3.29 (2 H, quartet, J 6 Hz, 1-H$_2$), 4.10–4.15 (2 H, t, J 5.5 Hz, 3-H$_2$), 4.99–5.09 (4 H, m, —OCH$_2$Ph), 5.28–5.38 (2 H, m, —CH$_2$CH=CHCH$_2$—), 6.25 (1 H, br s, N—H) and 7.35 (10H, br s, 2×-Ph); $^{31}$P NMR (146 MHz; CDCl$_3$): δ 0.78 ESI-MS (m/z, +ve): 600 (MH$^+$, 100%).

Dimethyl 3-amino-3-N-oleoyl-propyl phosphate (Compound 53) To a mixture of amide Compound 51 (0.30 g, 0.9 mmol) and dimethyl chlorophosphate (0.14 mL, 1.3 mmol) in dry CH$_2$Cl$_2$ (5 mL) under N$_2$ was added N-methylimidazole (0.14 mL, 1.8 mmol). After 40 hours, TLC analysis showed the reaction to be complete and the mixture was partitioned between ethyl acetate (20 mL) and sat. NaCl (4 mL). The organic phase was dried (MgSO$_4$), concentrated and subjected to silica-gel column chromatography [eluent: 5% MeOH in CH$_2$Cl$_2$, v/v] to give dimethyl phosphate Compound 53 (0.35 g, 87%) as a pale yellow oil.

$^1$H NMR (360 MHz; CDCl$_3$): δ 0.87 (3 H, t, J 7 Hz, Me), 1.28 (20 H, apparent br d, separation 11.5 Hz, —(CH$_2$)$_4$— and —(CH$_2$)$_6$—), 1.61–1.78 (2 H, m, β-H$_2$), 1.88 (2 H, quintet, J 6 Hz, 2-H$_2$), 1.99–2.01 (4 H, m, —CH$_2$CH=CHCH$_2$—), 2.16 (2 H, t, J 8 Hz, α-H$_2$), 3.38 (2 H, quartet, J 6 Hz, 3-H$_2$), 3.76 and 3.79 (each 3 H, s, 2×OMe), 4.10–4.15 (2 H, t, J 5.5 Hz, 1-H$_2$), 5.33–5.35 (2 H, m, —CH$_2$CH=CHCH$_2$—) and 6.25 (1 H, br s, N—H); $^{31}$P NMR (146 MHz; CDCl$_3$): δ 3.19; ESI-MS (m/z, +ve): 340 (MNa$^+$, 32%) and (M+83, 100).

1-O-Palmitoyl-rac-glycidol (Compound 57) To a solution of glycidol (0.45 mL, 6.7 mmol) in dry CH$_2$Cl$_2$ (50 ml) under N$_2$ at −78° C. was added palmitoyl chloride (2.0 mL, 7.3 mmol). After 5 min, pyridine (1.4 mL, 16.8 mmol) was added and the reaction mixture was allowed to stir for 1 hour at −78° C. before being allowed to warm to room temperature over a 1.5 hours period. Then, the mixture was diluted with CH$_2$Cl$_2$ (100 mL), washed with sat. KHSO$_4$ (10 mL), sat. NaHCO$_3$ (10 mL) and sat. NaCl (20 mL), dried (MgSO$_4$) and concentrated to give an oil. The residue was subjected to silica-gel column chromatography [eluent: ethyl acetate/hexane, 10/90, v/v] to give epoxide Compound 57 (1.3 g, 63%) as a colourless oil.

$^1$H NMR (360 MHz; CDCl$_3$): δ 0.88 (3 H, t, J 7 Hz, Me), 1.25 (24H, br s, 12×CH$_2$), 1.63 (2 H, quintet, J 7.5 Hz, β-H$_2$), 2.35 (2 H, t, J 7.5 Hz, α-H$_2$), 2.65 (1 H, dd, J 5 and 2.5 Hz, 3-H), 2.85 (1 H, t, J 4.5 Hz, 3-H), 3.19–3.23 (1 H, m, 2-H), 3.91 (1 H, dd, J 12.5 and 6.5 Hz, 1-H) and 4.42 (1 H, dd, J 12.5 and 3 Hz, 1-H); ESI-MS (m/z, +ve): 335 (MNa$^+$, 100%).

1-O-Palmitoleoyl-rac-glycidol (Compound 58)

To a solution of glycidol (0.04 mL, 0.8 mmol) in dry CH$_2$Cl$_2$ (10 ml) under N$_2$ at −78° C. was added palmitoleoyl chloride (0.20 g, 0.7 mmol). After 5 min, pyridine (0.15 mL, 1.8 mmol) was added and the reaction mixture was allowed to stir for 1 hour at −78° C. before being allowed to warm to room temperature over a 1.5 hours period. Next, the reaction mixture was diluted with CH$_2$Cl$_2$ (50 mL), washed with sat. KHSO$_4$ (5 mL), sat. NaHCO$_3$ (5 mL) and sat. NaCl (10 mL), dried (MgSO$_4$) and concentrated to give an oil. The residue was purified by silica-gel column chromatography [eluent: ethyl acetate/hexane, 10/90, v/v] to furnish epoxide Compound 58 as a colourless oil.

$^1$H NMR (360 MHz; CDCl$_3$): δ 0.88 (3 H, t, J 6.5 Hz, Me), 1.30 (16H, br s, —(CH$_2$)$_4$— and —(CH$_2$)$_4$—), 1.61–1.65 (2 H, m, β-H$_2$), 2.00–2.01 (4 H, m, —CH$_2$CH=CHCH$_2$—), 2.35 (2 H, t, J 7.5 Hz, α-H$_2$), 2.65 (1 H, dd, J 4.5 and 2.5 Hz, 3-H), 2.85 (1 H, t, J 4.5 Hz, 3-H), 3.20–3.22 (1 H, m, 2-H), 3.91(1 H, dd, J 12.5 and 6.5 Hz, 1-H), 4.41 (1 H, dd, J 12.5 and 2.5 Hz, 1-H) and 5.29–5.39 (2 H, m, —CH$_2$CH=CHCH$_2$—); ESI-MS (m/z, +ve): 311 (MH$^+$, 30%), 333 (MNa$^+$, 100%).

Dimethyl 2-amino-2-N-oleoyl-ethyl phosphate (Compound 59)

To a mixture of amide Compound 51 (1.0 g, 3.1 mmol) and dimethyl chlorophosphate (0.50 mL, 4.6 mmol) in dry CH$_2$Cl$_2$ (100 mL) under N$_2$ was added N-methylimidazole (0.73 mL, 9.2 mmol). After 40 hours, TLC analysis showed the reaction to be complete and the mixture was washed with sat. NaHCO$_3$ (3×20 mL), dried (MgSO$_4$) and evaporated to dryness to give dimethyl phosphate Compound 59 (1.2 g, 89%) as a pale yellow oil.

$^1$H NMR (360 MHz; CDCl$_3$): δ 0.75 (3 H, t, J 6.5 Hz, Me), 1.16 (20 H, apparent br d, separation 11.5 Hz, —(CH$_2$)$_4$— and —(CH$_2$)$_6$—), 1.50 (2 H, br s, β-H$_2$), 1.88 (4 H, apparent br d, separation 5.5 Hz, —CH$_2$CH=CHCH$_2$—), 2.08 (2 H, t, J 7.5 Hz, α-H$_2$), 3.34–3.38 (2 H, m, 2-H$_2$), 3.64 and 3.67 (each 3 H, s, 2×OMe), 3.97–4.02 (2 H, m, 1-H$_2$), 5.16–5.26 (2 H, m, —CH$_2$CH=CHCH$_2$—) and 6.79 (1 H, br s, N—H); $^{31}$P NMR(146 Mhz; CDCl$_3$): δ 2.49; ESI-MS (m/z, +ve): 434 (MH$^+$, 100%).

Di-tert.-butyl 2-amino-2-N-oleoyl-propyl phosphate (Compound 60)

To a mixture of Compound 51 (1.0 g, 2.9 mmol) and 1H-tetrazole (0.41 g, 5.9 mmol) in dry CH$_2$Cl$_2$ (10 mL) under N$_2$ was added di-tert.-butyl N,N-diisopropylphosphoramidite (1.2 g, 4.4 mmol). After 1.5 hours, t-BuOOH (2 mL) was added and the mixture was stirred for a another 30 min. Next, the mixture was concentrated and subjected to silica-gel column chromatography [eluent: ethyl acetate in hexane, 25/75, v/v] to give di-tert.-butyl phosphate Compound 60 (1.3 g, 81%) as an oil.

$^1$H NMR (360 MHz; CDCl$_3$): δ 0.87 (3 H, t, J 7 Hz, Me), 1.27 (20 H, apparent br d, separation 10 Hz, —(CH$_2$)$_4$— and —(CH$_2$)$_6$—), 1.49 (18H, s, 2×Bu$^t$O), 1.59–1.66 (2 H, m, β-H$_2$), 1.83 (2 H, quintet, J 6 Hz, 2-H$_2$), 1.97–2.00 (4 H, m, —CH$_2$CH=CHCH$_2$—), 2.16 (2 H, t, J 7.5 Hz, α-H$_2$), 3.39 (2 H, quintet, J 6 Hz, 3-H$_2$), 4.03 (2 H, dt, J 7.5 and 6 Hz, 1-H$_2$), 5.32–5.35 (2 H, m, —CH$_2$CH=CHCH$_2$—) and 6.47 (1 H, m, N—H); $^{31}$P NMR (146 MHz; CDCl$_3$): δ −7.47; ESI-MS (m/z, +ve): 420 (M−2Bu$^t$+3H$^+$, 78%), 476 (M−Bu$^t$+2H$^+$, 30), 532 (MH$^+$, 100).

2-Amino-2-N-oleoyl-propyl phosphate (Compound 61) A solution of the protected phosphate Compound 60 (250 mg, 0.47 mmol) was treated with ¼ TFA/CH$_2$Cl$_2$ (15 mL, v/v) for 3 hours. Next, the reaction mixture was concentrated and the residue was purified by Sephadex LH-20 column chromatography [eluent: MeOH/CH$_2$Cl$_2$, 50/50, v/v] to give phosphate Compound 61 (130 mg, 67%) as a white solid.

$^1$H NMR (360 MHz; CDCl$_3$): δ 0.81 (3 H, t, J 6.7 Hz, Me), 1.20 (20 H, apparent br d, —(CH$_2$)$_4$— and —(CH$_2$)$_6$—), 1.51 (2 H, br s, β-H$_2$), 1.79 (2 H, br s, 2-H$_2$), 1.9 (4 H, m, —CH$_2$CH=CHCH$_2$—), 2.16 (2 H, br s, α-H$_2$), 3.3 (2 H, br s, 2-H$_2$), 3.9 (2 H, m, 1-H$_2$), 5.25 (2 H, m, —CH$_2$CH=CHCH$_2$—) and 7.2 (1 H, br s, N—H); $^{31}$P NMR (146 Mhz; CDCl$_3$): δ 1.10; ESI-MS (m/z, −ve): 418 (M−H$^+$, 100%); ESI-MS (m/z, +ve): 420 (MH$^+$, 100%).

1-O-Oleyl-2-O-methyl glycerol (Compound 64)

2-O-Methyl glycerol (1.54 g, 14.5 mmol) was added to a suspension of NaH (0.38 g, 15.9 mmol) in dry DMF (20 mL) under N$_2$. After 2 min, oleyl bromide (2.4 g, 7.2 mmol) was added and stirring was continued for 0.5 hour. Then, the reaction mixture was quenched with water (20 mL) and extracted with diethyl ether (150 mL). The combined organic phases were dried (MgSO$_4$) and concentrated to give an oil which was subjected to silica-gel column chromatography [eluent: EtOAc/Hexane, 50/50, v/v] to give alcohol Compound 64 (1.3 g, 50%).

$^1$H NMR (360 MHz; CDCl$_3$): δ 0.88–0.89 (3 H, m, Me), 1.29 (22 H, br s, —(CH$_2$)$_5$— and —(CH$_2$)$_6$—), 1.59 (2 H, br s, β-H$_2$), 2.01 (4 H, br s, —CH$_2$CH=CHCH$_2$—), 3.44–3.76 (7H, m, 3-H$_2$, 1-H$_2$, 2-H and α-H$_2$), 3.47 (3 H, s, OMe), and 5.34 (2 H, m, —CH$_2$CH=CHCH$_2$—); ESI-MS (m/z, +ve): 357 (MH$^+$, 100%), 379 (MNa$^+$, 53).

Bis-(2-cyanoethyl) 3-O-oleyl-2-O-methyl-rac-glycero-1-thiophosphate (Compound 65)

To a solution of 3-hydroxypropionitrile (0.16 mL, 2.4 mmol) and 1H-tetrazole (0.18 g, 2.5 mmol) in dry CH$_2$Cl$_2$ (8 mL) under N$_2$ was added 2-cyanoethyl N,N,N',N'-tetraisopropylphosphorodiamidite (0.71 mL, 2.2 mmol). After stirring for 1 hour, a second portion of 1H-tetrazole (0.20 g, 2.8 mmol) was added followed by the addition of alcohol Compound 64 (0.50 g, 1.4 mmol). After an additional 30 min, elemental sulfur (0.5 g) and 1/1 CS$_2$/pyridine (0.5 mL, v/v) were added. After 14 hours, the reaction mixture was filtered through a plug of silica-gel, concentrated and purified by silica-gel column chromatography [eluent: EtOAc/hexane, 25/75 v/v] to yield protected thiophosphate Compound 65 (0.33 g, 42%) as a pale yellow oil.

$^1$H NMR (360 MHz; CDCl$_3$): δ 0.88 (3 H, t, J 7 Hz, Me), 1.28 (22 H, m, —(CH$_2$)$_4$— and —(CH$_2$)$_6$—), 1.54–1.58 (2 H, m, β-H$_2$), 1.98–2.03 (4 H, m, —CH$_2$CH=CHCH$_2$—), 2.78 (4 H, t, J 6 Hz, 2×NCCH$_2$CH$_2$—), 3.44 (2 H, t, J 7 Hz, α-H$_2$), 3.46 (3 H, s, OMe), 3.49–3.51 (2 H, m, 3-H$_2$), 3.53–3.58 (1 H, m, 2-H), 4.15 (1 H, dd, J 15 and 5 Hz, 1-H), 4.23–4.36 (5 H, m, 2×NCCH$_2$CH$_2$— and 1-H) and 5.30–5.39 (2 H, m, —CH$_2$CH=CHCH$_2$—); $^{31}$P NMR (146 MHz; CDCl$_3$): δ 69.04; ESI-MS (m/z, +ve): 581 (MNa$^+$, 100%); ESI-MS (m/z, −ve): 504 (M−NCCH$_2$CH$_2$, 100%).

3-O-Oleyl-2-O-methyl-rac-glycero-1-thiophosphate (Compound 66)

To a solution of compound Compound 65 (50 mg, 87 μmol) in CH$_3$CN (0.5 mL) under N$_2$ at 30° C. was added TEA (0.5 mL) followed by the addition of BSA (54 μL, 0.22 mmol). After 24 hours, the reaction mixture was concentrated and subjected to Sephadex LH-20 column chromatography [eluent: MeOH/CH$_2$Cl$_2$, 50/50, v/v] to give a mixture of thiophosphate Compound 66 and monodeprotected Compound 65 (80 mg) in a 3/2 ratio.

$^{31}$P NMR (146 MHz; CDCl$_3$): δ 59.24, 56.74 (ratio 3/2, respectively); ESI-MS (m/z, −ve): 451 (M−H$^+$, 80%) and 504 (M+NCCH$_2$CH$_{2-2}$H$^+$, 100).

Bis-(2-cyanoethyl) 1-(3-propyl oleoate) thiophosphate (Compound 67)

To a solution of 3-hydroxypropionitrile (0.16 mL, 2.4 mmol) and 1H-tetrazole (0.19 g, 2.6 mmol) in dry CH$_2$Cl$_2$ (7 mL) under N$_2$ was added 2-cyanoethyl N,N,N',N'-tetraisopropylphosphorodiamidite (0.65 mL, 2.1 mmol). After stirring for 1 hour, a second portion of 1H-tetrazole (0.21 g, 2.9 mmol) was added followed by the addition of alcohol Compound 28 (0.50 g, 1.5 mmol). After an additional 30 min, elemental sulfur (0.5 g) and 1/1 CS$_2$/pyridine (1 mL, v/v) were added. After 14 hours, the reaction mixture was filtered through a plug of silica-gel, concentrated and purified by silica-gel column chromatography [eluent: EtOAc/hexane, 25/75 v/v] to yield protected thiophosphate Compound 67 (0.27 g, 34%) as a pale yellow oil.

¹H NMR (360 MHz; CDCl₃): δ 0.88 (3 H, t, J 6.5 Hz, Me), 1.28 (20 H, apparent br d, separation 13.5 Hz, —(CH₂)₄— and —(CH₂)₆—), 1.61 (2 H, br s, β-H₂), 2.02–2.05 (6 H, m, 2-H₂ and —CH₂CH=CHCH₂—), 2.31 (2 H, t, J 7.5 Hz, α-H₂), 2.78 (4 H, t, J 6 Hz, 2×NCCH₂CH₂—), 4.17–4.24 (4 H, m, 1-H₂ and 3-H₂ or 2×NCCH₂CH₂—), 4.17–4.24 (4 H, m, 1-H₂ and 3-H₂ or 2×NCCH₂CH₂—), and 5.34 (2 H, br s, —CH₂CH=CHCH₂—); ³¹P NMR (146 MHz; CDCl₃): δ 68.19; ESI-MS (m/z, +ve): 543 (MH⁺, 77%) and 565 (MNa⁺, 100).

1-(3-propyl oleate) thiophosphate (Compound 68) To a solution of Compound 67 (220 mg, 0.41 mmol) in CH₃CN (2 mL) under N₂ was added TEA (2 mL) followed by the addition of BSA (0.25 mL, 1.01 mmol). After 66 hours, the reaction mixture was concentrated and subjected to Sephadex LH-20 column chromatography [eluent: MeOH/CH₂Cl₂, 50/50, v/v] to give thiophosphate Compound 68 (144 mg, 69%) as a pale yellow oil.

¹H NMR (360 MHz; CDCl₃): δ 0.85 (3 H, t, J 7 Hz, Me), 1.25 (20 H, apparent br d, separation 11.5 Hz, —(CH₂)₄— and —(CH₂)₆—), 1.58 (2 H, br s, β-H₂), 1.97–2.02 (6 H, m, 2-H₂ and —CH₂CH=CHCH₂—), 2.30 (2 H, t, J 7.5 Hz, α-H₂), 4.11–4.17 (2 H, m, 1-H₂ or 3-H₂), 4.21 (2 H, t, J 6 Hz, 1-H₂ or 3-H₂), 5.31 (2 H, br s, —CH₂CH=CHCH₂—) and 7.26 (2 H, br s, 2×OH); ³¹P NMR (146 MHz; CDCl₃): δ 48.60 ESI-MS (m/z, -ve): 465 (M-H⁺, 100%); ESI-MS (m/z, +ve): 323 (100%) and 437 (MH⁺, 95).

Di-tert.-butyl 3-O-oleyl-2-O-methyl-rac-glycero-1-thiophosphate (Compound 69)

To a mixture of Compound 64 (0.3 g, 0.84 mmol) and 1H-tetrazole (0.12 g, 1.7 mmol) in dry CH₂Cl₂ (5 mL) under N₂ was added di-tert.-butyl N,N-diisopropylphosphoramidite (0.34 mL, 1.1 mmol). After 2 hours, elemenatal sulfur (0.5 g) and 1/1 CS₂/pyridine (1.0 mL, v/v) were added and the mixture was stirred for a another 2 hours after. Then, the mixture was filtered through a plug of silica-gel, concentrated and subjected to silica-gel column chromatography [eluent: ethyl acetate in hexane, 1/15, v/v] to give di-tert.-butyl thiophosphate Compound 69 (0.48 g, quant.) as an oil.

¹H NMR (360 MHz; CDCl₃): δ 0.87 (3 H, t, J 7 Hz, Me), 1.26–1.30 (22 H, m, —(CH₂)₄— and —(CH₂)₆—), 1.53 (20 H, m, 2×Buᵗ O and β-H₂), 1.97–2.01 (4 H, m, —CH₂CH=CHCH₂—), 3.43 (2 H, t, J 7 Hz, α-H₂), 3.46 (3 H, s, OMe), 3.48–3.57 (3H, m, 3-H₂ and 2-H), 4.01–4.14 (2 H, m, 1-H₂) and 5.34 (2 H, apparent t, separation 5 Hz, —CH₂CH=CHCH₂—); ³¹P NMR (146 MHz; CDCl₃): δ 52.39; ESI-MS (m/z, -ve): 507 (M-Buᵗ, 100%); ESI-MS (m/z, +ve): 589 (MNa⁺, 100%).

Dimethyl Erucyl Phosphate (Compound 70))

To a solution of erucyl alcohol (0.50 g, 1.5 mmol) in dry CH₂Cl₂ (10 mL) was added N-methylimidazole (0.14 mL, 1.7 mmol) followed by the addition of dimethyl chlorophosphate (0.20 mL, 1.9 mmol). After 20 hours, the reaction mixture was concentrated and subjected to silica-gel column chromatography [eluent: hexane/ethyl acetate, 66/33, v/v] to give dimethyl phosphate Compound 70 (0.59 g, 89%) as an oil.

¹H NMR (360 MHz; CDCl₃): δ 0.88 (3 H, t, J 7 Hz, Me), 1.26 (30H, br s, —(CH₂)₉— and —(CH₂)₆—), 1.68 (2 H, quintet, J 7 Hz β-H2), 2.01 (4 H, apparent br d, separation 5 Hz, —CH₂CH=CHCH₂—), 3.75 and 3.78 (each 3 H, s, 2×OMe), 4.04 (2 H, quartet, J 7 Hz, α-H₂), and 5.30–5.39 (2 H, m, —CH₂CH=CHCH₂—); ³¹P NMR(146 Mhz; CDCl₃): δ 2.65; ESI-MS (m/z, +ve): 433 (MH⁺, 100).

Erucyl Phosphate (Compound 71)

To a solution of protected phosphate Compound 70 (150 mg, 0.35 mmol) in dry CH₂Cl₂ (6 mL) was added BSA (0.19 mL, 0.76 mmol) followed by the addition of TMSBr (0.10 mL, 0.76 mmol). After 30 min, TLC analysis showed complete consumption of the starting material and the reaction was quenched with 1/1 MeOH/H₂O (2 mL, v/v) for 15 min, followed by the addition of sat. KHSO₄ (5 mL). Subsequently, the reaction mixture was extracted with ethyl acetate (2×30 mL), the organic extracts were combined, dried (MgSO₄) and concentrated to give an oil which was subjected to Sephadex LH-20 column chromatography [eluent: MeOH/CH₂Cl₂, 50/50, v/v] to give phosphate Compound 71 (90 mg, 64%) as an oil.

¹H NMR (360 MHz; CDCl₃): δ 0.88 (3 H, t, J 7 Hz, Me), 1.26 (30H, br s, —(CH₂)₉— and —(CH₂)₆—), 1.66 (2 H, quintet, J 6.5 Hz β-H₂), 1.98–2.03 (4 H, m, —CH₂CH=CHCH₂—), 3.94–4.00 (2 H, m, α-H₂), 5.30–5.39 (2 H, m, —CH₂CH=CHCH₂—) and 7.32 (2 H, br s, 2×OH); ³¹P NMR(146 Mhz; CDCl₃): δ 2.59; ESI-MS (m/z, -ve): 403 (M-H⁺, 100).

Oleyl 2-O-methyl-rac-glycerate (Compound 76)

To a solution of oxalyl chloride (87 μL, 1.0 mmol) in CH₂Cl₂ (7 mL) at -78° C. was added DMSO (71 μL, 1.0 mmol). After 20 min, alcohol Compound 42 (0.20 g, 0.91 mmol) was added followed, after another 20 min, by the addition of triethylamine (0.63 mL, 4.6 mmol). The reaction was warmed to room temperature over a 10 min period, filtered through a plug of silica-gel, which was washed with ethyl acetate (50 mL) and concentrated to give 3-O-t-butyldimethylsilyl-2-O-methyl-rac-glyceraldehyde Compound 73 (0.20 g, 100%) as a colourless oil.

¹H NMR (360 MHz; CDCl₃): δ 0.07 (6 H, s, Me₂Si), 0.88 (9 H, s, Buᵗ Si), 3.51 (3 H, s, OMe), 3.67–3.68 (1 H, m, 2-H), 3.92 (2 H, br d, J 6.5 Hz, 3-H₂), 9.72 (1 H, s, CHO).

To a vigorously stirring mixture of CH₂Cl₂ (20 mL), water (20 mL) and aldehyde Compound 73 (0.93 g, 4.3 mmol) at 0° C. was added sulfamic acid (0.63 g, 6.8 mmol) and 2-methyl-2-butene (0.60 g, 8.5 mmol). After 5 min, sodium chlorite (0.77 g, 8.5 mmol) was added and the reaction was monitored by TLC until no starting material remained. The reaction mixture was extracted with CH₂Cl₂ (2×20 mL), and the combined organic layers were washed with sat. NaCl (2×20 μL), dried (MgSO₄) and concentrated to give a colourless oil. The oil was redissolved in CH₂Cl₂ (50 mL) after which sat. NaHCO₃ (10 mL) was added. The aqueous phase was isolated, CH₂Cl₂ (50 mL) was added and the mixture was acidified by adding 10% aqueous acetic acid (v/v). The organic phase was dried (MgSO₄) and concentrated to give 3-O-t-butyldimethylsilyl-2-O-methyl-rac-glyceric acid Compound 74 (0.39 g, 38%) as a colourless oil.

¹H NMR (360 MHz; CDCl₃): δ 0.07 and 0.07 (each 3 H, s, Me₂Si), 0.88 (9H, s, Buᵗ Si), 3.52 (3 H, s, OMe) and 3.87–3.99 (3 H, m, 2-H and 3-H₂).

To a mixture of oleyl alcohol (0.52 mL, 1.6 mmol), DIC (0.27 mL, 1.7 mmol) and glyceric acid Compound 74 (0.39 g, 1.6 mmol) in DMF (10 mL) was added DMAP (~20 mg). After 16 hours, the solvent was removed in vacuo and the residue was partitioned between EtOAc (50 mL) and water (10 mL). The organic phase was dried (MgSO₄) and concentrated to give an oil which was purified by silica-gel column chromatography [eluent: EtOAc/Hexane, 10/90, v/v] to give oleyl 3-O-t-butyldimethylsilyl-2-O-methyl-rac-glycerate Compound 75 (0.33 g, 41%) as a colourless oil.

¹H NMR (360 MHz; CDCl₃): δ 0.05 (6 H, s, Me₂Si), 0.86–0.89 (12H, m, Buᵗ Si and Me), 1.28 (22 H, apparent br d, separation 10.5 Hz, —(CH₂)₅— and —(CH₂)₆—), 1.61–1.67 (2 H, m, β-H$_2$), 1.98–2.04 (4 H, m, —CH$_2$CH=CHCH$_2$—), 3.44 (3 H, s, OMe), 3.83–3.90 (3 H, m, 1-H and 2-H$_2$), 4.15 (2 H, t, J 7 Hz, α-H$_2$), and 5.33–5.39 (2 H, m, —CH$_2$CH=CHCH$_2$—).

1M TBAF (0.7 mL, 0.7 mmol) was added to a solution of Compound 75 in THF (8 mL). After 40 min, TLC analysis showed that all the starting material had been consumed. Then, the reaction mixture was partitioned between diethyl ether (100 mL) and sat. NaCl solution (15 mL). The organic extract was dried (MgSO$_4$) and concentrated to give a yellow oil which was subjected to silica-gel column chromatography [eluent: hexane/ethyl acetate, 80/20, v/v] to give the title ester (Compound 76) (0.18 g, 71%).

$^1$H NMR (360 MHz; CDCl$_3$): δ 0.87 (3 H, t, J 7 Hz, Me), 1.28 (22 H, apparent br d, separation 11 Hz, —(CH$_2$)$_5$— and —(CH$_2$)$_6$—), 1.65 (2 H, quintet, J 7 Hz, β-H$_2$), 2.01 (4 H, quintet, J 6.5 Hz, —CH$_2$CH=CHCH$_2$—), 2.24 (1 H, m, OH), 3.49 (3 H, s, OMe), 3.75–3.81 (1 H, m, 2-H$_2$),3.89 (2 H, quintet, J 3.5 Hz, 3-H$_2$ or α-H$_2$), 4.11–4.22 (2 H, m, 3-H$_2$ or α-H$_2$) and 5.29–5.40 (2 H, m, —CH$_2$CH=CHCH$_2$—); ESI-MS (m/z, +ve): 393 (MNa$^+$, 100), 763 (2MNa$^+$, 20).

Oleyl 1-(bis-(2-cyanoethyl) thiophosphoryl)-2-O-methyl-rac-glycerate (Compound 77)

To a solution of 3-hydroxypropionitrile (55 μL, 0.80 mmol) and 1H-tetrazole (60 mg, 0.85 mmol) in dry CH$_2$Cl$_2$ (4 mL) under N$_2$ was added 2-cyanoethyl N,N,N',N'-tetraisopropylphosphorodiamidite (0.24 mL, 0.76 mmol). After stirring for 1 hour, a second portion of 1H-tetrazole (66 mg, 0.94 mmol) was added followed by the addition of ester Compound 76 (175 mg, 0.47 mmol). After 1 hour, elemental sulfur (0.25 g) and 1/1 CS$_2$/pyridine (0.5 mL. v/v) were added. After an additional 2 hours, the reaction mixture was filtered through a plug of silica-gel, concentrated and purified by silica-gel column chromatography [eluent: EtOAc/hexane, 25/75 v/v] to yield protected thiophosphate 77 (78 mg, 29%) as a pale yellow oil and recovered ester Compound 76 (73 mg, 42%).

$^1$H NMR (360 MHz; CDCl$_3$): δ 0.86 (3 H, t, J 7 Hz, Me), 1.27 (22 H, apparent br d, separation 12.5 Hz, —(CH$_2$)$_4$— and —(CH$_2$)$_6$—), 1.65 (2 H, quintet, β-H$_2$), 1.98–2.02 (4 H, m, —CH$_2$CH=CHCH$_2$—), 2.76 and 2.78 (each 2 H, t, J 6.5 Hz, 2×NCCH$_2$CH$_2$—), 3.48 (3 H, s, OMe), 3.99 (1 H, t, J 4.2 Hz, 2-H), 4.17 (2 H, t, J 7 Hz, α-H$_2$), 4.22–4.47 (6 H, m, 3-H$_2$ and 2×NCCH$_2$CH$_2$—) and 5.28–5.37 (2 H, m, —CH$_2$CH=CHCH$_2$—); $^{31}$P NMR (146 MHz; CDCl$_3$): δ 69.04; ESI-MS (m/z, +ve): 573 (M-H$^+$, 25%), 595 (MNa$^+$, 100).

Oleyl 1-thiophosphoryl-2-O-methyl-rac-glycerate (Compound 78)

To a solution of Compound 77 (100 mg, 0.18 mmol) in CH$_3$CN (0.5 mL) under N$_2$ at 30° C. was added TEA (0.5 mL) followed by the addition of BSA (0.11 mL, 0.45 mmol). After 24 hours, the reaction mixture was concentrated and subjected to Sephadex LH-20 column chromatography [eluent: MeOH/CH$_2$Cl$_2$, 50/50, v/v] to give thiophosphate Compound 78 (40 mg, quant.) as a pale yellow oil.

$^1$H NMR (360 MHz; CDCl$_3$): δ 0.87 (3 H, t, J 7 Hz, Me), 1.24–1.35 (22 H, m, —(CH$_2$)$_4$— and —(CH$_2$)$_6$—), 1.65 (2 H, quintet, β-H$_2$), 1.98–2.03 (4 H, m, —CH$_2$CH=CHCH$_2$—), 3.47 (3 H, s, OMe), 4.09 (1 H, dd, J 5 and 3.5 Hz, 2-H), 4.09–4.38 (4 H, m, 1-H$_2$ and α-H$_2$), 5.32–5.38 (2 H, m, —CH$_2$CH=CHCH$_2$—), 5.51 (2 H, br s, 2×OH); $^{31}$P NMR (146 MHz; CDCl$_3$): δ 55.28; ESI-MS (m/z, -ve): 465 (M-H$^+$, 100%).

3-O-Oleoyl-2-O-methyl-rac-glycero-1-sulfate (Compound 81)

To a solution of alcohol Compound 44 (0.30 g, 0.8 mmol) in DMF (10 mL) was added triethylamine sulfur trioxide complex (0.74 g, 4.1 mmol) and the mixture was stirred for 5.5 h at 40° C. Next, NaHCO$_3$ (0.3 g, 3.6 mmol) was added and, after stirring for another 30 min, the mixture was filtered through a glass sinter. The filtrate was concentrated to give a light brown oil which was subjected to Sephadex LH-20 column chromatography [eluent: MeOH/CH$_2$Cl$_2$, 50/50, v/v] to furnish, after extensive drying in vacuo, sulfate Compound 81 (0.52 g) as its triethylamine salt.

$^1$H NMR (360 MHz; CDCl$_3$): δ 0.87 (3 H, t, J 7 Hz, Me), 1.27 (20 H, apparent br d, separation J 11 Hz, —(CH$_2$)$_4$— and —(CH$_2$)$_6$—), 1.46 (15H, t, (CH$_3$CH$_2$)$_3$N, J 7 Hz), 1.59 (2 H, m, β-H$_2$), 1.97–2.02 (4 H, m, —CH$_2$CH=CHCH$_2$—), 2.31 (2 H, t, J 7.6 Hz, α-H$_2$), 3.21–3.13 (10H, m, (CH$_3$CH$_2$)$_3$N), 3.45 (3 H, s, OMe), 3.69–3.74 (1 H, m, 2-H), 4.06–4.29 (4 H, m, 1-H$_2$ and 3-H$_2$) and 5.28–5.37 (2 H, m, —CH$_2$CH=CHCH$_2$—); $^{31}$P NMR (146 MHz; CDCl$_3$): δ 63.69 (m); ESI-MS (m/z, +ve): 656 (MH$^+$+2TEA, 100%); ESI-MS (m/z, -ve): 449 (M-H$^+$, 100%).

EXAMPLE 2

Anti-apoptotic Activity Assay

In order to determine the apoptotic activity of the claimed invention, the following method of analysis was used. The-cell assay is described in detail in U.S. Pat. Nos. 5,637,486, 5,620,888, and 5,681,703, and Tomei et al. (1993) *Proc Natl. Acad. Sci.* 90:853–857. Briefly, mouse fibroblast C3H/10T½ cells (clone 8) were obtained from ATCC (Rockville, Md.) and were maintained in exponential growth phase in which the cell cycle is randomly distributed and no cells are arrested in G$_0$, and in quiescence. Exponential growth phase was assured by seeding at 2000 cells per 1 ml (5 ml for a 60 mm culture plate) five days prior to the beginning of the experiment. Assays were performed on cells only up to passage 15. At T=0, cultures were transferred to serum-free medium, as an apoptosis stimulus, and seed extracts were added. Controls included 10-7 and 5×10-8 M 12-O-tetradecanoyl phorbol-13-acetate (TPA) to ensure the responsiveness of the cell culture. The samples were added to serum free medium and sterile filtered prior to addition to the cultures. Assays were performed in triplicate or quadruplicate. Analyses of the cell responses were made between 18 and 28 hours of serum deprivation. Two assays were performed on each cell culture plate consisting of differential cell counts.

1. All non-adherent or loosely adherent cells were removed from the culture dish and counted by appropriate techniques, typically counting by electronic particle counting instrument. These are the apoptotic cells, the serum deprived released cells (SDR), released by the action of cultivation in serum-free medium. Approximately 95% of these released cells are apoptotic as shown by both ultrastructure analysis and DNA fragmentation analysis.

2. The remaining adherent cells (ADH) were exposed to a buffered, typically pH 7.3, balanced salt solution such as Hanks Balanced Salt Solution without calcium and magnesium salts containing 0.05% trypsin and 0.53 mM ethylene diaminetetraacetic acid (EDTA). Each culture was incubated at either room temperature or 37° C. on a rocking platform to ensure uniform distribution of the trypsin reagent over the culture surface. After a standardized period of time, typically 10 minutes, the released cells were removed from each culture dish and measured by the same means as described above, typically electronic particle counting. This ADH cell count is comprised of both trypsin resistant and trypsin sensitive cells as described in U.S. Pat. Nos. 5,637,486, 5,620,888, and 5,681,703.

Anti-apoptotic activity is expressed in the following examples as the calculated concentration of material ($\mu$g/ml of media) required to save 50% of the cells released on serum free treatment.

EXAMPLE 3

Preparation of Five Phospholipid Mixture

Commercially available purified soy phospholipids containing lysophosphatidic acid and the following other phospholipids: PA, PI, LPI, LPC (available, for example, from Avanti® Polar Lipids, Inc.) were suspended in 50 mM ammonium bicarbonate pH 8.0 containing 154 mM NaCl or buffered aqueous solutions free of divalent cations having a pH range of 5 to 8. Total concentrations of phospholipids of greater than 10 mg/mL can be used provided that clarity is obtainable upon sonication. Total concentrations of up to about 50 mg/mL have been utilized.

Typically, the phospholipid mixtures are suspended in a buffer and the mixture is placed in a disposable borosilicate glass, preferably 1–2 mL in a 16×100 mm tube or 0.5–2 mL in a 13×100 mm tube, or up to 1 mL in a 12×75 mm tube. The combination of phospholipids is then sonicated. Preferably, a small bath sonicator is used, such as a that sold by Laboratory Supplies, Hicksville, N.Y. The temperature of the water bath is between about 21 and 50° C., preferably between about 21° C. and about 40° C. The optimal temperature depends on the phospholipids used and can be determined empirically. The water level is adjusted so that it is approximately the same height as the phospholipid mixture in the glass tube(s). Alternatively, a probe sonicator can be used (Fisher Scientific Sonic Dismembrator model 550), as long as care is taken to prevent overheating of the mixture.

The mixture was sonicated for between 3 and 90 minutes, with alternating 5 minute intervals of sonication followed by 5 minutes of thermal equilibration, in a 1–2 ml volume until the mixture became translucent and passed readily through a filter attached to a 5 ml syringe with a pore size of 0.22 $\mu$m. Preferably, sonication is for 5–10 minutes.

The stability of the compositions at various temperature was determined. The compositions were stored for one week at 4° C., room temperature, and 65° C. The results show loss of activity after storage at 65° C., while the compositions stored at 4° C. or at room temperature do not have a significant loss of activity.

Optimization of each constituent phospholipid was determined by mixing the purified phospholipids in various ratios, varying one phospholipid at a time. Each mixture was analyzed for anti-apoptotic activity as described in Example 2. When the apparent optimized ratio was obtained, the ratio of the most active ingredient was varied to find the absolute optimized activity. Table 2 shows the final ratios tested (10:10:8:2:4 is the "Five Phospholipid Mixture" referred to herein).

TABLE 2

| PA:PI:LPA:LPI:LPC |
|---|
| 10:10:2:2:1 |
| 10:10:2:2:2 |
| 10:10:2:2:4 |
| 10:10:4:2:4 |
| 10:10:4:2:1 |
| 10:10:4:2:2 |
| 10:10:8:2:4 |

The concentration of LPA was varied as was the chain length to determine the effects of these parameters on activity.

EXAMPLE 4

Anti-apoptotic Activity of LPA

The ability of 18:1-LPA and other LPAs to protect serum-starved cells from apoptotic death was measured using the C3H/10T½ cell assay, performed as described in Example 2. The effect of various compounds on the ability of lysophosphatidic acid to protect serum-starved cells from apoptotic death was also measured. Log phase cells were seeded in 60 mm Petri dishes at 175–350 cells per cm2 and maintained in Basal Medium Eagle (BME) supplemented with 10% Heat Inactivated Fetal Bovine Serum (HIFBS). On day 3 the cells were given fresh media. Treatment began on day 5 when the media containing serum was removed and replaced with the LPA mixture to be tested. After 24 hours of treatment, day 6, serum deprived released (SDR) cells (the apoptotic cell population) and adherent (ADH) cells were separated and counted using an electronic cell counter Coulter Corporation, Hialea, Fla.). SDR cells were counted with the lower threshold setting at 6.3 $\mu$m and were defined as the apoptotic cells dying in response to cultivation in serum free media. Approximately 95% of the SDR cells were confirmed to be apoptotic as previously shown by size, ultrastructure and DNA fragmentation analysis. Adherent cells were remove by treatment with 5 mL of Hanks Balanced Salt Solution (HBSS) without ions containing 0.05% trypsin and 0.53 mM EDTA and were counted with the lower threshold setting at 11.01 $\mu$m. All samples were tested in triplicate and serum-deprived controls (BME only) were assayed at both the beginning and end of each experiment.

To test the efficacy of each LPA to inhibit apoptosis or preserve function of serum-deprived cells, 2.5 $\mu$Mol of dried LPA was dissolved (via approximately 5 minute sonication) in 1 mL of citrate-saline (10 mM Na Citrate, 139 mM NaCl) to give a 2.5 mM stock solution and presented to the cells at four concentrations: 1, 3, 10 and 30 $\mu$M LPA. The results are shown in FIG. 1 (lysophosphatidic acid) and Table 3. The effects of LPA alone or in combination with various proteins or liposomes are expressed as percent cells saved.

TABLE 3

| Compound # | Concentration for Max Effect ($\mu$M) | Maximum effect relative to 18:1 LPA |
|---|---|---|
| 78 | 1 | 160% |
| 68 | 1 | 150% |
| 48 | 1 | 130% |
| 66 | 1 | 130% |
| 18:1 LPA | 10 | 100% |
| 18:2 LPA | 10 | 100% |

TABLE 3-continued

| Compound # | Concentration for Max Effect (μM) | Maximum effect relative to 18:1 LPA |
|---|---|---|
| 24 | 10 | 100% |
| 12 | 10 | 100% |
| 16 | 10 | 100% |
| 30 | 30 | 100% |
| 16:0 LPA | 10 | 80% |
| 14:0 LPA | 30 | 80% |
| 71 | 100 | 76% |
| 46 | 30 | 75% |
| 37 | 30 | 75% |
| 61 | 30 | 70% |
| 19 | 30 | 50% |
| 10:0 LPA | 30 | 30% |
| 24:1 LPA | 30 | 30% |
| 23 | 30 | 17% |
| 33 | ND | |
| 70 | ND | |
| 11 | ND | |
| 39 | ND | |
| 38 | ND | |
| 6:0 LPA | ND | |
| 15 | ND | |
| 29 | ND | |
| 25 | ND | |
| 45 | ND | |
| 36 | ND | |
| 4 | 10 | Toxic |
| 59 | 30 | Toxic |
| 8 | 30 | Toxic |
| 3 | 30 | Toxic |
| 53 | 100 | Toxic |

ND: no protection detected.

For those compounds exhibiting toxicity, the dose shown is the lowest concentration at which cytotoxic effects were observed.

In medium alone, approximately 80% of serum-deprived 10T½ cells were non adherent following 24 serum deprivation. However, 18:1-LPA at various concentrations (1, 3, 10, 30 μM) showed anti-apoptotic activity, protecting 35% to approximately 53% of the cells. 18:1-LPA combined with polyethylene glycol or BSA also protects serum-deprived 10T½ cells from apoptosis.

When 18:1-LPA (at the same various concentrations) was combined with BME (containing calcium) and filtered prior to presentation to serum-deprived 10T½ cells, the anti-apoptotic activity of 18:1-LPA appeared to be inhibited. The addition of BSA apparently preserved the anti-apoptotic activity of 18:1-LPA despite the presence of calcium, as seen when 18:1-LPA (at the same various concentrations) was combined with BSA in BME (containing calcium) and presented to serum-deprived 10T½ cells.

Figure 2:
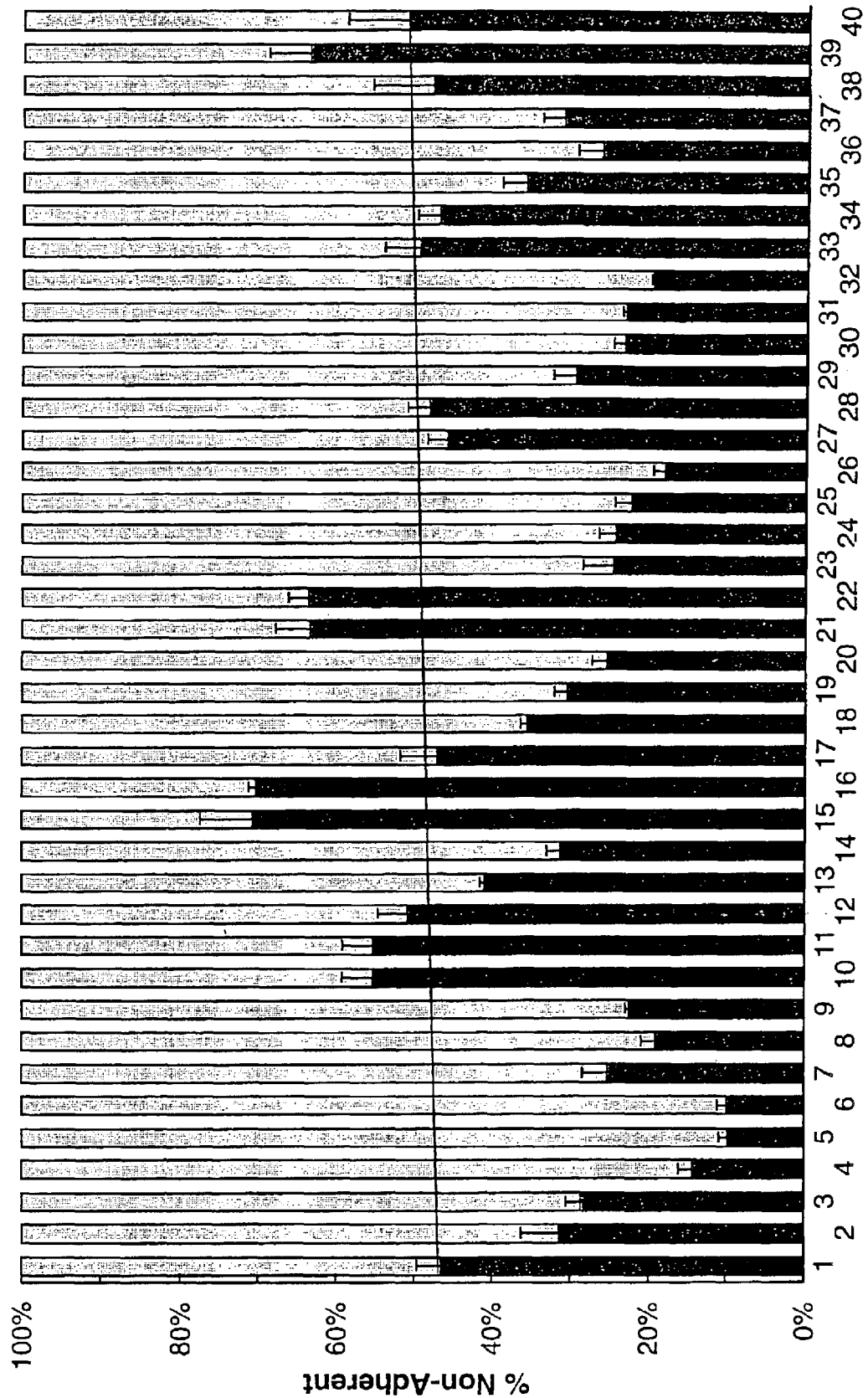
FIG. 2 is a bar graph depicting the percentage of adherent cells (open bars) and non-adherent cells (solid bars) in the C3H/10T½ assay after 24 hours exposure to serum-free medium to which 18:1-LPA was added as a 10% (by weight) mixture in various phospholipid membrane structures. For all treatments, 18:1-LPA was delivered at 0.25, 0.75, 2.25 or 6.75 μg/mL.

To test the efficacy of LPA, presented in a lipid membrane structure, to inhibit apoptosis in serum-deprived cells, LPA was incorporated into lipid membrane structures of various lipid compositions. Except in the Five Phospholipid Mixture treatments, LPA was presented to the cells as 18:1-LPA, and was tested in all preparations at four concentrations: 0.25, 0.75, 2.25 and 6.75 μg/ml. The results are shown in FIG. 2. In medium alone, approximately 50% of the cells died of serum deprivation-induced apoptosis. Phosphatidylserine (PS) alone was slightly toxic. When 18:1-LPA at 0.75 μg/ml was added together with PS, approximately 75% of cells were protected. Positively charged particles containing 18:1-LPA combined with the neutral phospholipid phosphatidyl choline (PC) and 20 mol % of the positively charged lipid 1,2-dioleoyl-3-trimethylammonium-propane (TAP) were efficacious in protecting 70 to 80% of cells, compared with PC/TAP alone, offered no protection over control. Incorporation of 18:1-LPA into the negatively charged phosphatidyl glycerol (PG) gave even better protection, with up to 90% of cells protected as compared to alone which offered no protection over control. However, inclusion in the 18:1-LPA/PG particles of 5 to 10 mol % of the neutral phospholipid phosphatidylethanolamine (PE) with a long polyethylene glycol (2000 MW) covalently linked to the polar head group resulted in reduced efficacy of 18:1-LPA. Taken together, these data suggest that LPA, presented in particles as a 10% by weight mixture with either PC or PG, afforded a degree of protection similar to that achieved with Five Phospholipid Mixture against serum deprivation-induced apoptosis.

Figure 3:
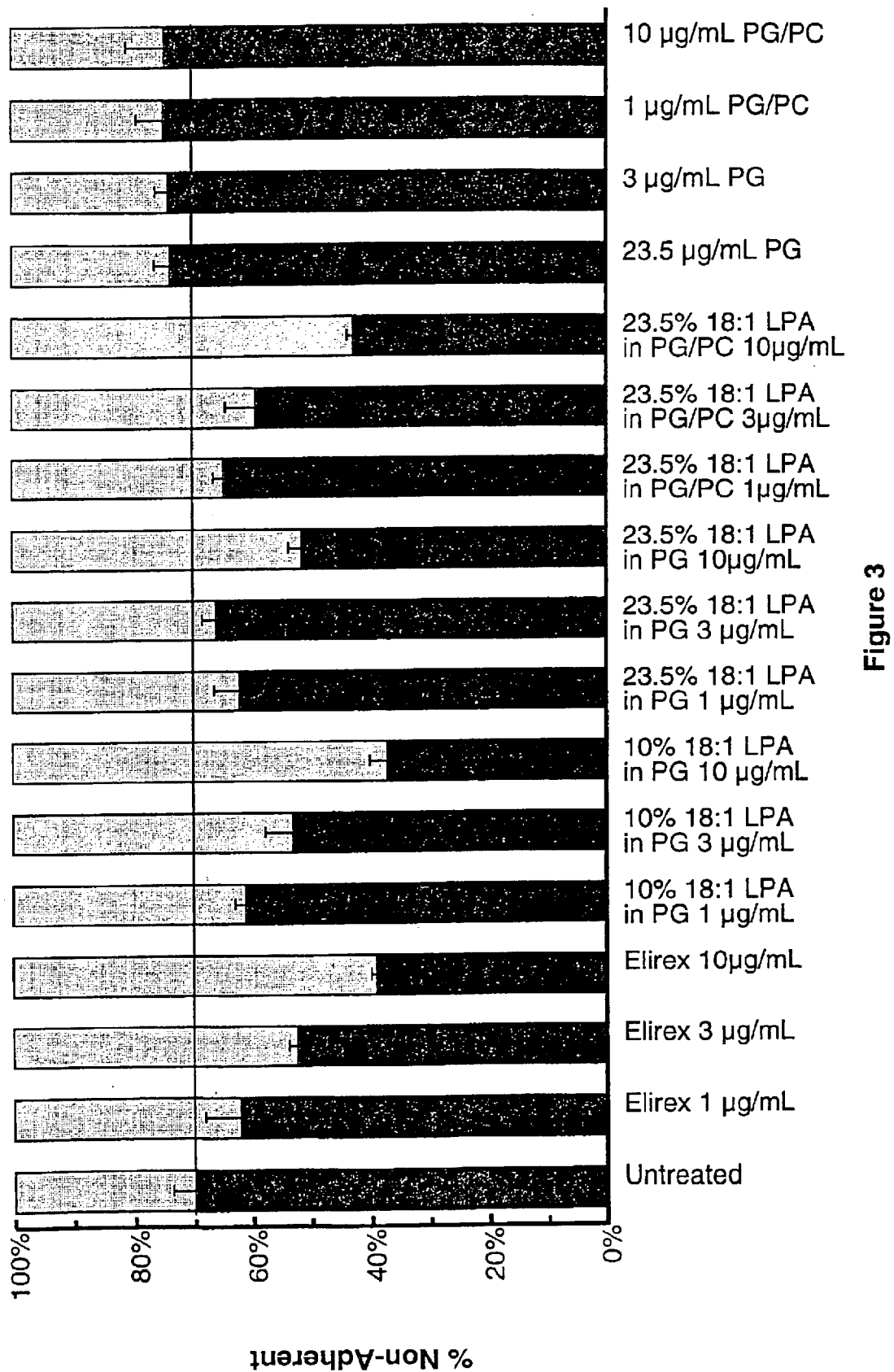

LPA was then tested in two different weight ratios with PG, using 18:1-LPA in concentrations representing LPA equivalents to Five Phospholipid Mixture at 1, 3, or 10 μg/ml. As shown in FIG. 3, LPA equivalent to 10 μg/ml Five Phospholipid Mixture incorporated into particles at 10% by weight with PG protected approximately 65% of cells from apoptosis. This degree of protection was roughly the same as that afforded by Five Phospholipid Mixture alone. Increasing the weight percent of 18:1-LPA to 23.5 resulted in a reduction of the proportion of cells saved to about 50%. Incorporation of 18:1-LPA into particles containing 1:1 ratio PG:PC with 23.5% by weight 18:1-LPA gave particles that protected about 57% of cells. In this assay, in medium alone, only about 30% of cells survived serum-deprivation, and when PC or PG/PC mixtures alone were added to the culture medium, only about 25% of cells survived.

Figure 4:
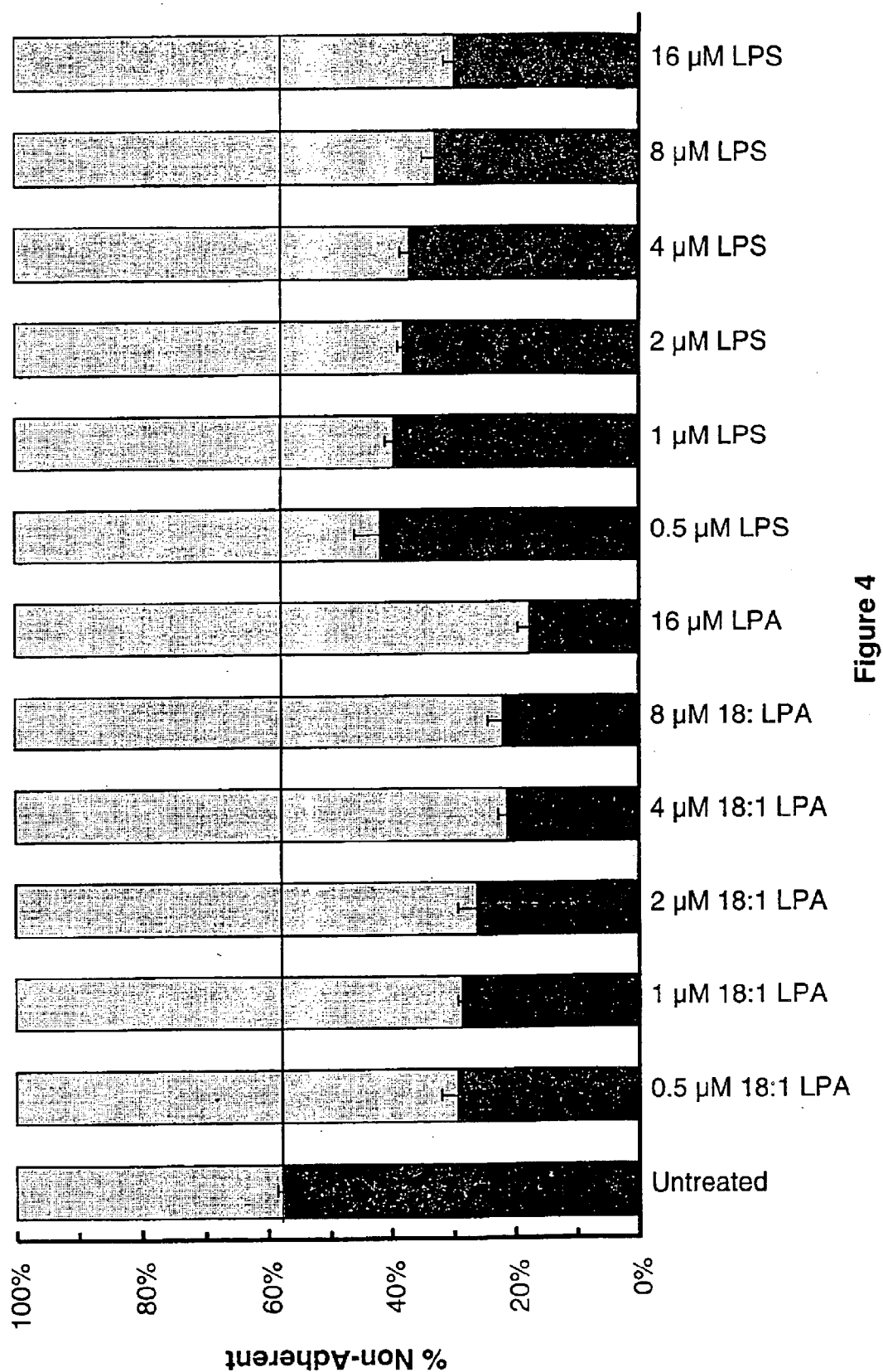
Figure 5:
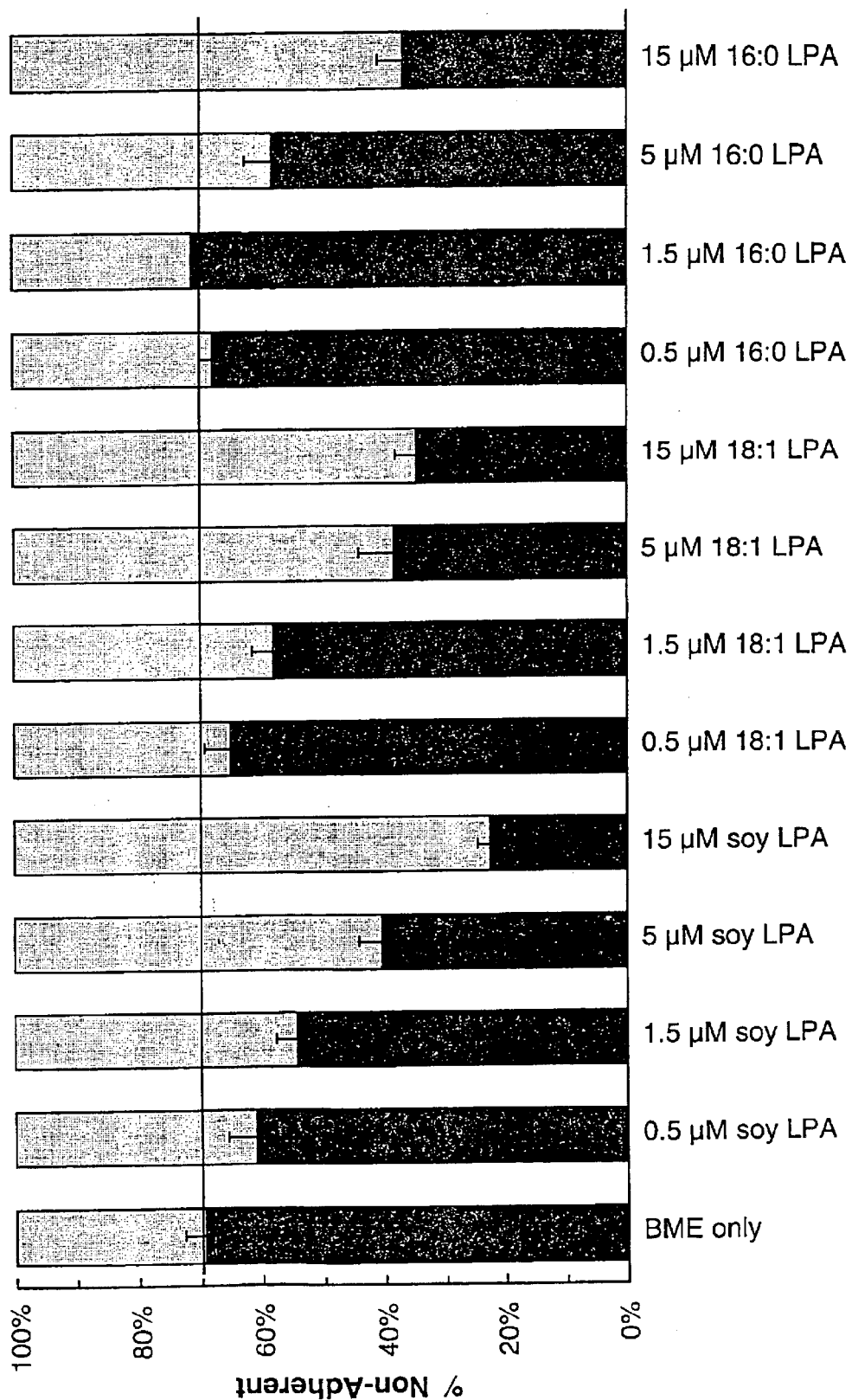
Figure 6:
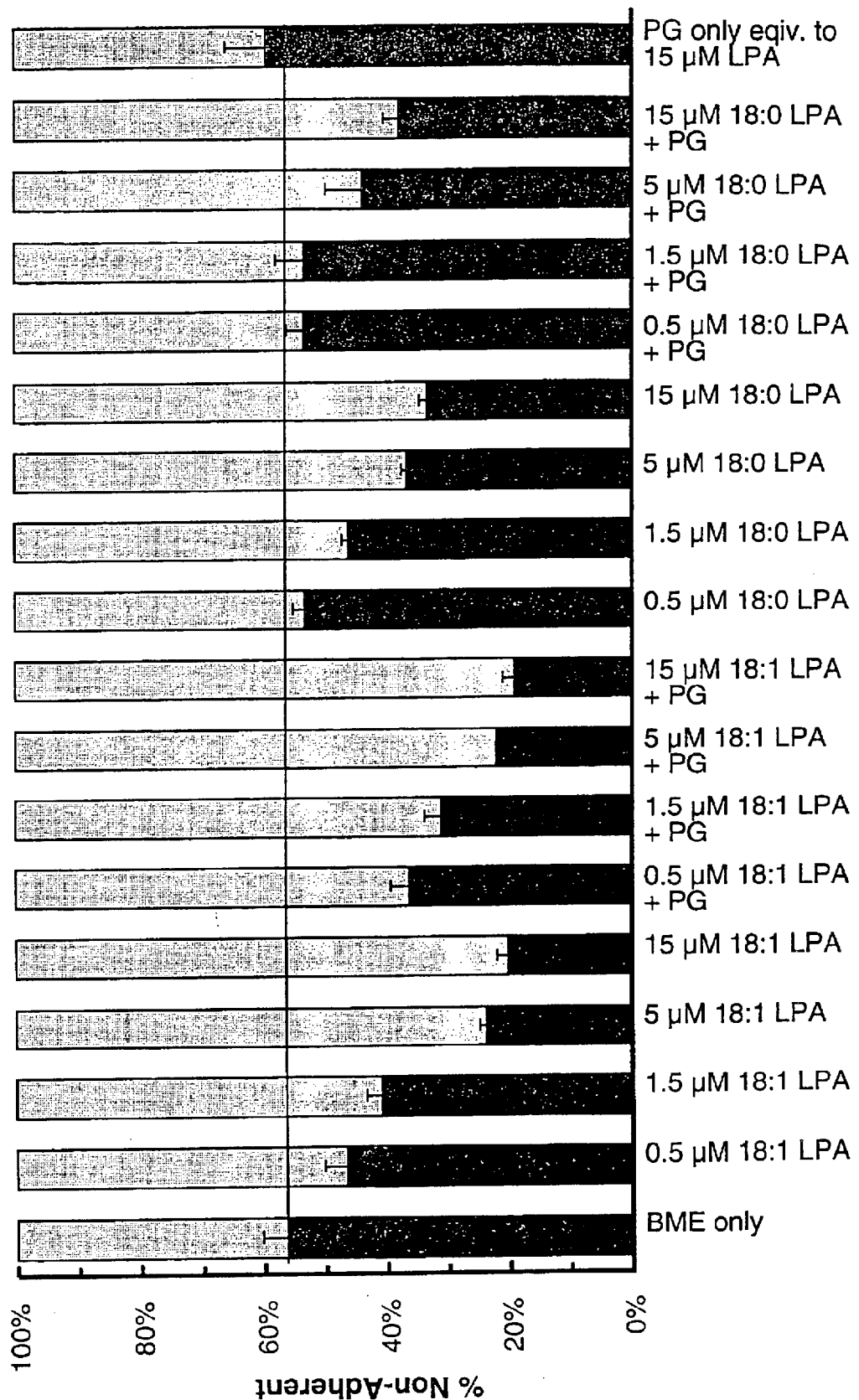

Various other natural lysophospholipids were tested for ability to protect cells from serum deprivation-induced cell death. Of the phospholipids tested, only lysophosphatidyl serine (LPS) showed any significant activity in the C3H10T½ assay. On a molar basis, LPS was approximately 50% as active as 18:1-LPA (FIG. 4). Palmitoyl-LPA (16:0 LPA) at 15 μM protected 63% of cells, which was similar to the protection afforded by 15 μM 18:1-LPA. However, differences were seen at lower concentrations of the two LPAs: 5 μM 18:1-LPA protected about 62% of cells, while 5 μM palmitoyl-LPA protected only about 42% of cells, compared with a medium alone control of 30% protection (FIG. 5). Similarly, stearyl-LPA at 15 μM and at 5 μM protected 65 and 63% of cells, respectively, while 18:1 LPA at 15 μM and 5 μM protected 80% and 75%, respectively (FIG. 6). Stearyl-LPA and 16:1-LPA as 10% dispersions in PG gave similar degrees of protection.

Figure 7:
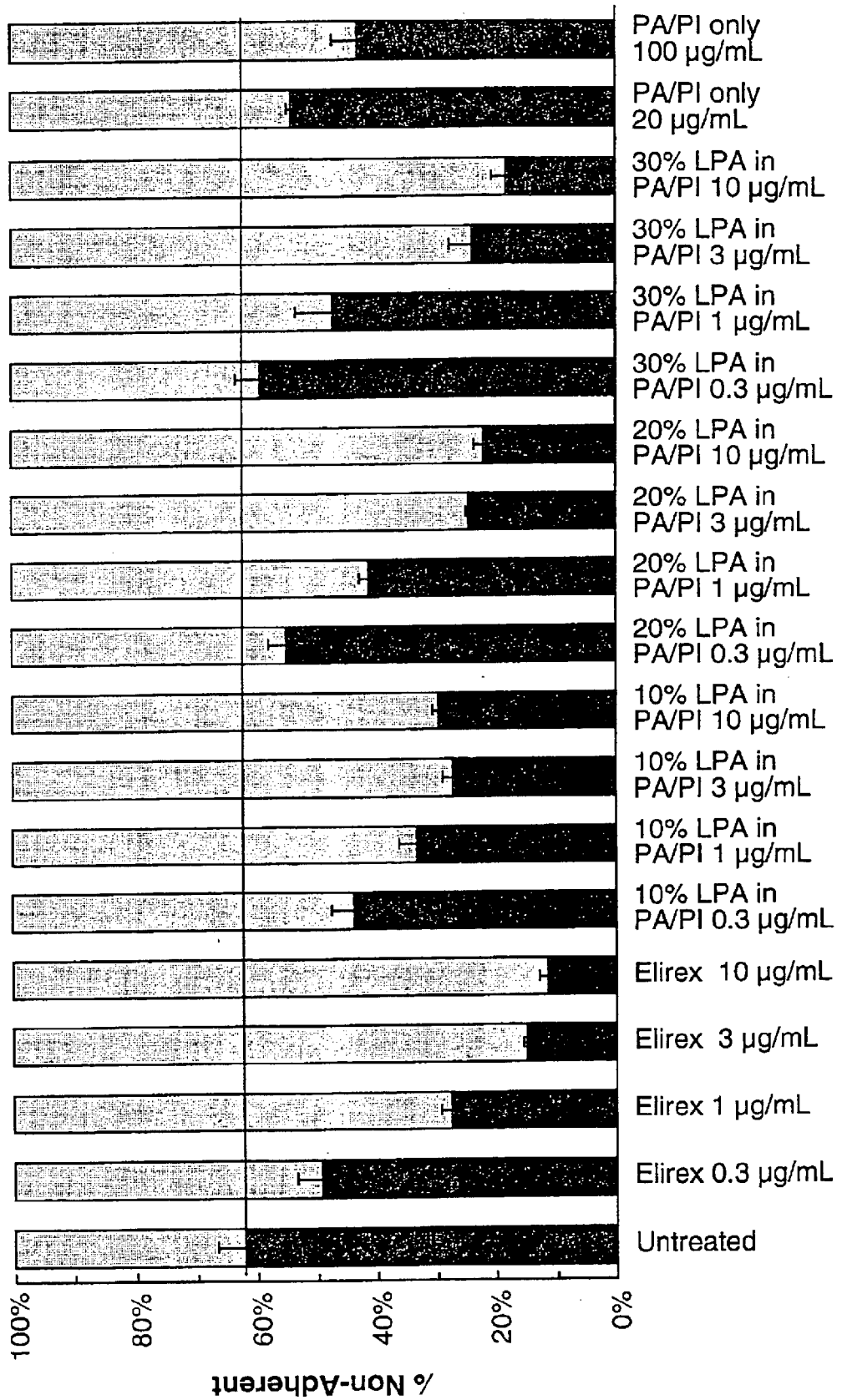

The efficacy of various mixtures of oleoyl-lysophosphatidic acid and phosphatidic acid (PA) :phosphatidyl inositol (PI) was also tested. oleoyl-lysophosphatidic acid was mixed at 10, 20 and 30% by weight with PA:PI at a 1:1 (by weight) ratio and tested in the C3H10T½ serum deprivation assay. The results (FIG. 7) indicate that oleoyl-lysophosphatidic acid presented to C₃H10T½ cells at the time of serum deprivation as a 30% (by weight) mixture with 1:1 PA:PI in a final concentration equivalent to Five Phospholipid Mixture at 10 μg/ml afforded nearly the same degree of protection (about 82% of cells protected) as Five Phospholipid Mixture at 10 μg/ml (about 87% of cells protected), compared to a medium alone control value of 38%.

18:1-LPA was presented to C3HT10½ cells at the time of serum deprivation as a 10% (by weight) mixture with PC, PC containing 5 mol % phosphatidyl ethanolamine-N-polyethylene glycol (PE-PEG), or PC containing 20 mol % 1,2-di-oleoyl-sn-glycero-3-ethylphosphocholine (EtPC).

Figure 8:
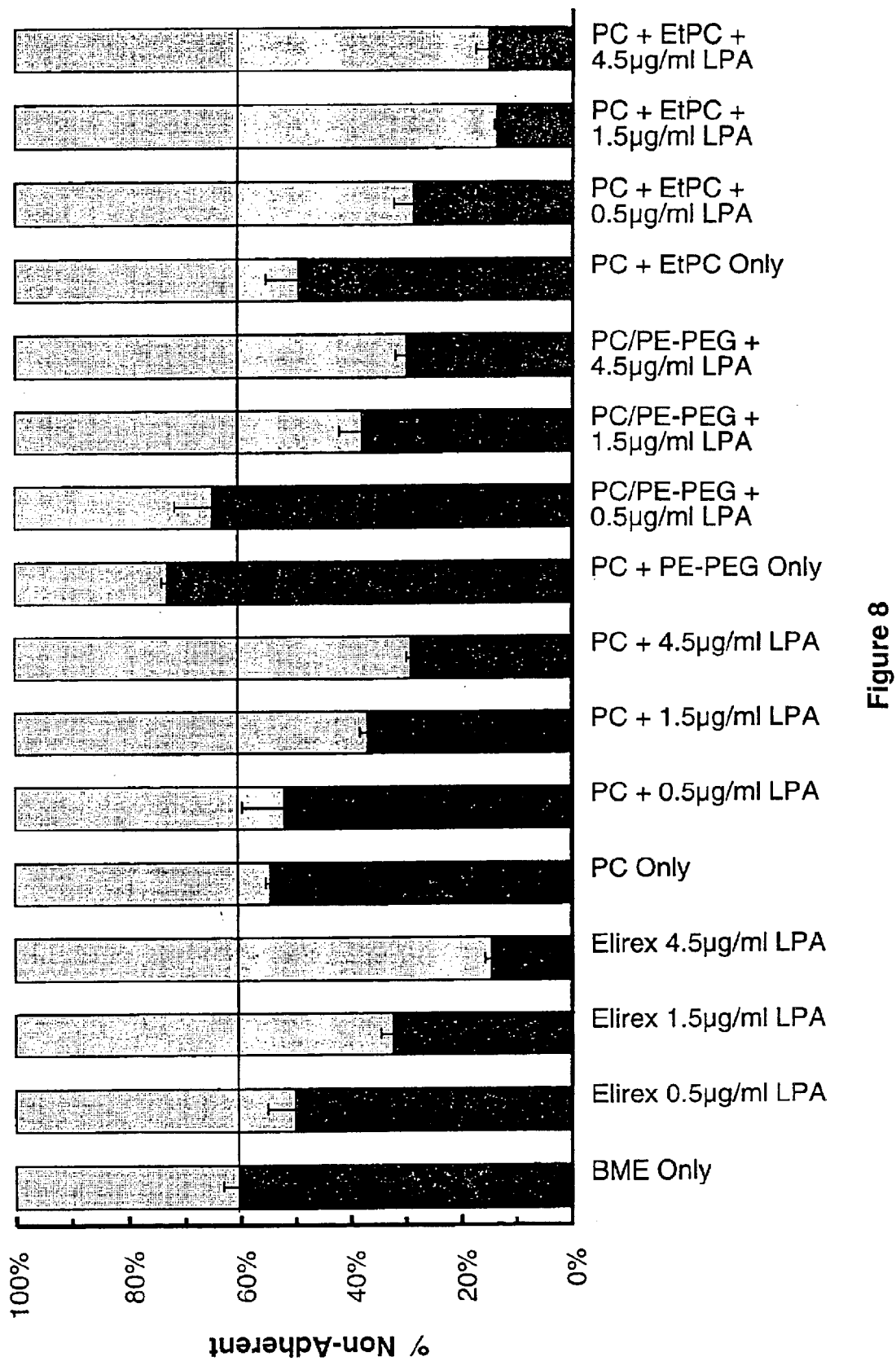

The results, in FIG. 8, show that preparations containing LPA incorporated into PC, PC/PE-PEG, or PC/EtPC were all effective in protecting cells from serum deprivation-induced cell death, with 18:1-LPA/PC/EtPC liposomes providing as much protection (approximately 85% of cells protected) as Five Phospholipid Mixture.

The analogs and derivatives of lysophosphatidic acid that were tested (Table 3) generally showed activity similar to lysophosphatidic acid. One genus of LPAs, the phosphothionate analogs, (exemplified by the following compositions: 3-O-Oleoyl-2-O-methyl-rac-glycero-1-thiophosphate, Oleyl 1-thiophosphoryl-2-O-methyl-rac-glycerate, and 3-O-Oleyl-2-O-methyl-rac-glycero-1-thiophosphate), showed activity significantly higher than lysophosphatidic acid.

EXAMPLE 5

Preparation of Protein/LPA Mixtures

Soy derived LPA (soy-LPA) (Avanti® Polar Lipids, Inc., Alabaster, Ala.) was stored in an organic solution and was dried immediately prior to assay using a Speed Vac (Savant Instruments, Hicksville, N.Y.). Tested proteins were resuspended at 10 mg/mL in a bicarbonate buffered saline/EDTA solution (50 mM $NH_4HCO_3$, 104 mM NaCl, 250 $\mu$M EDTA) prior to being added to dried soy-LPA at a 1:10 soy-LPA to protein (weight:weight) ratio. The mixture was then sonicated for 5 minutes using a high power 80 Watt sonication bath (Laboratory Supplies Co., Hicksville, N.Y.). Following sonication, concentrated LPA/protein mixtures were left standing for 15 minutes at room temperature prior to dilution in cell culture assay media.

EXAMPLE 6

Effects of Protein on Anti-apoptotic Activity of LPA

The effect of various proteins on the ability of LPA to protect serum-starved cells from apoptotic death was measured using the C3H/10T½ cell assay, performed as described in Example 2, above. Log phase cells were seeded in 60 mm Petri dishes at 175–350 cells per cm² and maintained in Basal Medium Eagle (BME) supplemented with 10% fetal calf serum (Hyclone, Logan, Utah). At time zero, serum containing media was replaced with sterile filtered BME containing the LPA/protein mixture to be tested. After 24 hours of treatment, serum deprived release (SDR) cells (the apoptotic cell population) and adherent (ADH) cells were separated and counted using an electronic cell counter (Coulter Corporation, Hialea, Fla.). SDR cells were counted with the lower threshold setting at 6.3 $\mu$m and were defined as the apoptotic cells dying in response to cultivation in serum-free-media. Approximately 95% of the SDR cells are confirmed to be apoptotic as previously shown by size, ultrastructure and DNA fragmentation analysis. Adherent cells were removed by treatment with a Hanks' balanced salt solution containing 0.05% trypsin and 0.53 mM EDTA and were counted with the lower threshold setting at 11.01 $\mu$m. All samples were tested in triplicate and serum-deprived controls (BME only) were assayed at both the beginning and end of each experiment.

The results are shown in Table 4. The effects of various proteins alone or in combination with LPA are expressed as percent cells saved from apoptosis. When C3H10T½ cells were treated with 10 $\mu$g/mL soy LPA without protein, 8.0% of the cells were saved. The degree of protection from apoptosis afforded by protein alone, added to the medium at a concentration of 0.1% (wt/vol.), varied from 0.9% to 27.7% of cells saved from apoptosis. An unusually high percentage of cells were protected from serum-starvation-induced apoptosis by casein. This value may be artificially high, as casein preparations have been known to contain growth factors, including insulin-like growth factors (IGF) IGF1 and IGF2. IGF2 is a mitogen that can mask the serum deprivation-induced apoptotic response in these cells.

When soy-LPA was added together with protein, the degree of protection from apoptosis was, for certain proteins, more than additive. Thus, fatty acid depleted (FAD) bovine serum albumin (BSA) alone protected 0.9% of cells from serum-induced apoptosis, soy-LPA alone protected 8.0% of cells, while FAD BSA plus soy-LPA saved 58.7% of the cells. Similar effects were seen for mixtures of soy-LPA with FAD soy protein, cytochrome c and low density lipoprotein (LDL) and, to a lesser degree, acyl carrier protein, casein and myoglobin. Soybean trypsin inhibitor, ovalbumin, retinol binding protein and myelin basic protein did not enhance the anti-apoptotic activity of LPA, while bromolain was toxic to the cells.

TABLE 4

| Protein | Source | Protein Alone (0.01%) | Protein + 10 $\mu$g/mL Soy LPA | Increase with LPA | Detectable Acrylamide Gel $^3$H LPA Binding (+/−) | 3H-LPA Size Shift Analysis (+/−) |
|---|---|---|---|---|---|---|
| Albumin (Fatty Acid Depleted) | Bovine serum | 0.9 | 58.7 | +57.8 | + | + |
| Soy Protein (Fatty Acid Depleted) | Soybean | 5.6 | 51.6 | +46.0 | did not resolve on native gel | + |
| Cytochrome C | Bovine heart | 16.2 | 54.6 | +38.4 | did not resolve on native gel | − |
| Low Density Lipoprotein (LDL) | Human plasma | 25.9 | 63.4 | +37.5 | − | not tested |
| Acyl Carrier Protein | E. coli | 8.1 | 36.2 | +28.1 | not tested | not tested |

TABLE 4-continued

| Protein | Source | Protein Alone (0.01%) | Protein + 10 μg/mL Soy LPA | Increase with LPA | Detectable Acrylamide Gel $^3$H LPA Binding (+/−) | 3H-LPA Size Shift Analysis (+/−) |
|---|---|---|---|---|---|---|
| Casein | Bovine milk | 63.4 | 84.3 | +20.9 | − | not tested |
| Myoglobin | Horse heart | 9.3 | 27.8 | +18.5 | − | not tested |
| Trypsin Inhibitor | Soybean | 4.9 | 12.3 | +7.4 | − | − |
| Ovalbumin | Chicken Egg | 7.9 | 15.1 | +7.2 | + | + |
| Retinol Binding Protein (RBP)[3] | Human urine | 27.7 | 33.3 | +5.6 | − | not tested |
| Myelin Basic Protein[3] | Rabbit brain | 16.8 | 17.0 | +0.2 | − | not tested |
| Bromolain | Pineapple stem | −100 | −100 | 0 | − | not tested |
| α-fetoprotein | Fetal bovine serum | not tested | not tested | not tested | + | not tested |

EXAMPLE 7

Binding of LPA to Protein

Binding of LPA to protein was examined using an electrophoresis radiobinding detection assay and a size shift analysis assay.

Electrophoresis radiobinding assay. Proteins were analyzed on native polyacrylamide gels following incubation with $^3$H-labeled 18:1-LPA. $^3$H-labeled lysophosphatidic acid (1-oleyl) (DuPont NEN Products, Boston, Mass.) was added to tested proteins at 1 nM labeled 18:1-LPA/45 μg protein. Mixtures were incubated in a bicarbonate buffered saline/EDTA solution at 37° C. for 60 minutes. Incubated samples were mixed with native gel sample buffer (312 mM Tris pH 6.8, 50% glycerol, 0.05% bromophenol blue) and loaded entirely onto an 8% discontinuous native polyacrylamide gel. Following electrophoresis, proteins were fixed into the gels using an aqueous solution consisting of glacial acetic acid, 10% (vol/vol) and methanol 30% (vol./vol.) solution. Fixed gels were then incubated for 60 minutes in autoradiography enhancer (EN$^3$HANCE, DuPont NEN Products, Boston, Mass.), and dried onto 3M chromatography paper (Whatman, Clifton, N.J.) and exposed to autoradiography film (X-Omat, Kodak, Rochester, N.Y.) for 72 hours at −80° C.

Figure 9:
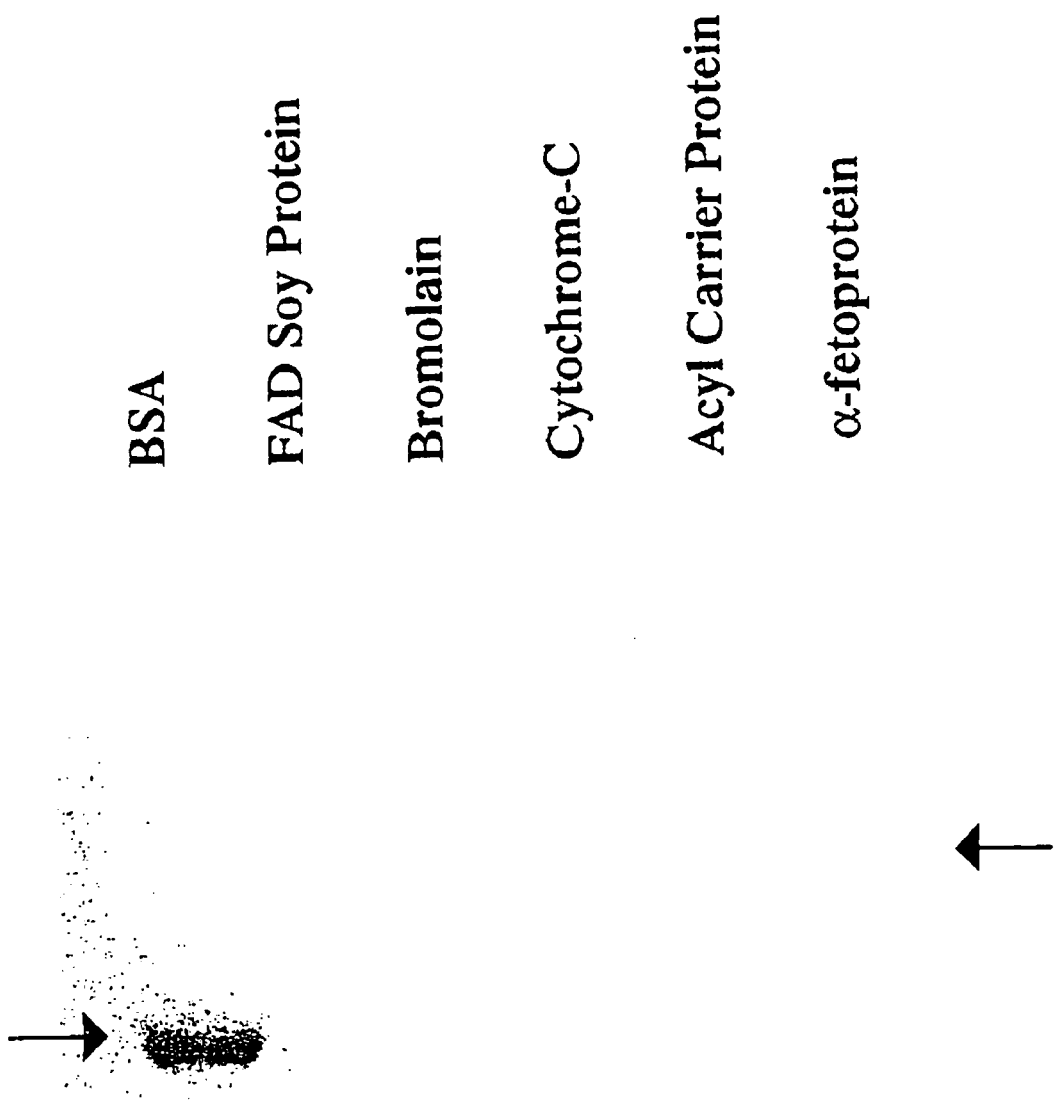
FIG. 9 depicts an autoradiograph of a non-denaturing polyacrylamide gel of proteins separated following incubation with $^3$H-labeled 18:1-LPA.
Figure 10A:
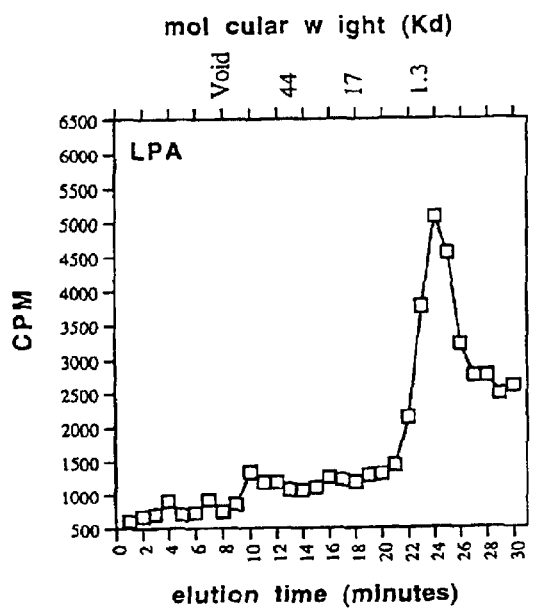
FIGS. 10A, 10B, 10C and 10D are graphs showing the elution profiles of $^3$H-18:1-LPA, with and without various proteins, from a Superdex S75 column.
Figure 10B:
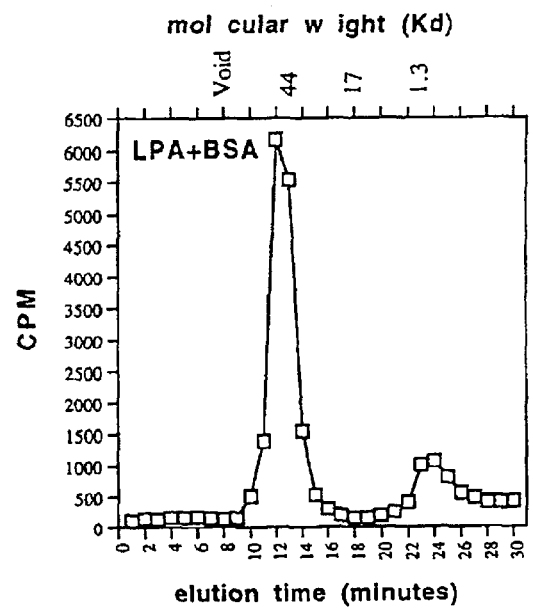
Figure 10C:
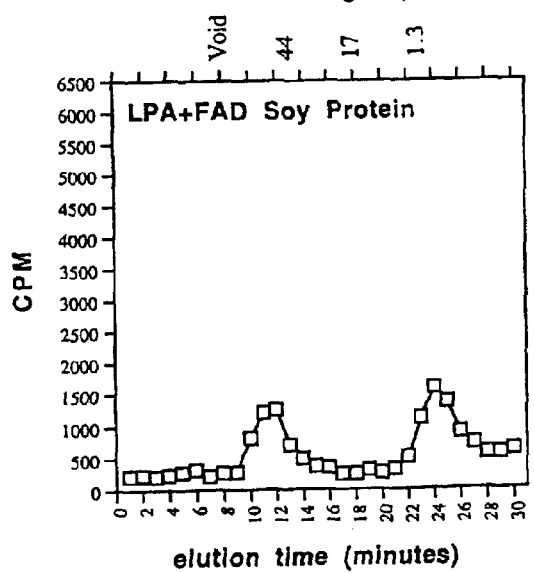
Figure 10D:
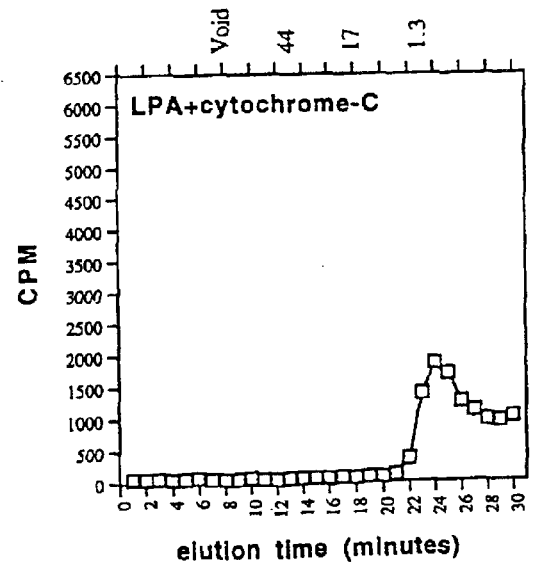

The results, shown in FIG. 9, demonstrate that BSA and α-fetoprotein bind to 18:1-LPA, whereas bromolain and acyl carrier protein did not yield detectable bands. In other experiments, ovalbumin was shown to produce a detectable band (see table 4). Other experiments indicate that FAD soy protein can bind LPA.

Size shift assay. Size analysis of LPA both with and without protein was performed using a Superdex® S75 column (Pharmacia Biotech, Uppsala, Sweden). Soy LPA was combined in a chloroform solution with 0.5 μCi $^3$H-labeled 18:1-LPA (DuPont NEN Products, Boston, Mass.), dried under vacuum and resuspended by sonication in a buffered solution (50 mM ammonium bicarbonate, 154 mM sodium chloride, pH 8.0) in the presence or absence of test protein. The ammonium bicarbonate/sodium chloride solution was used as the mobile phase at a flow rate of 1 ml/min. One-minute fractions were collected for 30 minutes following sample injection. Fractions were counted in scintillant solution using a liquid scintillation counter (Beckman Instruments, Irvine, Calif.). Calibration was performed using a standard solution containing purified proteins (BioRad, Hercules, Calif.).

As shown in FIGS. 10A, 10B, 10C and 10D, soy-LPA alone eluted at 22–26 minutes after sample injection, corresponding to a size of approximately 1.3 kD. When a LPA/BSA mixture was applied to the column, radioactivity eluted primarily in the 10 to 12-minute fractions, indicating that most of the LPA was bound to BSA. A LPA/FAD soy protein mixture applied to the column resulted in an elution profile with two peaks, one corresponding to the position of unbound LPA, and the other shifted. A cytochrome c/LPA mixture gave an elution profile similar to that of soy-LPA alone, indicating that LPA does not bind to this protein.

EXAMPLE 8

Anti-apoptotic Activity of Five Phospholipid Mixture in an Organ Preservation Solution In order to determine the apoptotic activity of the claimed invention, the following experiment was performed. The cell assay is described in Example 2. Exponential growth phase was assured by seeding at 2000 cells per 1 ml (5 ml for a 60 mm culture plate) five days prior to the beginning of the experiment. At T=0, cultures were transferred to serum-free medium, as an apoptosis stimulus, and seed extracts were added. Controls included $10^{-7}$ and $5 \times 10^{-}$M 12-O-tetradecanoyl phorbol-13-acetate (TPA) to ensure the responsiveness of the cell culture. The samples were added to serum free medium and sterile filtered prior to addition to the cultures. Assays were performed in triplicate or quadruplicate. Analyses of the cell responses were made between 18 and 28 hours of serum deprivation with Five Phospholipid Mixture alone in Basal Medium Eagle's (BME) culture medium or supplemented with 5% or 25% of the Cardiosol™ organ preservation solution described in U.S. Pat. No. 4,938,961. Two assays were performed on each cell culture plate consisting of differential cell counts.

1. All non-adherent or loosely adherent cells were removed from the culture dish and counted by appropriate techniques, typically counting by electronic particle counting instrument. These were the apoptotic cells, the serum deprived released cells (SDR), released by the action of cultivation in serum-free medium. Approximately 95% of these released cells were apoptotic as shown by both ultrastructure analysis and DNA fragmentation analysis.

2. The remaining adherent cells (ADH) were exposed to a buffered, typically pH 7.3, balanced salt solution such as Hanks Balanced Salt Solution without calcium and magnesium salts containing 0.05% trypsin and 0.53 mM ethylene diaminetetraacetic acid (EDTA). Each culture was incubated at either room temperature or 37° C. on a rocking platform to ensure uniform distribution of the trypsin reagent over the culture surface. After a standardized period of time, typically 10 minutes, the released cells were removed from each culture dish and measured by the same means as described above, typically electronic particle counting. This ADH cell count was comprised of both trypsin resistant and trypsin sensitive cells as described in PCT Publication No. WO 94/25621.

Anti-apoptotic activity is expressed as the calculated concentration of material (μg/ml of media) required to save 50% of the cells released on serum free treatment.

EXAMPLE 9

Preparation and Use of Five Phospholipid Mixture in PEG20L

Twenty milligrams of Five Phospholipid Mixture stored in $CHCl_3$ (20 mg/mL) under Argon was dried in a glass tube with vacuum concentrator (Savant) with gentle heat. This was sonicated for 5 minutes under an Argon blanket in 1 mL of buffer (50 mM $NH_4HCO_3$, 104 mM NaCl, 250 μM EDTA) 5 mL of which had been bubbled for 5 minutes with Argon.

250 μL (5 mg) of the Five Phospholipid Mixture sonicate was added under a stream of Argon to 100 mL of 10% PEG20L which had been prepared in water, ultrafiltered then sterilized by filtration (0.22 μM) and stored anaerobically (under Argon in Ar-filled bags). The resulting 50 μg/mL Five Phospholipid Mixture in 10% PEG20L was packaged under a stream of Argon into 10 mL autoclaved amber glass vials in 2 mL and 10 mL amounts and sealed with autoclaved butyl rubber septa/aluminum rings. Prior to use, the septa had been subjected to 2 hours of high vacuum then sealed in an aluminum bag filled with Argon in order to displace as much dissolved oxygen as possible. The Five Phospholipid Mixture/PEG vials were labeled then individually packaged into aluminum bags filled with Argon and stored at 4°.

EXAMPLE 10

Activity of LPA and PEG in in vitro C3H/10T½ Assays

Figure 11:
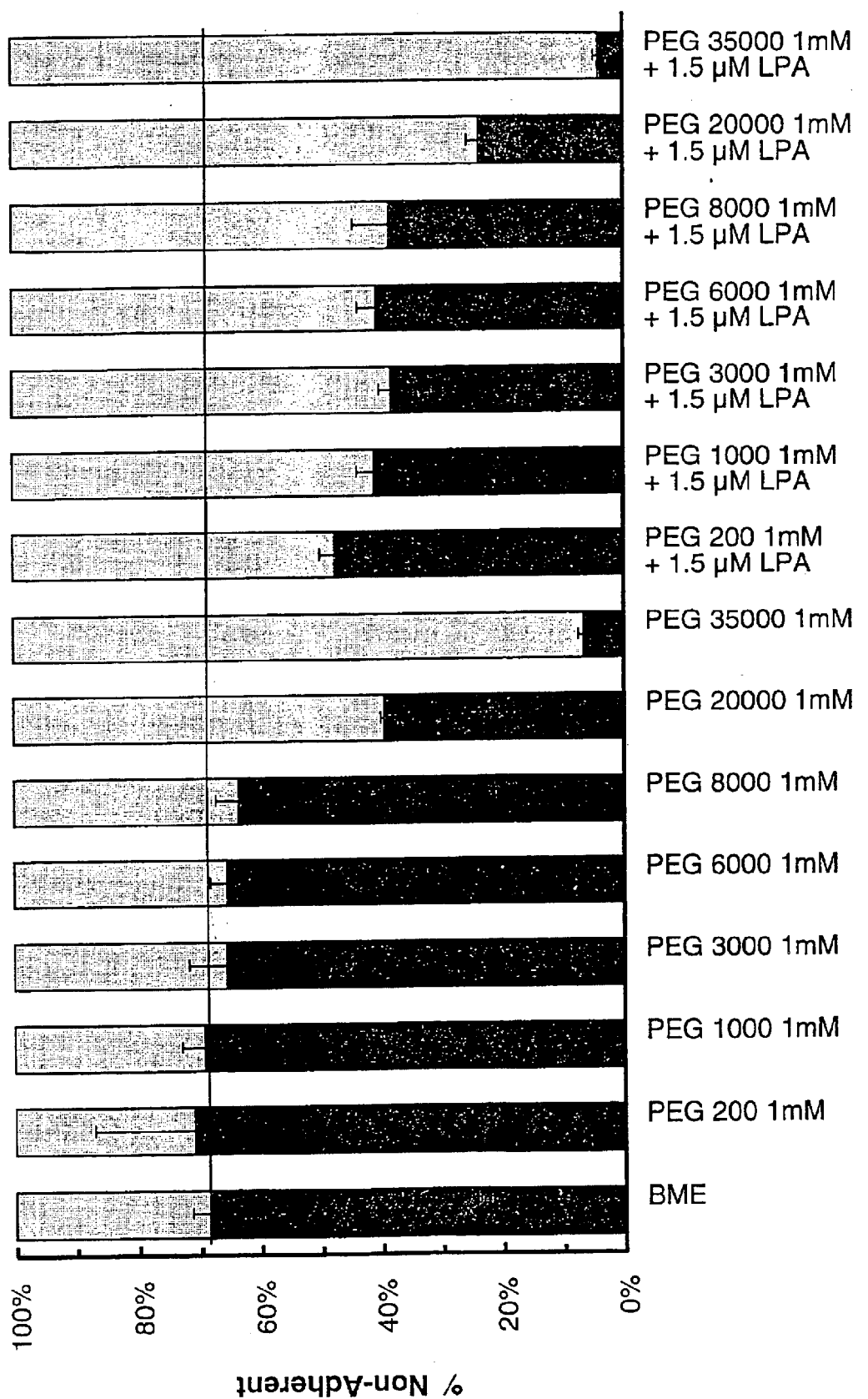
FIG. 11 is a bar graph depicting the effect of polyethylene glycol (PEG) molecular weight on protection of C3H/10T½ cells from serum deprivation at 1 mM in the presence and absence of 1.5 μM 18:1-LPA. PEG of molecular weights 200, 1,000, 3,000, 6,000, 8,000, 20,000 and 35,000 were used. The open section of the bars represents adherent cells and the solid section of the bars represents non-adherent cells.

All the phospholipid mixtures were prepared by combining the desired phospholipids in solution with organic solvent then drying down the mixture with gentle heat (45° C.) and high vacuum followed by sonication into aqueous suspension at 5 to 20 mg/mL. In some cases, the phospholipids were then mixed with serum-free culture medium containing PEG of the indicated molecular weight, concentration and type of PEG noted in the Figures and prepared as described above. The results obtained are depicted in FIG. 11 and Table 3.

EXAMPLE 11 in vitro Cardiomyocyte Assays

Isolation of Rat Neonatal Cardiomyocytes

Cardiomyocytes were prepared from hearts of day-old Sprague Dawley rats by trypsinization and mechanical disaggregation (Simpson, (1985)) Circ. Res. 56:884–894. The cells were resuspended in MEM, 1×MEM vitamins (Gibco), 5% fetal bovine serum and 50 U/ml penicillin-G and preplated for 30 minutes to reduce contamination of nonmyocytes. The non-adherent cardiac myocytes were separated and seeded in 2 ml in 35 mm dishes at a density of $3.5 \times 10^5$ viable cells per ml. The cells were allowed to adhere for 16–24 hours in a 37° C./5% $CO_2$ humidified incubator.

Cardiomyocyte Treatment

For serum deprivation, the medium was replaced with fresh serum-free RPMI, whereas serum/glucose deprivation was performed using glucose-free RPMI. The induction of cell death by adriamycin or $C_2$-ceramide was accomplished by the addition of the agent prepared in serum-free RPMI. As a model of ischemia, cultures in serum and glucose free RPMI were placed in an airtight chamber and the latter was continuously perfused with oxygen-free gas overlay of 95% $N_2$/5% $CO_2$ for 8 hours at 37° C. To model reperfusion of the ischemic cells, 10% fetal bovine serum, 2 μL of glucose were added and the cultures were returned to a normal oxygen gas overlay (37° C./5% $CO_2$) in a humidified incubator for 16 hours.

To investigate effects of LPA, LPA plus other phospholipids, PEG or their mixtures on cell death, various combinations of these components were added to cells in serum free medium at the beginning of cytotoxic treatment.

Measurement of Cell Death

Because cardiomyocytes are terminally differentiated non-dividing cells, viability was determined by measurement of the decrease in the relative number of adherent cells. The measurement of non-adherent cells was found to be less reproducible because of their rapid lysis following release from adhesion substrate. Adherent cardiomyocytes were collected from culture dishes using 0.25% Trypsin/0.05% EDTA and counted on Coulter Counter ZM and Coulter Channelyzer 256.

The results were as follows:

1. Five Phospholipid Mixture prevents cardiomyocyte death induced by serum/glucose deprivation or by ischemia/reperfusion (FIGS. 13, 14).

Figure 13:
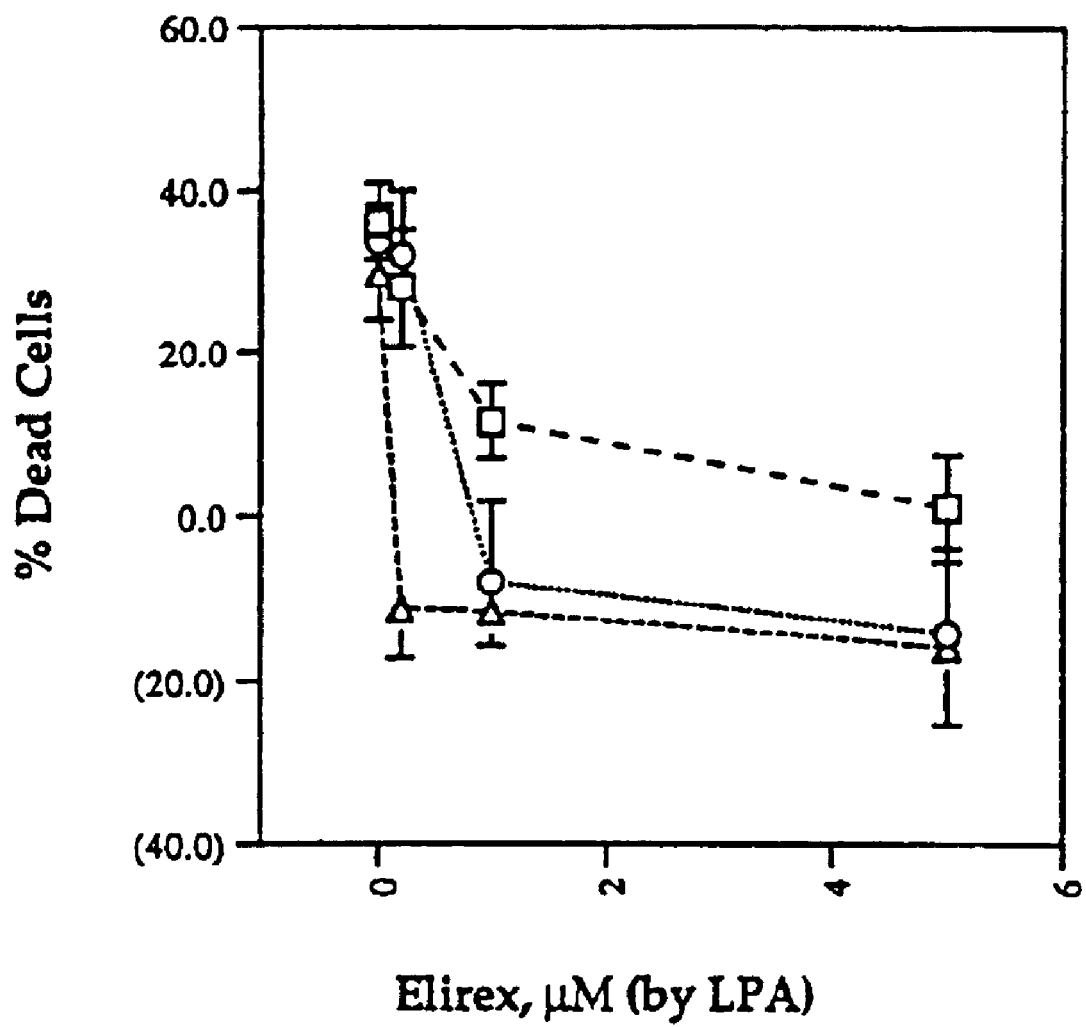
FIG. 13 is a graph depicting the prevention of cardiomyocyte death induced by serum/glucose deprivation by PEG, Five Phospholipid Mixture (referred to in the figure as "Elirex") and a mixture of PEG and Five Phospholipid Mixture. The squares represent no PEG, the circles represent 0.3% PEG and the triangles represent 2% PEG.
Figure 14:
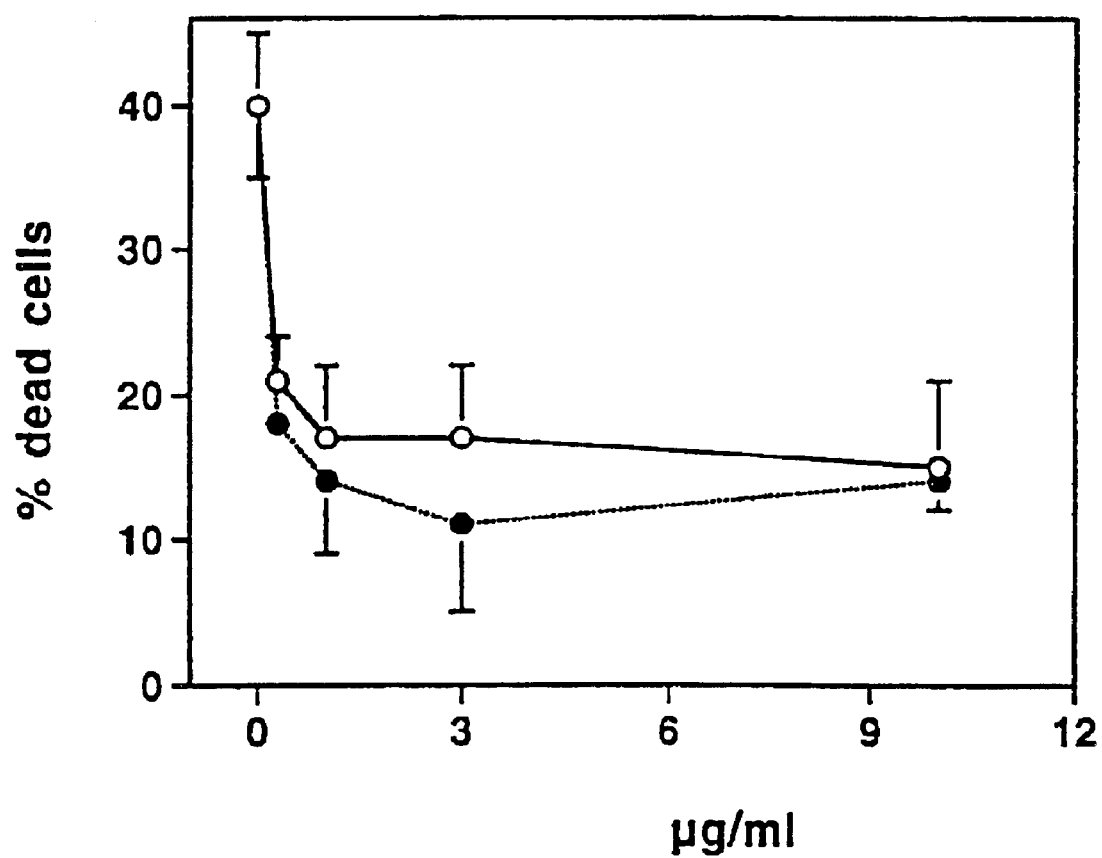
FIG. 14 is a graph depicting the treatment of a pig heart with PEG plus Five Phospholipid Mixture (closed circles) and PEG plus 18:1-LPA (open circles) following ischemia to evaluate the effect of treatment on cardiomyocyte death induced by ischemia and reperfusion. The amount of LPA corresponds to its quantity in the indicated amount of Five Phospholipid Mixture.

2. 0.3–2% PEG with molecular weight 20,000 kDa enhances the protective effect of Five Phospholipid Mixture against serum/glucose deprivation induced cell death (FIG. 13).

3. Mixtures of PEG with Five Phospholipid Mixture and 18:1-LPA equally protect cardiomyocyte death induced by ischemia and reperfusion (FIG. 14).

4. Five Phospholipid Mixture prevents cardiomyocyte death induced enhances this effect (FIG. 15).

5. Various LPAs prevent cardiomyocyte death induced by serum/glucose deprivation (results appear in Table 5).

TABLE 5

| Compound # | Concentration ranges for cardiomyocyte protection (μM) | Maximum effect relative to 18:1 LPA in cardiomyocytes |
|---|---|---|
| 30 | 1–10 | 150% |
| 78 | .01–3 | 130% |

TABLE 5-continued

| Compound # | Concentration ranges for cardiomyocyte protection ($\mu M$) | Maximum effect relative to 18:1 LPA in cardiomyocytes |
|---|---|---|
| 68 | .003–10 | 100% |
| 48 | .03–10 | 100% |
| 18:1 LPA | 0.3–10 | 100% |
| 12 | 1–10 | 100% |
| 11 | 1–10 | 100% |
| 19 | 1–10 | 100% |
| 16 | 1–3 | 100% |
| 66 | .03–1 | 60% |
| 45 | 30 | 30% |
| 46 | ND | |
| 24 | ND | |
| 10:0 LPA | ND | |
| 23 | ND | |
| 15 | ND | |
| 29 | ND | |
| 25 | ND | |
| 36 | ND | |
| 3 | ND | |
| 4 | Toxic (3–30 $\mu M$) | |

ND: No protection detected.

It is clear from these results that LPA has anti-apototic activity as shown in the cardiomyocyte assay, and that the combination of LPA with other phospholipids retains that activity. Additionally, the presence of PEG improves

EXAMPLE 12

Regional Ischemic Dog Heart Model

The experimental model used was a regional ischemic dog heart (mongrel male hound, approximately 20 kg) with the left anterior descending coronary artery clamped distal to the first diagonal branch rendering a portion of the left ventricle ischemic. The clamp was maintained for 90 minutes then released gradually over a 5 minute period. A narrow canula was placed into the left main coronary artery through which Five Phospholipid Mixture (5 mL of 50 $\mu g/mL$ in 10% PEG) was infused starting 75 minutes after the start of the ischemic period, and containing for 75 minutes in total (approximately 67 $\mu L/min.$, approximately 3.3 $\mu g$ Five Phospholipid Mixture/min.). The total dose was 250 $\mu g$ Five Phospholipid Mixture and 500 mg PEG20L.

Determination of Infarct Size

After staining and fixation, the atria and right ventricle are removed from the left ventricle. After removal of the apex, the portion of the left ventricle distal to the mitral apparatus is cut into 5 transverse sections of equal thickness. Evans Blue dye injected into the circumflex vessel stains the circumflex territory blue. TTC stains viable LAD territory red, while the infarcted myocardium will remain unstained (white). Sections are weighed and photographed for documentation and future verification of results. Computer assisted planimetry is used to measure the areas of the circurnflex, viable LAD and infarcted LAD territories. Calculation of infarct size is based upon the assumption that the area of infarction in the sectioned plane is representative of the mass of infarcted tissue in that plane.

Study Protocols

1. Study-drug group; dogs are treated with Five Phospholipid Mixture 50 $\mu g/ml$ and PEG 100 mg/ml as a bolus plus infusion (at 4 ml/hr) starting 15 min before reperfusion and going on for 60 min into the reperfusion period.

2. Placebo group: dogs receive placebo following the same modalities described for the study drug group 3. SOD-Catalase group: dogs receive SOD plus catalase following the same modalities described by Simpson et al. (1987) Fed. Proc. 46:7, 2413–21.

The rationale for using a third group of dogs in the present protocol resides in the fact that the SOD+ Catalase group represents a positive control. In fact it has been shown that the combination of oxygen radical scavenger is very efficacious in limiting myocardial reperfusion injury in the canine mode.

Figure 16:
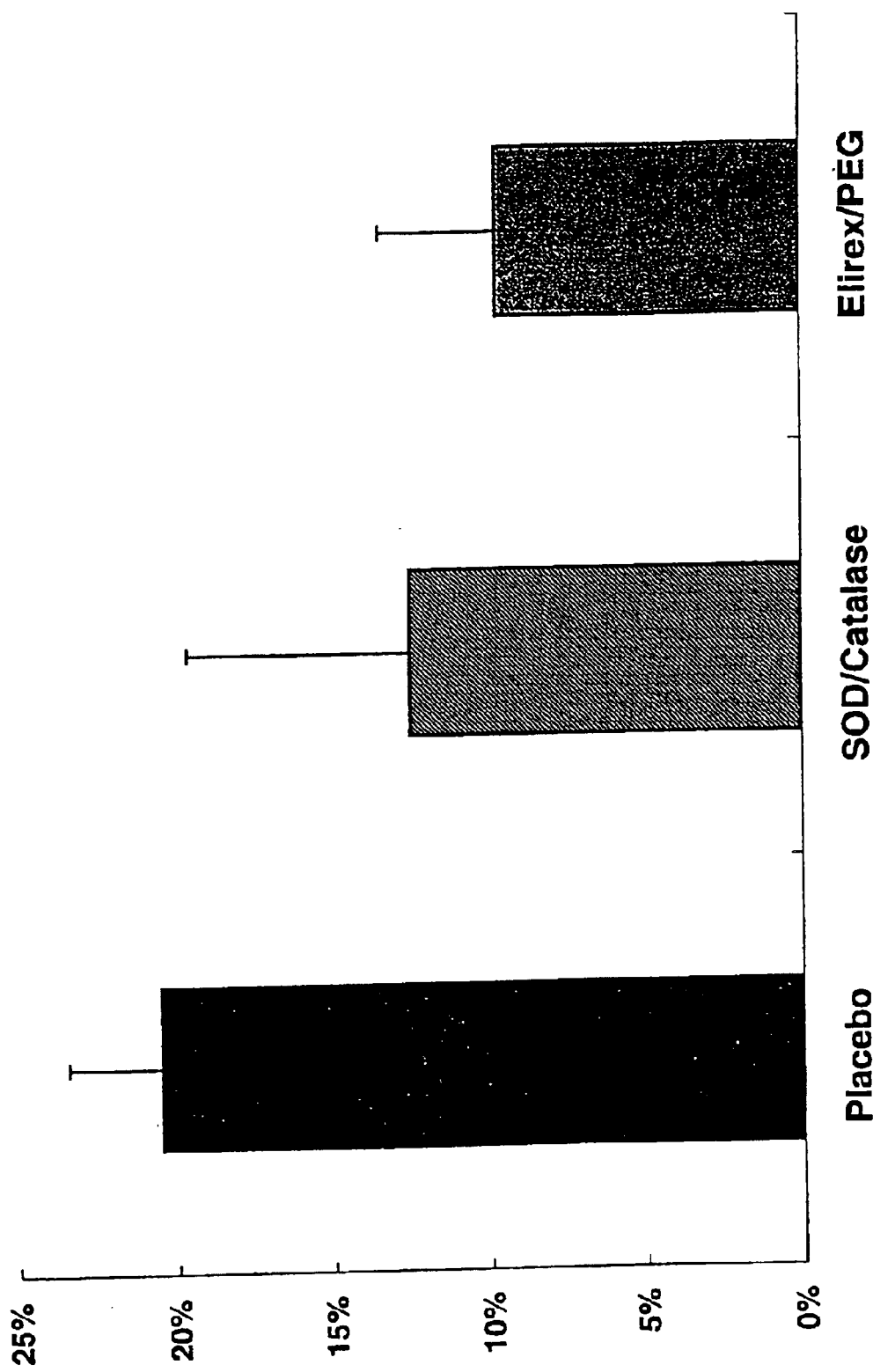
FIG. 16 is a bar graph depicting the actual infarct size compared to the area at risk in the dog heart model treated with placebo (solid bar), a mixture of superoxide dismutase (SOD) and catalase (striped bar) and a dose of the combination of Five Phospholipid Mixture (12.5 µg/kg) and PEG (25 mg/kg) (white bar).

The results obtained in the dog heart experiments are depicted in FIG. 16.

EXAMPLE 13

Evaluation of Infarct Measurement and EKG Alterations in a Regional Ischemic Pig Heart Model This example evaluates the anti-apoptotic activity of PEG20L in a regional ischemic pig heart model. Miniature pigs (approx. 30 kg each) were treated with general anesthesia followed by balloon catheterization to create an occlusion of the first obtuse marginal branch of the circumflex coronary artery. After 105 minutes of occlusion treatment with control, infusion of PEG20L (100 mg/mL), or PEG20L and Five Phospholipid Mixture (100 mg/mL PEG+ 50 $\mu g/mL$ Five Phospholipid Mixture) solution was started through the guide catheter into the aortic root in close approximation to the occlusion. The solutions were introduced initially by a bolus equal to 25% of the hourly drug dose, followed by continuous infusion through the guide catheter for 135 minutes. The occlusion was removed after 120 minutes (15 minutes after the start of drug delivery).

Heart function was monitored by EKG and cardiac output was determined by contrast imaging. The animal was euthenized 1–3 days after the occlusion. The heart was removed for histology and examined. Infarct size was determined by a method of triphenyl tetrazolium chloride (TTC) staining for the area at risk and actual infarct. The area not at risk was stained with a blue pigment or Evan's Blue dye.

Pigs were treated with one of the following test regimens (displayed as total dose):

a) 250 mg/kg PEG20L only (10% ultrafiltered in water) (n=2);

b) 125 $\mu g/kg$ Five Phospholipid Mixture+250 mg/kg PEG20L (n=3).

Four additional pigs were occluded but not treated with any solution, for use as controls.

Of the four controls the mean infarct size (as % risk zone) was 34.5%±7.2%. The controls also showed a marked unresolved S-T segment shift during the ischemic period which reflects severe myocardial ischemia and infarction.

In contrast to the controls, two effects were noted in the treatment groups. First, in some animals, within 2 minutes of the start of drug infusion there was a normalization of the EKG signal disturbances in the occluded hearts. During the ischemic period the normal EKG signal shifted to one in which there was an elevation in the S-T segment indicating an impairment of myocyte repolarization. This elevation disappeared in several pigs treated with PEG20L and Five Phospholipid Mixture. Some pigs that were treated were not included in the infarct measurement data due to technical difficulties in determining the infarct size. However, some of these animals did exhibit a reduction in S-T segment elevation.

Figure 12:
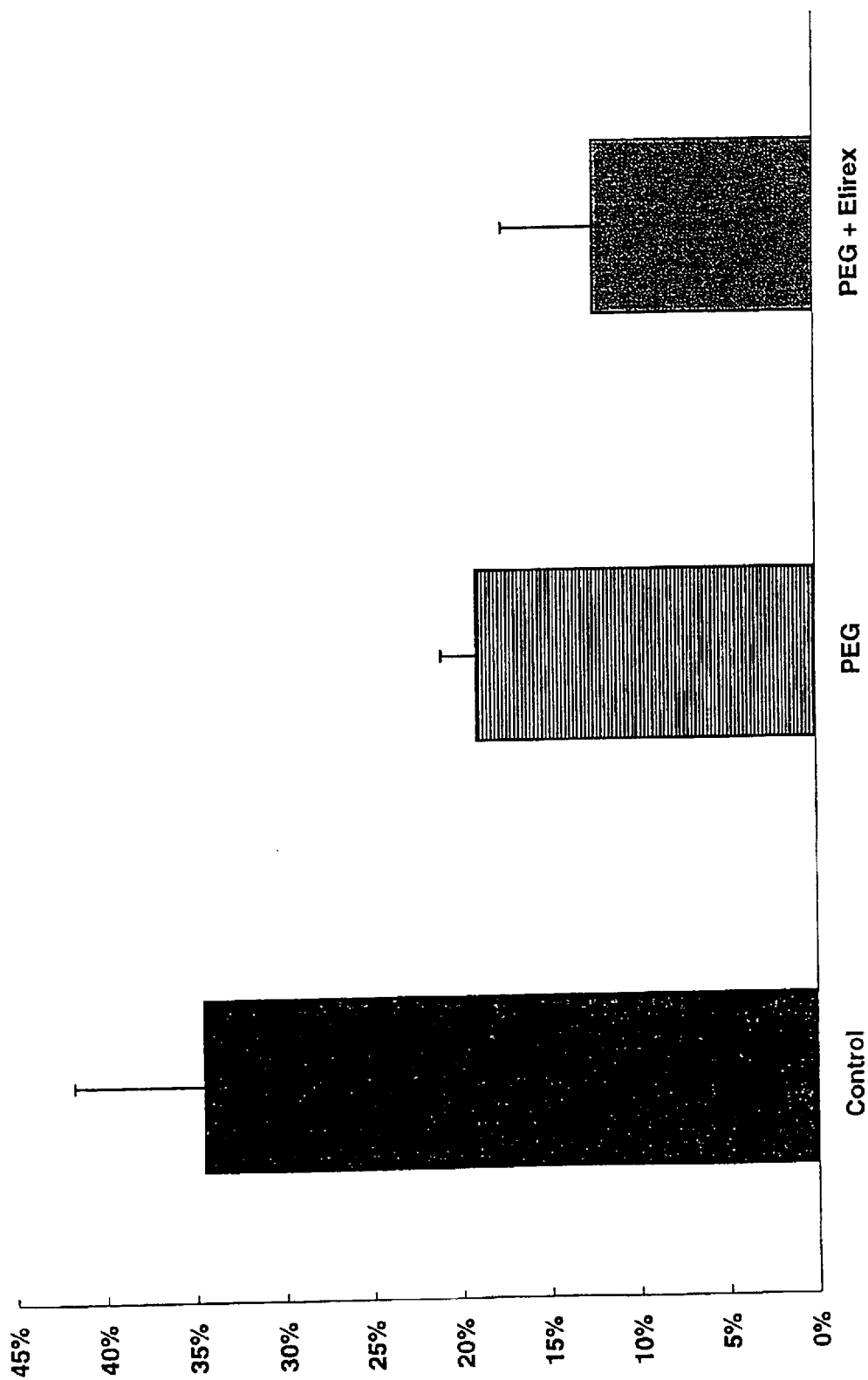
FIG. 12 is a bar graph depicting the effect of the actual infarct size compared to the area at risk in the pig heart model treated with control (solid bar), PEG 20L (striped bar) and a dose of Five Phospholipid Mixture and PEG (gray bar—labeled "PEG+Elirex").

The second effect noted was a decrease in infarct size in the treated animals when compared to the control animals (FIG. 12). In three Five Phospholipid Mixture treated pigs with measurable infarcts, the infarct sizes were reduced to only 12.3%±5.1%, in contrast to 34.5% in the controls.

It is clear from this example that LPA and LPA in combination with PEG are effective therapeutics for the treatment of cardiac ischemia, as both protect tissue from infarct damage and reduce the level of S-T segment shift measured by electrocardiogram.

EXAMPLE 14

Evaluation of Infarct Measurement in a Regional Ischemic Rat Heart Model

The left atrial descending coronary artery (LAD) of each rat was occluded for 20 minutes followed by 2 hours of blood reperfusion. The heart was then removed and the non-ischemic area not at risk for developing an infarction was delineated by perfusing Evan's Blue through all but the LAD of the coronary vasculature. The infarct and area at risk for infarction was identified by perfusing the LAD with triphenyltetrazolium chloride which is metabolized to a red dye in viable tissues while remaining uncolored within the necrotic zone. The heart was then fixed and sliced in order to permit planimetry measurements of both the area at risk for developing the infarction and the actual infarct size itself. The results are expressed as infarct size as a proportion of the area at risk.

At start of reperfusion a mixture of Five Phospholipid Mixture (1 mg/kg) (preparation described in Example 3) and PEG (8 mg/kg) was injected over an approximately two minute period into the left ventricle through a 35 gauge needle. Control rats received a similar volume injection of placebo containing 10 mM citrate/110 mM NaCl, pH 6.5.

Figure 17:
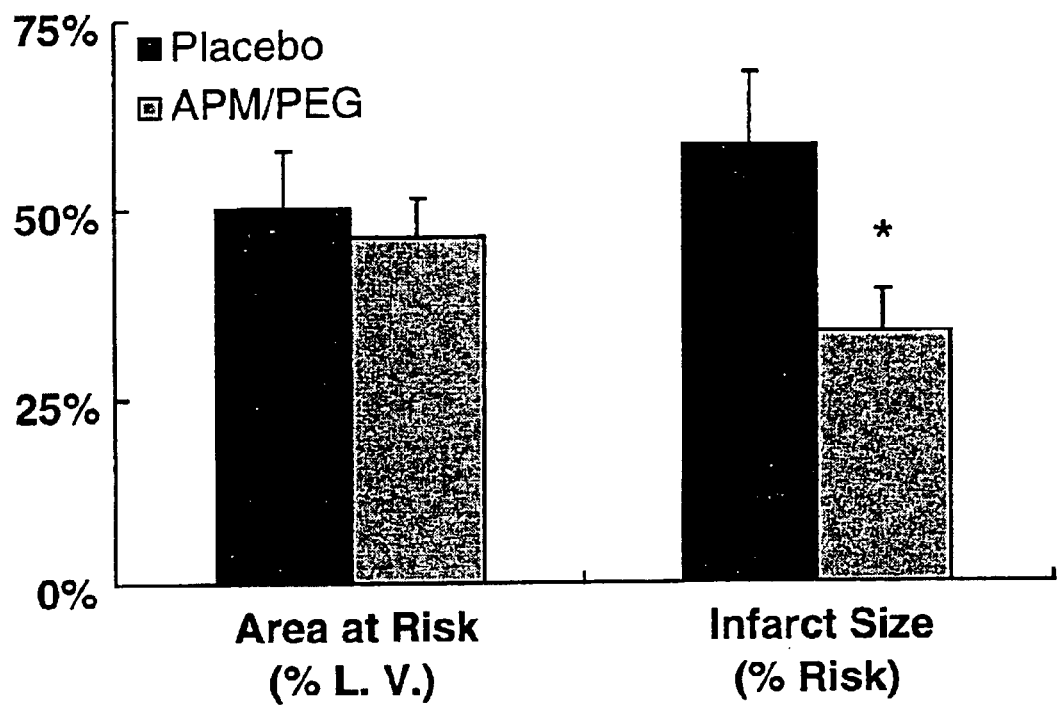
FIG. 17 is a bar graph depicting the actual infarct size compared to the area at risk in the rat heart model treated with placebo (solid bar) or a dose of the combination of Five Phospholipid Mixture and PEG (gray bar, listed in key as "APM/PEG").

The results, in FIG. 17, show that treatment with LPA, in a phospholipid mixture, combined with PEG resulted in a 42% reduction in infarct size relative to placebo-treated rats (p=0.005, n=4 in both groups, two tailed T-test). The areas at risk in the two groups were similar (p=0.42).

EXAMPLE 15

Evaluation of Infarct Measurement in a Regional Ischemic Rabbit Heart Model

Male New Zealand white rabbits were initially anesthetized using a mixture of ketamine (400 mg per rabbit) and xylazine (20 mg per rabbit) administered intramuscularly in two doses, approximately 10 minutes apart. Throughout the study, a level of deep anesthesia is maintained using sodium pentobarbital given intraperitoneally at a dose of approximately 50 mg/hour. All rabbits were intubated and mechanically ventilated using room air supplemented with oxygen. Fluid filled catheters were placed into the jugular vein to administer fluids. A catheter was also placed into the left carotid artery to measure heart rate and blood pressure and to obtain reference blood samples during regional myocardial blood flow measurements. The chest was opened through the left fourth intercostal space. Then, the pericardium was incised and the heart was exposed. A large anterolateral branch of the circumflex artery, or the circumflex artery itself was identified and encircled with a 4-0 silk suture. The ends of the suture were threaded through a piece of flanged tubing, forming a snare, which was later used to occlude the artery. A catheter was then placed into the left atrial appendage to inject the control or test solution, the radioactive microspheres and blue pigment at the conclusion of the procedure.

After the surgical preparation, the rabbits were stabilized for ten minutes. At this time, the rabbits were randomized into either the treatment or control group. The treatment solution contained 1 mg/ml of the Five Phospholipid Mixture, described in Example 3, above, 8 mg/ml PEG 20L, in 10 mM citrate 110 mM NaCl. The control solution contained 10 mM citrate and 110 mM NaCl. Five minutes before occlusion, a bolus dose of 1 mg/kg body weight of either the Five Phospholipid Mixture/PEG solution or the control solution was administered into the left atrium. Immediately following the bolus dose, infusion was started at the rate of 1 mg/kg for one hour into the left atrium. Baseline hemodynamics and core body temperature were recorded. Next, the artery was occluded for 30 minutes. Following this, the hearts were reperfused for three hours. Heart rate and arterial blood pressure were recorded at 20 minutes of occlusion and at time points during reperfusion at a 25 mm/second paper speed. Regional myocardial blood flow measurements were performed on two occasions; during coronary occlusion (20 minutes) to confirm no blood flow in the ischemic zone, and during early reperfusion (30 minutes) to confirm reflow in the same zone. At the end of three hours of reperfusion, the coronary artery is reoccluded. Next, 4 ml of 50% Unisperse blue (Ciby-Geigy, Hawthorne, N.Y.) were infused through the left atrial catheter and allowed to circulate throughout the vascular system. The rabbit was then euthanized by an overdose intravenous injection of xylazine (300 mg) followed by 12 mEq of potassium chloride given into the left atrium. Prospective exclusion criteria included an ischemic risk zone of less than 10% of the left ventricular weight, a regional blood flow of more than 0.2 ml/minute/g in the risk zone during coronary artery occlusion (lack of ischemia), or a regional blood flow of less than 0.4 nml/min/g in the risk zone at 30 minutes of reperfusion (failure to reperfuse).

Infarct size was evaluated as follows. The right ventricle was trimmed off and the left ventricle was sliced transversely into seven or eight sections, approximately two millimeters in thickness. These slices were photographed to identify the ischemic risk regions (uncolored by the blue pigment) and the non-ischemic regions (colored by the blue pigment). The slices were then incubated in a 1% solution of triphenyltetrazolium chloride pre-heated to 37° C. for 10 minutes and rephotographed for analysis of area of necrosis. All sections were later fixed in formalin. These photographic slides were projected and areas of risk (AR) and areas of necrosis (AN) were traced by planimetry. The planimetered areas of each slice were multiplied by the weight of the slice and then summed. Because infarct size is measured from photographic slides, the entire left ventricle was used for the analysis.

Regional myocardial blood flow (RMBF) was measured as follows. Just before measuring RMBF, during occlusion, the atrial catheter was disconnected from the treatment infusion pump. Radioactive microspheres were injected via the atrial catheter. The catheter was then reprimed with approximately 0.2 ml of the drug treatment, and the catheter was reconnected to the pump and infusion continued.

Regional myocardial blood flow was measured with 11 $\mu$m radioactive microspheres labeled with $^{141}$Ce, $^{96}$Nb or $^{103}$Ru (New England Nuclear, North Billerica, Mass.), using approximately 500,000 per injection. These microspheres were injected into the left atrial catheter. At the same time, a reference blood sample was obtained from the carotid artery at 2.06 ml/minute. The blood removed during RMBF measurement was about 5 ml. These volume changes do not cause changes in systemic arterial pressure. At the end of the protocol, after the photographic slides had been taken and the heart weight, myocardial samples were cut from the center of the non-ischemic and the ischemic regions, weighed and counted with the reference blood samples in a well gamma counter. Blood flows at each interval, for ischemic and non-ischemic tissues, were then computed and expressed in ml/minute/g.

The results were as follows. With a risk zone of approximately 25% of the left ventricle, treatment with the control solution resulted in infarct size of approximately 40% of the risk zone on average, as compared to an average of only approximately 25% of the risk zone in the subjects treated with the LPA containing PEG and other phospholipids.

Although the foregoing invention has been described in some detail by way of illustration and example for purposes of clarity of understanding, it will be apparent to those skilled in the art that certain changes and modifications can be practiced. Therefore, the descriptions and examples should not be construed as limiting the scope of the invention, which is delineated by the appended claims.

We claim:

1. A method of treating apoptosis or preserving or restoring function, in a cell, tissue or organ, comprising administering a therapeutically effective amount of a pharmaceutically acceptable composition comprising lysophosphatidic acid.

2. The method of claim 1, wherein said pharmaceutically acceptable composition further comprises a potentiating component.

3. The method of claim 2, wherein said potentiating component comprises a polyethylene glycol.

4. The method of claim 2, wherein said potentiating component comprises a protein.

5. The method of claim 2, wherein said potentiating component comprises a lipid membrane structure.

6. The method according to claim 1, comprising administering said composition to a patient suffering from a condition related to apoptosis, ischemia, traumatic injury or reperfusion damage.

7. The method according to claim 1, comprising administering said composition to a patient suffering from gastrointestinal perturbation.

8. The method according to claim 7, wherein the gastrointestinal perturbation is caused by a stimulus selected from the group consisting of viruses, chemotherapeutic agents, radiation, infectious diseases, inflammatory bowel disease, and diarrhea-causing organisms.

9. The method according to claim 8, wherein the virus is human immunodeficiency virus.

10. The method according to claim 1, wherein the method diminishes apoptosis-related problems associated with immunosuppressing viruses, chemotherapeutic agents, or radiation and immunosuppressive drugs.

11. The method according to claim 6, wherein the reperfusion damage is associated with coronary artery obstruction; stroke; cerebral infarction; spinal/head trauma and concomitant severe paralysis; frostbite; coronary angioplasty; blood vessel attachment; limb attachment; organ attachment; or kidney reperfusion.

12. The method of claim 1 wherein the LPA has the formula:

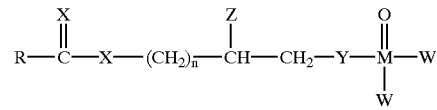

or a cyclic phosphate derivative thereof having the structure:

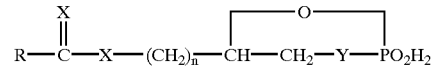

wherein
each X is independently O or S;
M is P or S, where when M is S, one W is (=O);
each W is independently SH, OH, OCH$_2$CH(NH$_2$)CO$_2$H, OCHCH$_3$CH(NH$_2$)CO$_2$H, OPO$_3$H$_2$, or OPO$_2$HOPO$_3$H$_2$, where if one W is OPO$_3$H$_2$ or OPO$_2$HOPO$_3$H$_2$, the remaining W is OH;
Z is OH, SH, NH$_2$, halogen, OPO$_3$H$_2$, H, O(CH$_2$)$_b$CH$_3$ where b=0 to about 2, or SO$_3$H;
R is unsubstituted or substituted, saturated or unsaturated, straight or branched-chain alkyl having from about 10 to about 24 carbon atoms, or ((CH$_2$)$_m$O)$_p$(CH$_2$)$_m$W where p is an integer from 1 to about 900 and where each m is independently an integer from 2 to about 10 and W is OH, or O(CH$_2$)$_q$CH$_3$ where q is an integer from 0 to about 10;
Y is O or S; and
n is an integer from 0 to about 10;
or a pharmaceutically acceptable salt thereof.

13. The method according to claim 12, wherein R is an alkyl having between about 10 to about 24 carbon atoms, wherein between 0 and 11, inclusive, of the carbon-carbon bonds are unsaturated, and mixtures thereof.

14. The method according to claim 12, wherein R is an alkyl having 18 carbon atoms, wherein 1 or 2 of the carbon-carbon bonds are unsaturated, and mixtures thereof.

15. The method according to claim 1, wherein the LPA has the formula:

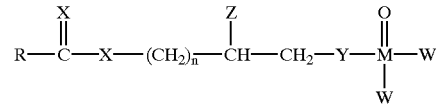

or a cyclic phosphate derivative thereof having the structure:

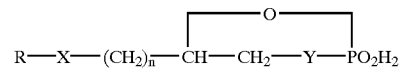

wherein
X is O, S, or CH$_2$;
M is P or S, where when M is S, one W is (=O);
each W is independently SH, OH, OCH$_2$CH(NH$_2$)CO$_2$H, OCHCH$_3$CH(NH$_2$)CO$_2$H, OPO$_3$H$_2$, or OPO$_2$HOPO$_3$H$_2$, where if one W is OPO$_3$H$_2$ or OPO$_2$HOPO$_3$H$_2$, the remaining W is OH;
Z is OH, SH, NH$_2$, halogen, OPO$_3$H$_2$, H or SO$_3$H;
R is unsubstituted or substituted, saturated or unsaturated, straight or branched-chain alkyl having from about 10 to about 24 carbon atoms, or ((CH$_2$)$_m$O)$_p$(CH$_2$)$_m$W where p is an integer from 1 to about 900 and where each m is independently an integer from 2 to about 10 and W is OH, or $O(CH_2)_q CH_3$ where q is an integer from 0 to about 10;

Y is O or S; and n is an integer from 0 to about 10;

or a pharmaceutically acceptable salt thereof.

16. The method according to claim 15 wherein R is an alkyl having between about 10 and about 24 carbon atoms, wherein between 0 and 11, inclusive, of the carbon-carbon bonds are unsaturated, and mixtures thereof.

17. The method according to claim 15, wherein R is an alkyl having 18 carbon atoms, wherein 1 or 2 of the carbon-carbon bonds are unsaturated, and mixtures thereof.

18. The method according to claim 1, wherein the LPA has the formula:

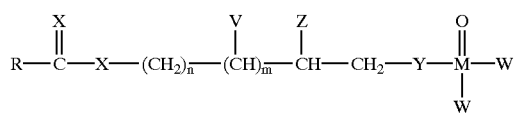

or a cyclic phosphate derivative thereof having the structure:

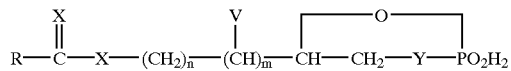

wherein each V is independently OH, SH, H, $NH_2$, halogen, $OPO_3H_2$, or $OSO_3H$;

each X is independently O or S;

M is P or S, where when M is S, one W is (=O);

each W is independently SH, OH, $OCH_2CH(NH_2)CO_2H$, $OCHCH_3CH(NH_2)CO_2H$, $OPO_3H_2$, or $OPO_2HOPO_3H_2$, where if one W is $OPO_3H_2$ or $OPO_2HOPO_3H_2$, the remaining W is OH;

Z is OH, SH, $NH_2$, halogen, $OPO_3H_2$, H or $SO_3H$;

R is unsubstituted or substituted, saturated or unsaturated, straight or branched-chain alkyl having from about 10 to about 24 carbon atoms, or $((CH_2)_pO)_q(CH_2)_pV$ where q is an integer from 1 to about 900 and where each p is independently an integer from 2 to about 10 and V is OH, or $O(CH_2)_b CH_3$ where b is an integer from 0 to about 10;

Y is O or S;

n is an integer from 0 to about 10; and m is an integer from 0 to about 10;

or a pharmaceutically acceptable salt thereof.

19. The method to claim 18 wherein R is an alkyl having between about 10 and about 24 carbon atoms, wherein between 0 and 11, inclusive, of the carbon-carbon bonds are unsaturated, and mixtures thereof.

20. The method according to claim 18, wherein R is an alkyl having 18 carbon atoms, wherein 1 or 2 of the carbon-carbon bonds are unsaturated, and mixtures thereof.

21. The method according to claim 1, wherein the LPA has the formula:

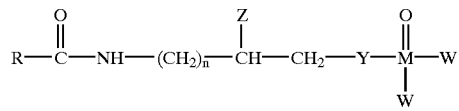

or a cyclic phosphate derivative thereof having the structure:

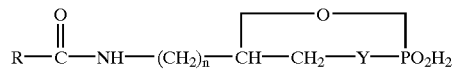

or the reverse amide thereof, wherein

Z is OH, SH, $NH_2$, halogen, $OPO_3H_2$, H, or $SO_3H$;

M is P or S, where when M is S, one W is (=O);

each W is independently SH, OH, $OCH_2CH(NH_2)CO_2H$, $OCHCH_3CH(NH_2)CO_2H$, $OPO_3H_2$, or $OPO_2HOPO_3H_2$, where if one W is $OPO_3H_2$ or $OPO_2HOPO_3H_2$, the remaining W is OH;

R is an amino acid side chain unsubstituted or a branched amino acid side chain, or an alkylated amino acid side chain, or substituted, saturated or unsaturated, straight or branched-chain alkyl having from about 10 to about 24 carbon atoms, or $((CH_2)_mO)_p(CH_2)_mW$ where p is an integer from 1 to about 900 and where each m is independently an integer from 2 to about 10 and W is OH, or $O(CH_2)_q CH_3$ where q is an integer from 0 to about 10;

Y is O or S; and n is an integer from 0 to about 10;

or a pharmaceutically acceptable salt thereof.

22. The method according to claim 21 wherein R is an alkyl having between about 10 and about 24 carbon atoms, wherein between 0 and 11, inclusive, of the carbon-carbon bonds are unsaturated, and mixtures thereof.

23. The method according to claim 21, wherein R is an alkyl having 18 carbon atoms, wherein 1 or 2 of the carbon-carbon bonds are unsaturated, and mixtures thereof.

24. A method of treating apoptosis, preserving or restoring function in a cell, tissue or organ comprising administering internally or in vitro a therapeutically effective amount of a pharmaceutically acceptable composition comprising lysophosphatidic acid to cells.

25. The method according to claim 24, wherein said composition is a solution and the LPA is present in an amount of from about 0.00001% to about 10% (weight/volume).

26. The method according to claim 24, wherein said composition is a solid and the LPA is present in an amount of from about 0.00001% to 50% (weight/weight).

27. The method according to claim 24, wherein said composition further comprises a pharmaceutically acceptable excipient.

28. The method according to claim 27, wherein the pharmaceutically acceptable excipient is selected from the group consisting of sterile solutions, sterile isotonic solutions, ingestable liquids, pharmaceutically acceptable aerosols and solutions for organ, tissue, or cell preservation or transplantation.

29. The method according to claim 24, wherein said cells are cardiac cells and wherein said composition is delivered by intracoronary administration to said cardiac cells.

* * * * *